United States Patent
Wilson et al.

(10) Patent No.: US 12,128,479 B2
(45) Date of Patent: Oct. 29, 2024

(54) DMLS ORTHOPEDIC INTRAMEDULLARY DEVICE AND METHOD OF MANUFACTURE

(71) Applicant: Smith & Nephew, Inc., Memphis, TN (US)

(72) Inventors: Darren J. Wilson, York (GB); David B. Harness, Eads, TN (US); Henry Faber, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 331 days.

(21) Appl. No.: 16/560,703

(22) Filed: Sep. 4, 2019

(65) Prior Publication Data
US 2019/0388128 A1 Dec. 26, 2019

Related U.S. Application Data

(63) Continuation of application No. 15/302,899, filed as application No. PCT/US2015/025429 on Apr. 10, 2015, now abandoned.
(Continued)

(51) Int. Cl.
*B22F 10/364* (2021.01)
*A61B 17/72* (2006.01)
(Continued)

(52) U.S. Cl.
CPC .......... *B22F 10/364* (2021.01); *A61B 17/72* (2013.01); *A61B 17/7225* (2013.01);
(Continued)

(58) Field of Classification Search
CPC .................. A61B 17/7225; B22F 10/364
See application file for complete search history.

(56) References Cited

U.S. PATENT DOCUMENTS

| 4,475,545 A | 10/1984 | Ender |
| 4,784,127 A | 11/1988 | Mattheck et al. |

(Continued)

FOREIGN PATENT DOCUMENTS

| CN | 2343985 Y | 10/1999 |
| CN | 1845711 A | 10/2006 |

(Continued)

OTHER PUBLICATIONS

Boyer, Rodney Welsch, Gerhard Collings, E.W.. (1994). Materials Properties Handbook—Titanium Alloys—8.1.3 Alpha + Beta-Phase Titanium Alloys. ASM International. (Year: 1994).*
(Continued)

*Primary Examiner* — Jophy S. Koshy
*Assistant Examiner* — Joshua S Carpenter
(74) *Attorney, Agent, or Firm* — KDW Firm PLLC

(57) ABSTRACT

An orthopedic device, such as an intramedullary nail for internal fixation of a bone and a method of manufacturing the same. The orthopedic device may be formed from a medical grade powder via an additive manufacturing process. The forming process may include heat treating the additive manufactured component and machining the heat treated additive manufactured component to form the orthopedic device. Further, the orthopedic device may be formed to include an internal sensor probe channel that extends within at least a portion of the wall of the device, but which does not protrude through an outer portion of the wall. Embodiments further include a dynamizing intramedullary nail that accommodate adjustments in the relative axial positions of one or more sections of the orthopedic device. The devise may include features in an inner region of the orthopedic device that may alter an elastic modulus of the orthopedic device.

17 Claims, 41 Drawing Sheets

Related U.S. Application Data

(60) Provisional application No. 61/978,804, filed on Apr. 11, 2014, provisional application No. 61/978,806, filed on Apr. 11, 2014.

(51) Int. Cl.

| | | |
|---|---|---|
| *B22F 3/15* | (2006.01) | |
| *B22F 5/10* | (2006.01) | |
| *B22F 10/28* | (2021.01) | |
| *B22F 10/64* | (2021.01) | |
| *B22F 10/66* | (2021.01) | |
| *B23K 26/08* | (2014.01) | |
| *B23K 26/10* | (2006.01) | |
| *B23K 26/354* | (2014.01) | |
| *B24C 1/08* | (2006.01) | |
| *B33Y 10/00* | (2015.01) | |
| *B33Y 80/00* | (2015.01) | |
| *C22C 14/00* | (2006.01) | |
| *C22F 1/18* | (2006.01) | |
| *A61B 17/00* | (2006.01) | |
| *B22F 3/24* | (2006.01) | |
| *B22F 10/366* | (2021.01) | |

(52) U.S. Cl.
CPC ............ *A61B 17/7233* (2013.01); *B22F 3/15* (2013.01); *B22F 5/10* (2013.01); *B22F 10/28* (2021.01); *B23K 26/08* (2013.01); *B23K 26/103* (2013.01); *B23K 26/354* (2015.10); *B24C 1/086* (2013.01); *B33Y 10/00* (2014.12); *B33Y 80/00* (2014.12); *C22C 14/00* (2013.01); *C22F 1/183* (2013.01); *A61B 2017/00526* (2013.01); *B22F 2003/248* (2013.01); *B22F 10/366* (2021.01); *B22F 10/64* (2021.01); *B22F 10/66* (2021.01); *B22F 2998/10* (2013.01); *Y02P 10/25* (2015.11)

(56) References Cited

U.S. PATENT DOCUMENTS

| | | |
|---|---|---|
| 4,877,019 A | 10/1989 | Vives |
| 5,344,494 A * | 9/1994 | Davidson ............ A61F 2/30767 451/39 |
| 5,573,536 A | 11/1996 | Grosse et al. |
| 5,993,456 A | 11/1999 | Speitling et al. |
| 6,558,388 B1 | 5/2003 | Bartsch et al. |
| 7,537,664 B2 | 5/2009 | ONeill et al. |
| 7,771,428 B2 | 8/2010 | Siravo et al. |
| 8,147,861 B2 | 4/2012 | Jones et al. |
| 8,268,099 B2 | 9/2012 | ONeill et al. |
| 8,268,100 B2 | 9/2012 | ONeill et al. |
| 8,457,930 B2 | 6/2013 | Schroeder |
| 8,778,029 B2 | 7/2014 | Baumgart |
| 8,888,860 B2 | 11/2014 | Taylor |
| 8,992,703 B2 | 3/2015 | ONeill et al. |
| 9,072,545 B2 | 7/2015 | Biedermann et al. |
| 9,427,266 B2 | 8/2016 | Kmiec, Jr. |
| 9,456,901 B2 | 10/2016 | Jones et al. |
| 9,730,739 B2 | 8/2017 | Taylor et al. |
| 2003/0069581 A1 | 4/2003 | Stinson et al. |
| 2005/0203517 A1 | 9/2005 | Jahng et al. |
| 2006/0009857 A1* | 1/2006 | Gibbs ............... A61F 2/30767 623/23.4 |
| 2006/0147332 A1 | 7/2006 | Jones et al. |
| 2007/0100343 A1 | 5/2007 | Cole et al. |
| 2007/0118243 A1 | 5/2007 | Schroeder et al. |
| 2007/0233064 A1 | 10/2007 | Holt |
| 2008/0262496 A1 | 10/2008 | Schlienger et al. |
| 2008/0269745 A1 | 10/2008 | Justin |
| 2008/0306554 A1* | 12/2008 | McKinley .......... A61B 17/8605 606/76 |
| 2009/0028919 A1 | 1/2009 | Dancu |
| 2009/0254088 A1 | 10/2009 | Soubeiran |
| 2010/0291401 A1* | 11/2010 | Medina ................ B23K 26/38 428/593 |
| 2011/0060373 A1* | 3/2011 | Russell ............. A61B 17/0401 606/86 R |
| 2011/0178520 A1 | 7/2011 | Taylor et al. |
| 2011/0190904 A1 | 8/2011 | Lechmann et al. |
| 2012/0130370 A1 | 5/2012 | Kinmon |
| 2012/0245700 A1 | 9/2012 | Sidebotham |
| 2013/0231750 A1 | 9/2013 | Taylor |
| 2013/0274745 A1 | 10/2013 | Kmiec, Jr. |
| 2014/0228845 A1 | 8/2014 | Gorsline et al. |
| 2015/0258735 A1 | 9/2015 | ONeill et al. |
| 2016/0001401 A1* | 1/2016 | Dimter ................ B29C 64/153 219/76.12 |
| 2017/0014235 A1 | 1/2017 | Jones et al. |

FOREIGN PATENT DOCUMENTS

| | | | |
|---|---|---|---|
| CN | 2902213 Y | 5/2007 | |
| CN | 101010044 A | 8/2007 | |
| CN | 101573085 A | 11/2009 | |
| CN | 103637840 A | 3/2014 | |
| EP | 0601804 A1 | 6/1994 | |
| EP | 1913887 A1 | 4/2008 | |
| EP | 2468216 A1 | 6/2012 | |
| EP | 2712306 A2 | 4/2014 | |
| JP | 2002038201 A * | 2/2002 | ............ B22F 3/1055 |
| WO | 02094113 A1 | 11/2002 | |
| WO | 2008035089 A1 | 3/2008 | |
| WO | 2008044011 A2 | 4/2008 | |
| WO | 2008105874 A1 | 9/2008 | |
| WO | 2010045128 A1 | 4/2010 | |
| WO | 2010120990 A1 | 10/2010 | |
| WO | WO2012/140427 A1 | 10/2012 | |
| WO | 2012158865 A2 | 11/2012 | |
| WO | 2013126027 A1 | 8/2013 | |
| WO | 2013155500 A1 | 10/2013 | |

OTHER PUBLICATIONS

Espacenet machine translation of JP-2002038201-A retrieved on Oct. 5, 23 (Year: 2002).*
Campbell, F. C .. (2013). Metals Fabrication - Understanding the Basics - 8.4.2.5 Extrusion. (p. 404). ASM International. (Year: 2013).*
Chinese Search report; State Intellectual Property Office, Peoples Republic of China; Chinese Patent Application No. 201580031357.9; Oct. 15, 2018; 6 pages.
Chinese Office Action (1st); State Intellectual Property Office, Peoples Republic of China; Chines Patent Application No. 201580031357.9; Oct. 24, 2018; 15 pages.
International Search Report; European Patent Office; International Application No. PCT/US2015/025429, Nov. 6, 2015, 6 pages.
Written Opinion of the International Searching Authority; Euopean Patent Office; International Application No. PCT/US2015/025429, Nov. 5, 2015, 10 pages.
Vojislav Petrovic et al., "Additive Manufacturing Solutions for Improved Medical Implants" Biomedicine, Mar. 1, 2012; pp. 147-181; Chapter 7; ISBN 978-953-51-0352-3.
Examination report No. 1 for Australian Patent Application No. 2015243170, mailed Jun. 6, 2019.
Search Report under section 45 of the Patents Act 1990 for Australian Application No. 2015243170, dated Aug. 25, 2020, 4 pages.
Communication pursuant to Rule 164(2)(b) and Article 94(3) EPC, for EP application No. 15718724.6 dated Sep. 30, 2020, 16 pages.
Betz, A., et al., First fully implantable intramedullary system for callus distraction—intramedullary nail with programmable drive for leg lengthening and segment displacement. Principles and initial clinical results, Chirurg 61 (8):605-9 (1990).
Second Office Action for Chinese Patent Application No. 201580031357.9, mailed Aug. 9, 2019.

(56) References Cited

OTHER PUBLICATIONS

European Examination Report, European Patent Office, 8 Pages, dated Dec. 5, 2023.

* cited by examiner

| | Laser Power (Watts) | Platform Size mm x mm | Build Time 16 Test Bars (hrs) | Layer Thickness (mm) | Layers # | Est Recoat Time (secs) | Total Recoat Time (hrs) | Est. Scan Time (hrs) | Scan time per nail (secs) | Max No. Nails # | Recoat Time (280mm) (hrs) | Scan Time Full Build (280mm) (hrs) |
|---|---|---|---|---|---|---|---|---|---|---|---|---|
| ARCAM S12 | 3000 | 200 x 200 | 18 | 0.07 | 1429 | 12.00 | 4.8 | 13.2 | 2.09 | 484 | 31.1 | 1121.3 |
| CONCEPT M2 | 200 | 250 x 250 | 21 | 0.03 | 3333 | 10.00 | 9.3 | 11.7 | 0.79 | 484 | 25.9 | 994.4 |
| EOS M280 | 340 | 250 x 250 | 10 | 0.06 | 1667 | 9.00 | 4.2 | 5.8 | 0.79 | 484 | 23.3 | 494.1 |
| REALIZER | 172 | 125 x 125 | 22 | 0.05 | 2000 | 9.00 | 5.0 | 17.0 | 1.91 | 484 | 23.3 | 1439.9 |
| RENISHAW Am250 | 200 | 250 x 250 | 17 | 0.05 | 2000 | 9.48 | 5.266 | 11.7 | 1.32 | 484 | 24.6 | 993.9 |
| SLM-SOLUTIONS 280 HL | 275 | 280 x 280 | 12.6 | 0.05 | 2000 | 8.00 | 4.4 | 8.2 | 0.92 | 484 | 20.7 | 690.8 |

| | Build time full build (hrs) | Build time full build (days) | Ave. build time per nail (hrs) | Parts per yr | Machine price (est) £ | Machine price per part £ | No. times material used | Material grade | Laser focal spot (mm) | Argon used in test (l) |
|---|---|---|---|---|---|---|---|---|---|---|
| ARCAM S12 | 1152.38 | 48.02 | 5.95 | 3679.21 | 600000 | 32.62 | 2 | 23 | 0.2 | Helium |
| CONCEPT M2 | 1020.37 | 42.52 | 5.27 | 4155.21 | 500000 | 24.07 | 12 | 23 | n/a | 18900 |
| EOS M280 | 517.42 | 21.56 | 2.67 | 8194.25 | 500000 | 12.20 | 5 | 23/5 | 0.08 | 6000 |
| REALIZER | 1463.23 | 60.97 | 7.56 | 2897.58 | 400000 | 27.61 | 1 | 5 | 0.03 | 400 |
| RENISHAW Am250 | 1018.44 | 42.44 | 5.26 | 4163.05 | 500000 | 24.02 | 130 | 23 | 0.075 | 900 |
| SLM-SOLUTIONS 280 HL | 711.52 | 29.65 | 3.68 | 5958.88 | 500000 | 16.78 | 3 | 5 | 0.083 | 40 |

FIG. 5

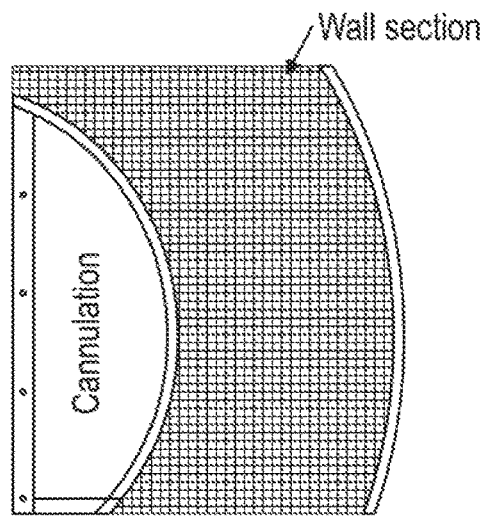
FIG. 10A
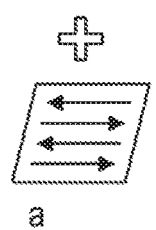
a
FIG. 10B
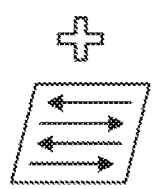
b
FIG. 10C
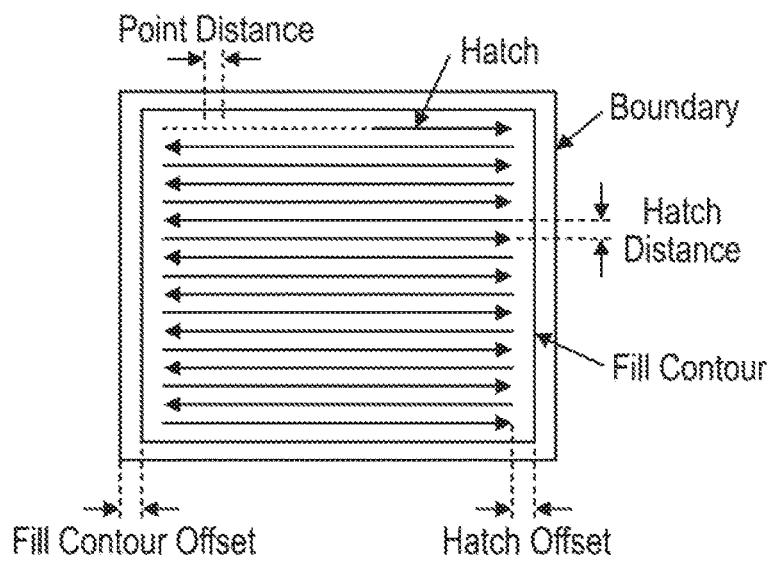
FIG. 10D

| Sample | Laser Power (W) | Dimensions (mm) | | | | Cycle to failure |
|---|---|---|---|---|---|---|
| | | Length | Diameter | Cannulation | | |
| | | | | Top | Bottom | |
| Control | Machined | 77.1 | 10.0 | 5.4 | 5.4 | Runout |
| 2 | 140 | 79.0 | 10.2 | 4.4 | 4.5 | 1,820 |
| 4 | 180 | 78.6 | 10.1 | 4.4 | 4.4 | 14,733 |
| 7 | 220 | 77.6 | 10.3 | 4.3 | 4.3 | 40,670 |
| 9 | 260 | 77.4 | 10.3 | 4.0 | 4.1 | 54,943 |
| 11 | 300 | 79.1 | 10.5 | 3.5 | 4.5 | 55,250 |
| 12 | 400 | 76.7 | 10.4 | 4.2 | 4.9 | 85,673 |

| MACHINE SUPPLIER | MACHINE TYPE | ORIGIN |
|---|---|---|
| Concept Laser | Laser | Germany |
| EOS | Laser | Germany |
| SLM Solutions | Laser | Germany |
| Phenix | Laser | France |
| Realizer | Laser | Germany |
| Renishaw | Laser | UK |
| Arcam | Electron Beam | Sweden |

| Supplier | Ra (µm) | Rp (µm) | Rv (µm) |
|---|---|---|---|
| Realizer | 5.43 | 29.04 | 24.60 |
| Concept Laser | 6.52 | 20.81 | 24.23 |
| SLM Solutions | 7.58 | 28.11 | 23.27 |
| EOS Grade 23 | 9.54 | 45.84 | 28.52 |
| EOS Grade 5 | 9.62 | 53.59 | 27.55 |
| Renishaw | 10.62 | 43.95 | 38.37 |
| Arcam | 23.4 | 36.30 | 48.20 |

| Sample | Average lamella thickness, microns |
|---|---|
| SLM | 4.05 |
| Renishaw | 4.80 |
| Realizer | 5.01 |
| EOS Grade 23 | 5.10 |
| EOS Grade 5 | 6.12 |
| Concept Laser | 4.70 |
| Arcam | 4.10 |

| ID | Machine/Powder Grade | Heat Treatment | Elongation (%) | UTS (MPa) |
|---|---|---|---|---|
| A | EOS (23) | HIP | 18.6 | 991 |
| B | EOS (5) | HIP | 17.5 | 946 |
| C | Renishaw (23) | HIP | 18.4 | 960 |
| D | Concept Laser (23) | HIP | 15.8 | 983 |
| E | SLM (23) | HIP | 13.7 | 969 |
| F | Realizer (G5) | None | 1.5 | 1103 |
| G | Realizer (G5) | HIP | 17.2 | 988 |
| H | Arcam (G23) | HIP | 10.4 | 875 |
| J | Phenix | None | 8.8 | 1249 |
| K | Wrought Ti-64 | HIP | 5.3 | 1069 |

FIG. 30

| Scanner Optics | Laser on Time(s) | Working Time for the Machine(s) | Production time for 100 Intramedullary Nails |
|---|---|---|---|
| Single | 360, 784 | 392, 072 (108 hrs 52 min) | 4 days 13 hrs 15 min |
| Twin | 180, 392 | 211, 680 (58 hrs 48 min) | 2 days 10 hrs 48 min |
| Quad | 90, 196 | 121, 484 (33 hrs 40 min) | 1 day 9 hrs 40 min |

FIG. 31

| Scanner Optics | Laser On Time(s) | Working Time for the Machine(s) | Production time for 100 Intramedullary Nails |
|---|---|---|---|
| Single | 173, 120 | 204, 408 (58 hrs 52 min) | 2 days 8 hrs 48 min |
| Twin | 86, 560 | 117, 848 (32 hrs 46 min) | 1 day 8 hrs 46 min |
| Quad | 43, 280 | 74, 568 (20 hrs 42 min) | 0 days 20 hrs 42 min |

FIG. 32

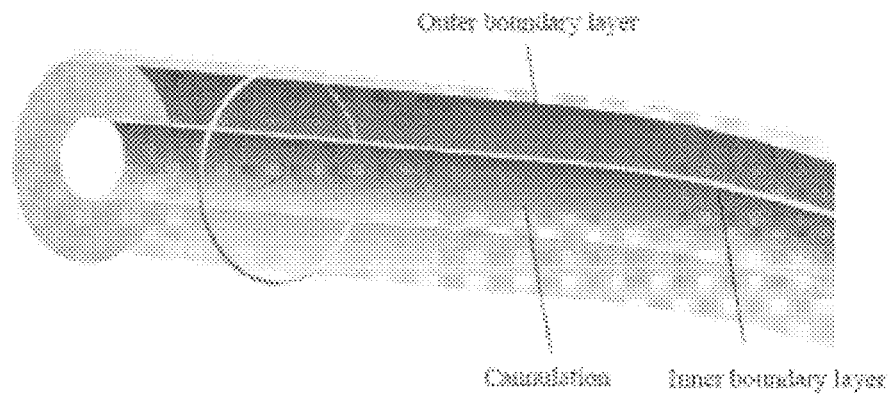
FIG. 35
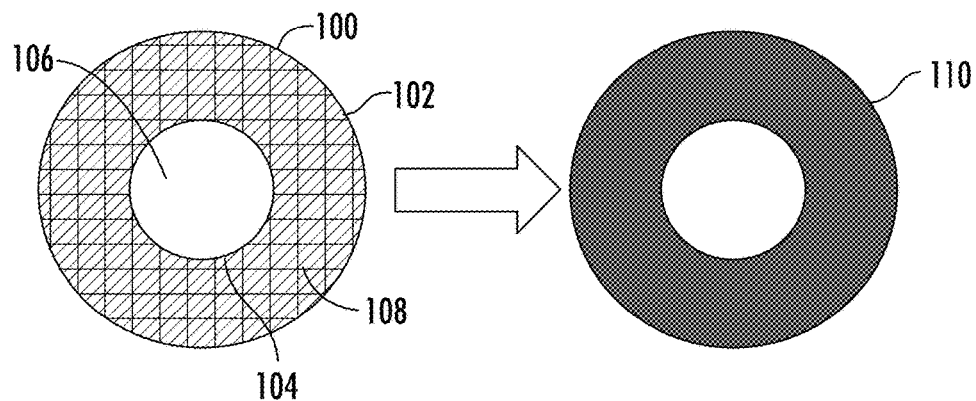
FIG. 36A
FIG. 36B
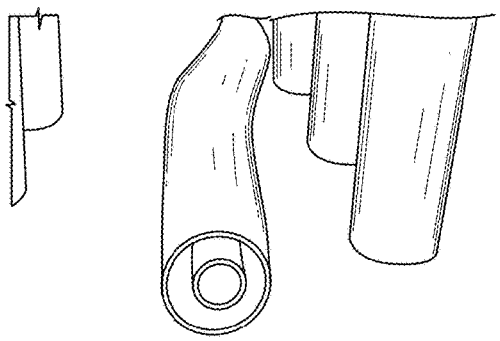
FIG. 37A
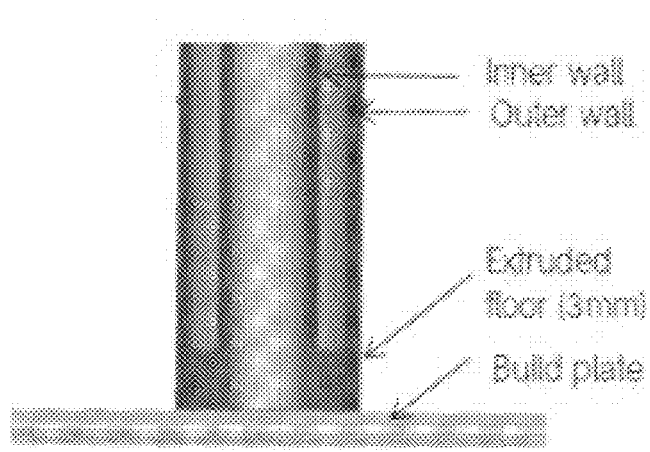
FIG. 37B

| Parameter | |
|---|---|
| Layer thickness | 60 μm |
| Spot size | 20 μm |
| Exposure | 60 μs |
| Point distance | 60 μm |
| Laser power | 300 W |
| Scanning Speed | 1000 mm/s |

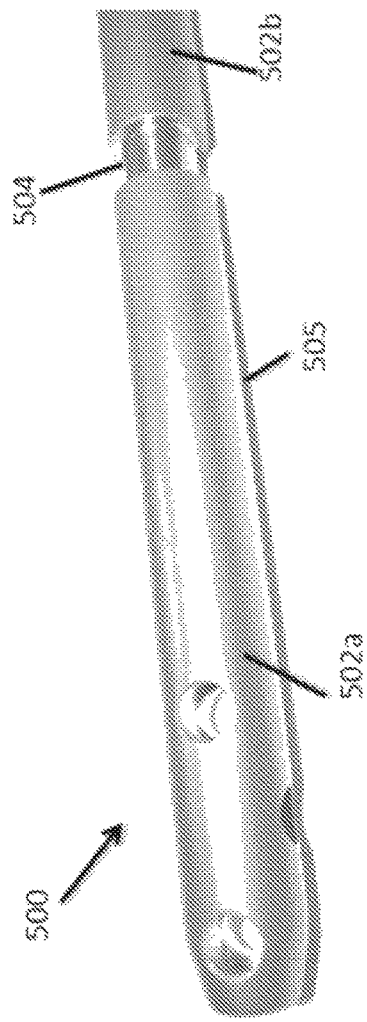
FIG. 49
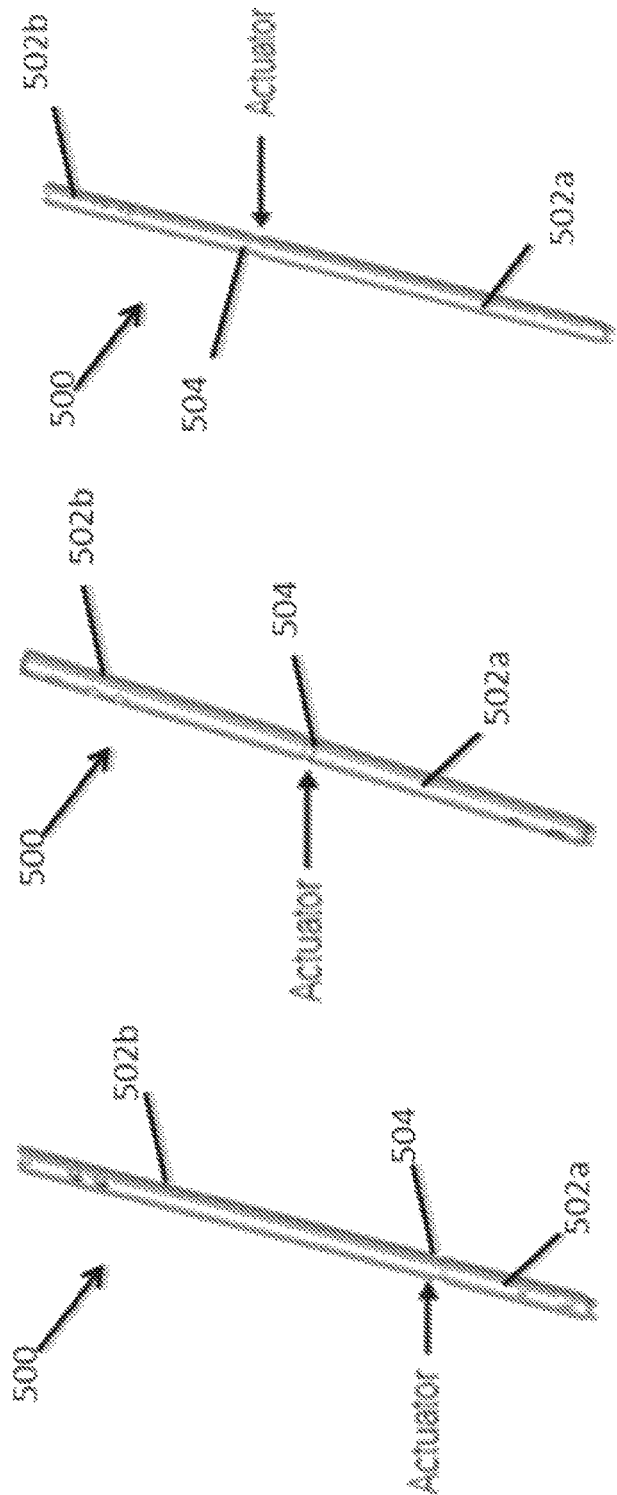
FIG. 50A
FIG. 50B
FIG. 50C

| OD (mm) | ID (mm) | WALL THICKNESS (mm) | THEORETICAL BENDING STIFFNESS (N.m^2) | THEORETICAL TORSIONAL STIFFNESS (N.m^2) |
|---|---|---|---|---|
| 10 | 5.4 | 2.3 | 51.2 (STANDARD) | 35.9 (STANDARD) |
| 11.5 | 5.3 | 3.1 | 93.1 (STANDARD) | 65.6 (STANDARD) |
| 13 | 8.43 | 2.3 | 132.0 (STANDARD) | 92.6 (STANDARD) |
| 10 | 7.0 | 1.5 | 42.5 (CUSTOM WALL THICKNESS) | 29.8 (CUSTOM WALL THICKNESS) |
| 11.5 | 8.5 | 1.5 | 68.7 (CUSTOM WALL THICKNESS) | 48.2 (CUSTOM WALL THICKNESS) |
| 13 | 10.0 | 1.5 | 103.9 (CUSTOM WALL THICKNESS) | 72.9 (CUSTOM WALL THICKNESS) |

| OD (mm) | ID (mm) | WALL THICKNESS (mm) | % POROSITY | THEORETICAL BENDING STIFFNESS (N.m^2) | THEORETICAL TORSIONAL STIFFNESS (N.m^2) |
|---|---|---|---|---|---|
| 10 | 5.4 | 2.3 | – | 51.2 (STANDARD) | 35.9 (STANDARD) |
| 11.5 | 5.3 | 3.1 | – | 93.1 (STANDARD) | 65.6 (STANDARD) |
| 13 | 8.43 | 2.3 | – | 132.0 (STANDARD) | 92.6 (STANDARD) |
| 13 | 4.80 | 4.1 | 0 | 156.9 (CUSTOM WALL THICKNESS TO ACCOMMODATE POROSITY) | 110.1 (CUSTOM WALL THICKNESS TO ACCOMMODATE POROSITY) |
| 13 | 4.80 | 4.1 | 24 | 119.2 (CUSTOM WALL THICKNESS + POROSITY) | 83.4 (CUSTOM WALL THICKNESS TO ACCOMMODATE POROSITY) |

|  | OD (mm) | WALL (mm) | ID (mm) | BENDING STIFFNESS (N.m^2) | TORSIONAL STIFFNESS (N.m^2) |
|---|---|---|---|---|---|
| CUSTOM 10 mm OD NAIL |  |  |  |  |  |
| INNER SECTION | 7.2 | 1.2 | 4.8 | 12.1 | 8.5 |
| OUTER SECTION | 10 | 1.2 | 7.6 | 37.3 | 26.2 |
| STANDARD TRIGEN META TIBIAL NAIL (8.5 mm OD) | 8.5 | 1.9 | 4.8 | 26.3 | 18.5 |
| STANDARD TRIGEN META TIBIAL NAIL (10 mm OD) | 10 | 2.3 | 5.4 | 51.2 | 35.9 |

FIG. 70

DMLS ORTHOPEDIC INTRAMEDULLARY DEVICE AND METHOD OF MANUFACTURE

CROSS-REFERENCE TO RELATED APPLICATION

The present application is a continuation of pending U.S. patent application Ser. No. 15/302,899, filed Oct. 7, 2016, which is a U.S. National Phase of International PCT Application No. PCT/US2015/025429, filed on Apr. 10, 2015, which claims the benefit of U.S. Provisional Patent Application Ser. No. 61/978,804, filed Apr. 11, 2014, and U.S. Provisional Patent Application Ser. No. 61/978,806, filed Apr. 11, 2014, the contents of each application are hereby incorporated by reference in their entirety.

FIELD OF THE INVENTION

The present invention relates generally to implants for use in orthopedic surgeries or procedures, and more particularly but not exclusively relates to an orthopedic intramedullary device, such as, for example, an orthopedic intramedullary nail, for internal fixation of a bone and a method of manufacturing the same.

BACKGROUND

Orthopedic fixation devices may be used, for example, to stabilize an injury, to support a bone fracture, to fuse a joint, and/or to correct a deformity. The orthopedic fixation device may be attached permanently or temporarily, and may be attached to the bone at various locations, including implanted within a canal or other cavity of the bone, implanted beneath soft tissue and attached to an exterior surface of the bone, or disposed externally and attached by fasteners such as screws, pins, and/or wires. Some orthopedic fixation devices allow the position and/or orientation of two or more bone pieces, or two or more bones, to be adjusted relative to one another. Orthopedic fixation devices are generally machined or molded from isotropic materials, such as metals including, for example, titanium, titanium alloys, stainless steel, cobalt-chromium alloys, and tantalum.

Additionally, the primary function of an intramedullary (IM) nail is to stabilize the fracture fragments, and thereby enable load transfer across the fracture site while maintaining anatomical alignment of the bone. Although there are a large number of different commercially available intramedullary nails in the market place, there are no universal guidelines stating the conditions at which each nail will perform at its optimum for a given case. Further, the optimal degree of implant stiffness is a topic of some debate, and the mechanisms underlying the interaction between the local mechanical environment and fracture healing are generally not well known.

Further, the effect of altered fixation stiffness, in terms of torsion and bending, on fracture healing may provide insight into the pathogenesis and ideal treatment of fractures and non-unions. However, for at least cost containment reasons, similar implants are used for both simple and complex fractures. Consequently, finding a relatively optimal solution in terms of axial bending and torsional stiffness, that is closer to bone rather than titanium or stainless steel, is likely to accelerate fracture healing for a specific type of fracture.

There remains a need to provide an improved orthopedic intramedullary device for internal fixation of a bone and a method of manufacturing the same. The present invention satisfies this need and provides other benefits and advantages in a novel and unobvious manner.

BRIEF SUMMARY

An aspect of the present invention is a method for manufacturing an orthopedic device that includes forming from a medical grade powder, and via an additive manufacturing process, an additive manufactured orthopedic component. The method further includes heat treating the additive manufactured orthopedic component and machining the heat treated additive manufactured orthopedic component to form the orthopedic device.

Another aspect of the present invention is an intramedullary nail that includes a wall comprising one or more laser sintered layers of a medical grade powder. The wall has an outer portion and an inner portion, the inner portion generally defining an inner cannulated region of the intramedullary nail. The intramedullary nail further includes an internalized channel for housing a miniaturized sensor probe that extends into at least a portion of the wall. Additionally, the internal sensor probe channel does not extend through the outer portion of the wall.

Additionally, an aspect of the present invention is an intramedullary nail that has a first section coupled to a second section by a telescopic portion. The telescopic portion has an outer diameter that sized to be slidingly received in an inner region of at least one of the first and second sections to accommodate adjustments in the relative axial positions of the first and second sections. Further, the first and second sections are structure for implantation into a bone. The intramedullary nail also includes a mechanical actuator that is adapted to provide a biasing force to bias the relative axial positions of the first and second sections.

Another aspect of the present invention is an intramedullary nail that includes a wall having an outer portion and an inner portion, the inner portion generally defining an inner region of the intramedullary nail. The intramedullary nail further includes a first screw hole and a second screw hole, the first and second screw holes extending through at least the outer portion of the wall. Additionally, the intramedullary nail includes one or more protrusions in the wall between the first and second screw holes, the one or more protrusions not extending through at least the outer portion of the wall. Further, the one or more protrusions are structured to alter the torsional and flexural moduli of the intramedullary nail.

Another aspect of the present invention is an intramedullary nail having a first section having a wall, the wall generally defining an inner region of the first section. The intramedullary nail also includes a second section that is coupled to an inner section, the inner section being sized for lateral displacement in at least a portion of the inner region of the first section. Further, the inner section is selectively detachable from the first section by a locking screw to selectively alter the mechanical properties of the intramedullary nail.

BRIEF DESCRIPTION OF THE DRAWINGS

The description herein makes reference to the accompanying figures wherein like reference numerals refer to like parts throughout the several views.

FIG. 5 illustrates a comparison of example build times for 16 test bars, including interpolation of time and cost to build 280 millimeter (mm) tall intramedullary nails using different machines.

FIG. 10A illustrates a transverse section of an intramedullary nail highlighting a batch area in the wall section that is associated with a double scan strategy.

FIG. 10B illustrates uni-directional X and Y scanning associated with a double scan strategy for re-melting of laser sintered layers of a build.

FIG. 10C illustrates multi-directional X and Y scanning associated with a double scan strategy for re-melting of a laser sintered layers of a build.

FIG. 10D illustrates parameters for re-melting sintered layers of a build utilizing a double scan strategy.

FIG. 30 illustrates strength (UTS) and ductility (% Elongation) data captured from wrought and ALM Ti-64 parts.

FIG. 31 illustrates calculations for the production of 100 pieces of fully dense intramedullary nails at normal scanning speed using single, twin, and quad lasers.

FIG. 32 illustrates calculations for the production of 100 pieces of fully dense intramedullary nails at hyper-scanning speeds.

FIG. 35 illustrates a proximal end of a Trigen Meta tibial nail, and highlights the concept of boundary layer scanning.

FIG. 36A illustrates a model of an orthopedic intramedullary nail after a boundary scan and which is dimensionally adjusted to account for dimensional shrinkages.

FIG. 36B illustrates a model of an orthopedic intramedullary nail after HIPPING, which indicates a fully densified part that meets the required CAD file part specification.

FIG. 37A illustrates a photograph showing powder cores produced by 5% boundary scanning "In situ shelling".

FIG. 37B CAD illustrates a CAD file highlighting the distal extruded section used to prevent the residual powder from escaping from the core after removal form build plate.

FIG. 49 illustrates a perspective view of a distal end of a dynamizing intramedullary nail according to an illustrated embodiment of the present invention.

FIGS. 50A, 50B, and 50C illustrate dynamizing intramedullary nails having a telescopic section at a distal, midsection, and a proximal region of the intramedullary nail respectively.

FIG. 70 illustrates a table that provides a comparison between the bending and torsional stiffness of standard Trigen Meta tibial nails and a nail having a detachable inner section similar to that shown in FIG. 69.

Figure 1C:
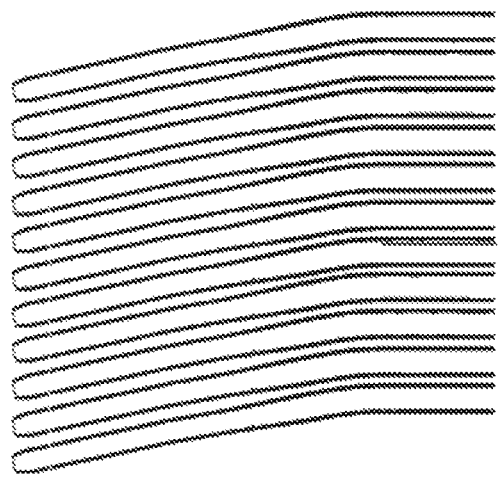
FIG. 1C illustrates a side view of a three-dimensional (3D) model of a hypothetical build program having a vertical stack of 143 nails

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DESCRIPTION OF THE ILLUSTRATED EMBODIMENTS

For the purpose of promoting an understanding of the principles of the present invention, reference will now be made to the embodiments illustrated in the drawings and specific language will be used to describe the same. It will nevertheless be understood that no limitation of the scope of the invention is hereby intended. Any alterations and further modifications in the described embodiments, and any further applications of the principles of the invention as described herein are contemplated as would normally occur to one skilled in the art to which the invention relates. The following descriptions and illustrations of non-limiting forms and embodiments of the present invention are exemplary in nature, it being understood that the descriptions and illustrations related thereto are in no way intended to limit the inventions disclosed herein and/or their applications and uses.

Orthopedic devices require certain material properties and/or tolerances for both optimal manufacturing and performance under stress loading conditions within the human body. For fixation devices, such as, for example, intramedullary (IM) nails, such properties or characteristics may include four-point bend fatigue, flexural modulus, torsional rigidity, tensile strength/ductility/yield strength, porosity, surface finishes, and geometrical tolerances/part accuracy. While traditional wrought/machined Ti-64 nails may meet current required standards, with the advent of rapid manufacturing technologies (RMT) there lies an opportunity for relatively significant reductions in both crude manufacturing and the overall cost of goods. Further, global market sales of implantable devices manufactured with titanium are estimated to reach $26 billion by 2020, which emphasizes the need for alternative manufacturing processes to meet the anticipated volumes. Further, additive manufacturing has the advantage of providing near net-shaped products/parts to multiple markets without having to rely on a highly skilled labor force. Additionally, given its design freedom, using additive manufacturing in designing and manufacturing implant devices, such as, for example, intramedullary ails, may open up the possibility of developing an implant, which is specific to the characteristics of the patient, including, for example, the patient's age, bone quality, and injury type, among other characteristics.

Figure 1B:
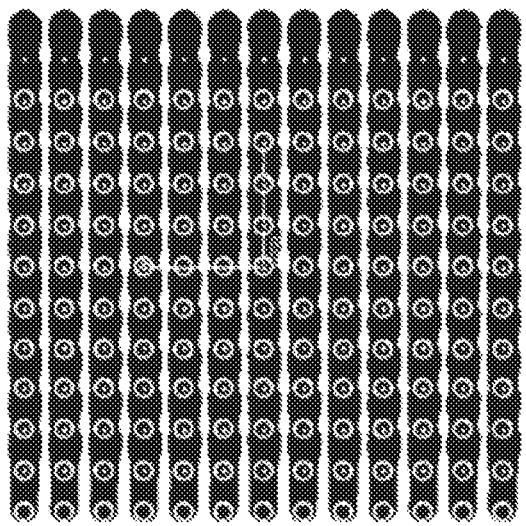
FIG. 1B illustrates a top view of a three-dimensional (3D) model of a hypothetical build program having a vertical stack of 143 nails.
Figure 1A:
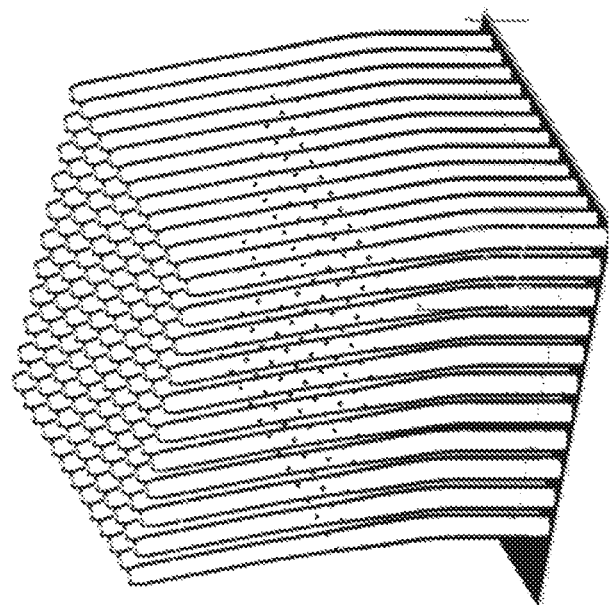
FIG. 1A illustrates an isometric view of a three-dimensional (3D) model of a hypothetical build program having a vertical stack of 143 nails.

RMT technologies include, but are not limited to, direct metal fabrication (DMF), direct metal laser sintering (DMLS), electron beam welding (EBM) and solid free-form fabrication. These technologies have been used in various industries including orthopedics for reconstructive, trauma and rehabilitation devices. In general, DMLS may use a three-dimensional (3D) computer-aided design (CAD) model, which may be created through programs, such as, for example, Magics® by Materialise® to produce a three-dimensional metal sintered model that is created layer-by-layer through irradiating metal powder with a laser. For example, FIGS. 1A-1C illustrate isometric, top, and side views, respectively, of a three-dimensional (3D) model of a hypothetical build program created by the Magic® program having a vertical stack of 143 nails across a 25 centimeter by 25 centimeter (x by y) build plate.

However, the use of DMLS can create a number of issues relating to material performance and functionality that cannot be tolerated in orthopedic devices, including porosity, part tolerance, part design, and surface finish, which require additional post-processing, each of which will be summarized in turn below.

Figure 2A:
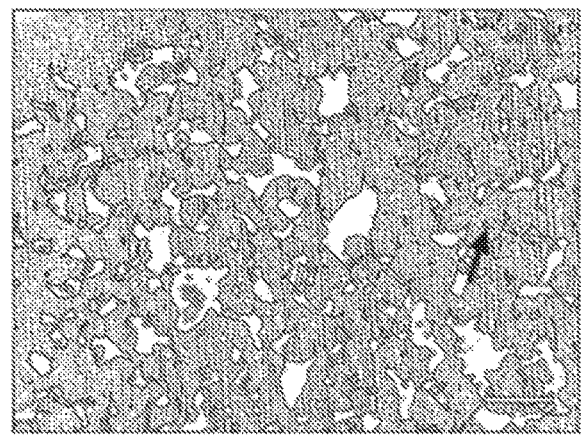
FIG. 2A illustrates a microscopic view of a distal mid-shaft location of a direct metal laser sintering (DMLS) intramedullary nail having 30% porosity.
Figure 2B:
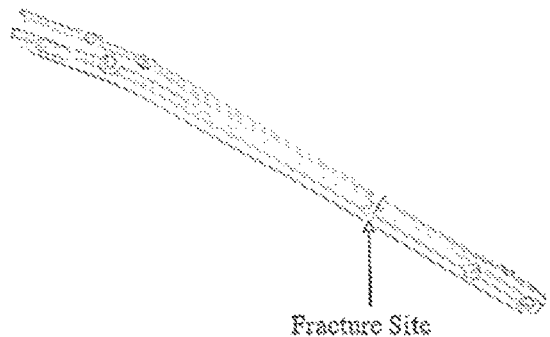
FIG. 2B illustrates a nail fracture site at a distal location of an intramedullary nail following 4 point bend fatigue testing.

(A) Porosity: Sub-optimal laser beam optics can create areas of porosity within materials that lead to poor material characteristics and subsequent poor/reduced performance. These porosity issues are typically mainly attributable to un-sintered powder within the manufactured parts and entrapment of residual gas such as argon and oxygen during sintering. For example, FIG. 2A illustrates a distal mid-shaft of a DMLS intramedullary nail with 30% porosity at a distal mid-shaft location, while FIG. 2B illustrates an associated nail fracture site at a distal location of the intramedullary nail as result of 4 point bend fatigue testing.

(B) Part Tolerance: Sub-optimal laser beams (power) can create devices with specifications outside the required tolerances. For instance, with respect to intramedullary nails, such areas that are outside required tolerances that may be produced by sub-optional laser beams include the internal/external portions of the nail, as well as areas associated with an internal screw diameter.

Figure 3A:
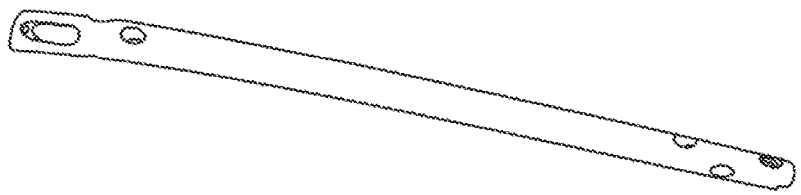
FIG. 3A illustrates an ALM nail manufactured with minimal post-machining requirements, i.e. all design features turned on in the CAD file.
Figure 3B:
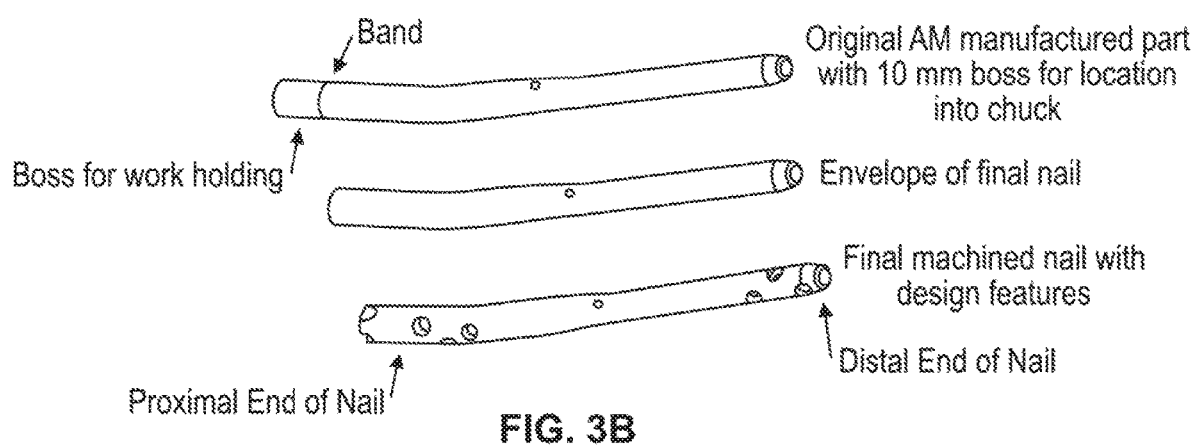
FIG. 3B illustrates an ALM nail manufactured with all design features turned off in the CAD file and a support structure for holding the part in the chuck of a CNC machine.
Figure 3C:
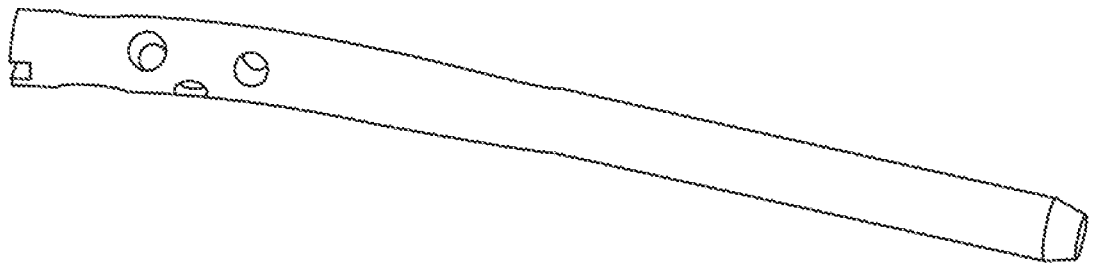
FIG. 3C illustrates an ALM nail manufactured with the design features turned off at the distal end in the CAD file.

(C) Part Design: Given the complex geometry of trauma fixation devices such as intramedullary nails, determining which design features should be turned on during the laser sintering stage is critical. Equally, identifying a suitable support structure design required to hold the part during post-processing is also critical to quality of the final part. FIG. 3A illustrates a part which has all the design features switched on during the build phase. The design features at the distal end of the part are particular sensitive to fatigue stress given that the wall is thinner. The parts are typically build in a vertical orientation and so the microstructure around the transverse screw holes are particularly prone to defects due to the nature of the heat dissipating out of the part. Consequently, this part design did not produce satisfactory mechanical fatigue properties despite requiring the least amount of post-machining. FIG. 3B outlines a more conservative design given that all the design features (transverse screw holes, key-ways slot, etc.) have been switched off during the build phase/The part is also equipped with a boss at the proximal end to secure the pare in the chuck of a CNC machine. Although this design produced satisfactory mechanical properties, the post-machining phase was very intensive. FIG. 3C outlines an implant design provides a balance between the post machining requirements and the required mechanical performance. The distal features are turned off in the most vulnerable part of the nail, which reduces the post-machining time but addresses the risk of early fatigue failure.

(D) Additional Processing: At present, the optimal post DMLS processing to impart mechanical properties is generally unknown or is sub-optimal. Techniques are known in the art such as, for example, Hot Isostatic Processing (HIP) where implants are subjected to both elevated temperature and isostatic gas pressure to consolidate and reduce porosity within materials. Shot Peening, in which implants are bombarded with shot to create plastic deformation, and re-melting of the sintered layers to reduce the porosity of the growing parts, are other strategies directed at improving part performance.

Figure 4:
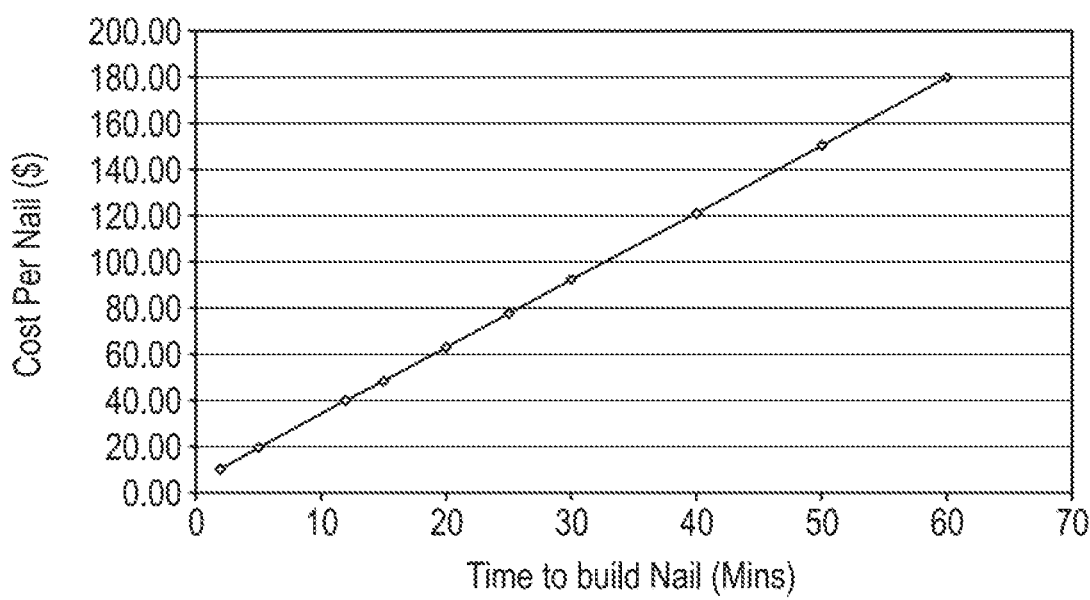
FIG. 4 illustrates the time taken to build a nail on an SLM500, which scales approximately linearly with size (length) of nail.

Additionally, the use of DMLS can create a number of issues relating to cost of goods and productivity. For example, in at least certain situations, the cost of metal powder which may be around $200-$400/kg depending on the grade of Ti-6AL4V powder purchased, e.g. Plasma Rotating Electrode Process (PREP), gas atomized, and EL1 grade 23. Further, machine cost/build time may be around $97/hour depending on the size of the manufacturing cell, the capital equipment and level of depreciation, and the staff. Additionally, part throughput, which may be 100 nails per build, can take around 109 hours to complete (65.4 minutes per nail), compared to, for example, 600 nails per day (2.4 minutes per nail), which may be attained using highly developed subtractive machining operations that are carried out in medical device manufacturing cells. The efficiency of the additive manufacturing process can be improved using a laser sintering machine with a bigger footprint and equipped with 4 scanners, e.g. SLM 500 quad scanner. 800 nails (sized 20 cm long .times.10 mm OD) can be built in 160 hrs. equating to 12 minutes per nail using boundary scanning "in situ shelling" strategy. The SLM500 is capable of producing around 40,000 nails per year, if run to full capacity and adopting the boundary scanning strategy. If the supply of atomized powder costed at £30/Kg can be used in preference to material supplied from a powder supplier (typically $250-400/Kg), the average cost per nail can approach $120 per part. FIG. 4 illustrates the time taken to build a nail on an SLM500, which scales approximately linearly with size (length) of the nail. For example, the 320 mm nail requires an average per nail build time of 25 minutes, FIG. 4.

The cost of metal powder is typically controlled by suppliers who may charge a premium given the limited number of suppliers available in certain market places. For example, European supply companies, and more specifically UK suppliers, often offer radically cheaper and environmentally benign powder compared with existing titanium production methods, such as, for example, the energy-intensive gas-atomized and toxic Kroll process, which constitutes a costly and labor-intensive four-step process. Such suppliers may take rutile and transform it directly into powdered titanium using electrolysis, which is cost-effective and thus generally essential to the supply chain. The low-cost titanium powder can be used in a variety of new applications, whereas previously the metal has been excessively expensive for use in mass production of lower value items. For example, gas atomized powder directly from bar stock is a potential route for reducing Ti-64 power cost to around £30/Kg.

FIG. 5 illustrates an example of comparison of build times for 16 test bars, including interpolation to time and cost to build 280 millimeter (mm) tall intramedullary nails using different machines, identified as Arcam S12, Concept M2, EOS M270, Realizer, Renishaw AM250, and SLM Solutions 280HL. Build time of parts may be influenced by a number of inter-related variables, including, for example, DMLS machine specification, as well as operating costs, such as, for example, gas, electricity, and capital equipment, among other costs, as shown in the illustrated example table depicted in FIG. 5. Although there may be a relatively significant scope to reduce the cost of part manufacture, it does not necessarily compare well with the cost of machining these parts, negating the need for other cost reduction strategies such as part design, scanning speed and scanning pattern.

The present invention provides an optimal DMLS manufacturing route for orthopedic devices with material performances matching those for wrought/cast/machined titanium parts.

In one form of the present invention, a method of manufacturing an elongated orthopedic device via direct laser sintering is provided including the steps of: a) producing a virtual three-dimensional (3D) elongated device model; b) manufacturing an elongated device in an appropriate build direction via direct metal sintering according to the three-dimensional (3D) model utilizing a laser power of at least 300 Watts (W), and using a powder of at least Grade 5 quality, such as, for example, a TiAl6v4 powder; c) subjecting the elongated device to Hot Isostatically Pressing (HIP) utilizing a temperature of at least 1000 degrees with a cooling rate of between 0.24 and 72 degrees C. min−1; d) machining and polishing the HIP processed elongated device; and e) wherein the mechanical performance is equivalent to the four-point bend performance of wrought titanium.

In another form of the present invention, an orthopedic implant such as, for example, an intramedullary nail, is manufactured via the following steps and processes:

(A) Creation of a CAD File: An appropriate file type, such as, for example, a .stl formatted file, is uploaded into a three-dimensional (3D) software provider such as, for example, Magics® by Materialise®, among others, in an orientation that is suitable for manufacturing. Such files may include, for example, a non-supported vertical build structure of an intramedullary (IM) nail, among other components or devices.

Figure 6A:
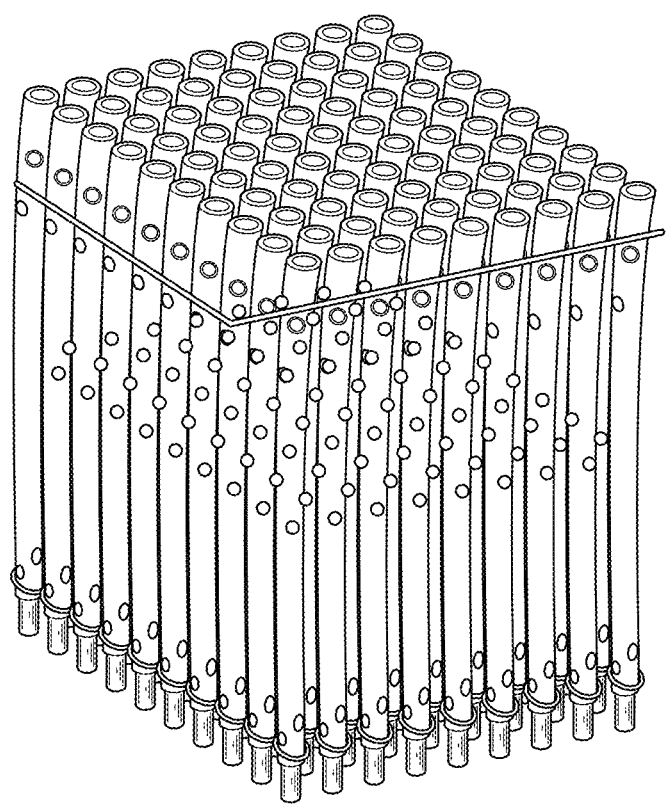
FIG. 6A illustrates a perspective view of the manufacture of intramedullary nails using a vertical orientation.
Figure 6B:
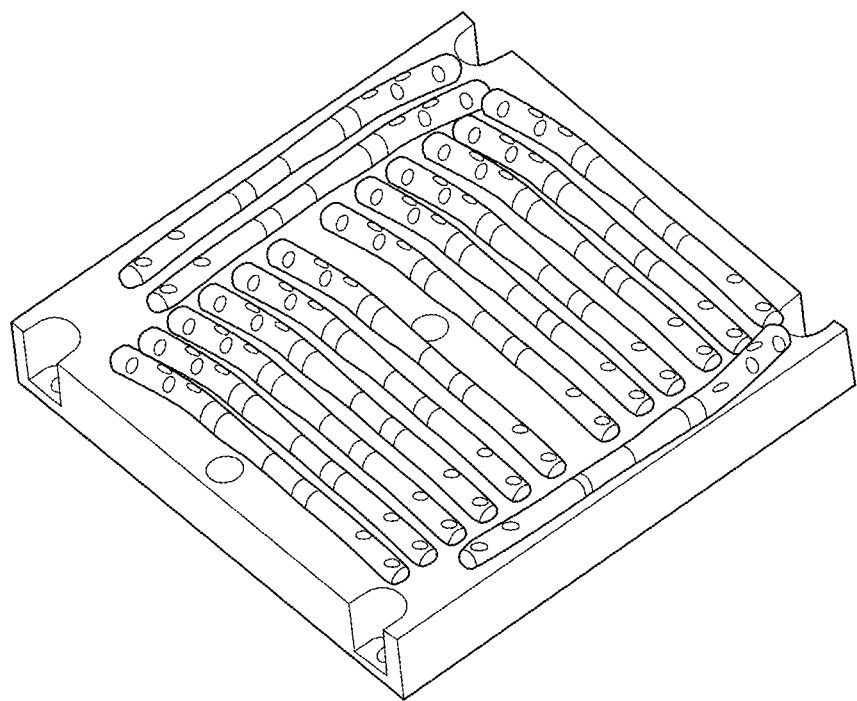
FIG. 6B illustrates a perspective view of the manufacture of intramedullary nails using a horizontal orientation.

(B) Build Orientation: The parts can be built in a multitude of build orientations from 0 to 90 degrees, which will produce anisotropic physical properties that are sensitive to mechanical loading. They can also be built with or without the use of custom-designed support structures to assist with the post machining process, FIG. 3b. Further, building the parts, such as, for example, intramedullary nails vertically using an additive layer machine ("ALM") equipped with soft re-coaters and without any support structures may reduce the burden of post-machining. For example, FIGS. 6A and 6B illustrate a three-dimensional (3D) CAD file highlighting the manufacture of intramedullary nails using a vertical orientation (FIG. 6A) and a horizontal orientation (FIG. 6B), with the vertical and horizontal orientations amendable to ALM with soft and hard re-coaters, respectively. FIG. 6A illustrates building parts in a vertical configuration/orientation, and can be made more economical by designing supports structures that allow the parts to be stacked in layers. FIG. 6B illustrates building parts in a configuration/orientation at an angle between 0 and 90 degrees, and can facilitate reducing their anisotropic behavior. However, lower numbers of devices can be made in a single build run.

(C) Design Optimization: RMT can be used to give significant design freedom regarding the internal geometry (FIG. 5A-5D) and the external geometry (FIG. 6) of the intramedullary nails to modify nail characteristics such as, for example, torsional/bending stiffness which is difficult to achieve with conventional manufacturing methods. Specifically, FIGS. 7A-7D illustrate three-dimensional (3D) CAD intramedullary nail models in cross-section and which highlight a tapered wall section (FIG. 7A), a porous inner structure (FIG. 7B), a detachable inner section (FIG. 7C), and an internal fluted section (FIG. 7D). Additionally, FIG. 8 illustrates examples of optimal cross-sectional geometries for an intramedullary nail, wherein: A=Solid Schneider, B=Diamond, C=Sampson Fluted, D=Kuntscher, E=Rush, F=Ender, G=Mondy, H=Halloran, I=Huckstep, J=AO/ASIF, K=Grosse-Kempf, L=Russell Taylor, and M=Trigen. At least some of these nail geometries may have a cross-section designed to reduce stiffness or reduce intramedullary pressures. Additionally, the diversity of these nails ranges from classical Kuntscher nails (D), which may be tight fitting, reamed, no locking, to Universal nails (K), which include the use of interlocking screws.

RMT can also be used to produce patient matched implants through optimization of the curvature of the intramedullary nail. This may avoid a mismatch in the radius of curvature between the intramedullary nail and the bone, particular the distal femur, which could otherwise lead to anterior cortical perforation. For example, the radius of curvature of the femur is estimated to be 120 cm (+/−36 cm). Yet, femoral nail designs typically have less curvature, with a radius ranging from 186 to 300 cm. Additionally, nails can also be designed to suit each individual fracture. According to such an embodiment, a computer model of each individual fracture can be created, and this model can then be used to test different fixation strategies in order to select a system that will create a specific mechanical environment for assumed load-bearing requirements.

(D) Selection of Three-Dimensional (3D) Printer: The intramedullary nails can be built using various commercial machines from suppliers such as, for example, SLM Solutions, Renishaw, Realizer, EOS, Concept Laser and Arcam. The relative merits of each technology are generally based upon: (a) machine productivity (i.e., size of the chamber (along the x, y, and z axes), scanning speed, and number of lasers); (b) part quality (i.e., accuracy, surface finish, tolerances/resolution); and (c) capital and running costs (e.g., consumption of gas and electricity).

(E) Laser Sintering: Hard re-coaters, such as, for example, the EOS M270/M280/M290 from EOS, may produce parts with superior mechanical properties and reduced porosity given that any weakly-bound, partially sintered material is more likely to be removed at each build layer. Soft re-coaters may produce parts that may also be contaminated with silicone blade debris, which would in turn need to be investigated to satisfy regulations. The soft re-coater blades can potentially wear out after one build, which in turn adds additional cost to the manufacturing process. Hard re-coater blades can be made from high speed steel, and the debris released from these arms into the part is perceived to be less of a problem than soft re-coater blades. Hard re-coater blades are also more economical as to powder use. Modern laser sintering machines supplied by SLM Realizer can produced focused beam spot sizes of 30 microns, which can produce parts with superior grain structure and resolution that enables novel design features to be realized, e.g. internalized channels.

(F) Powder Specification: Medical grade Ti-64 powder is available in a number of different formats depending on the end application and the selection of the three-dimensional (3D) printer. Grade 5 gas or plasma atomized powders are typically used in laser sintering, may have a particle size range of either 15 to 45 microns (μm) or 20 to 63 microns (μm), and are typically supplied at a cost of £150/kilogram. Grade 23 ELI powder may be either a gas-atomized or centrifugal PREP powder with a particle size range of between 45 and 100 microns (μm), and is typically supplied at £250/kilogram, and may contain reduced levels of oxygen, nitrogen, carbon and/or iron. Making a decision to switch to virgin powder for subsequent builds, or utilizing unused powder from previous builds, can be determined from QA testing of the built parts and the powder bed. Clearly, building parts from unused powder left over from previous builds will reduce the cost burden and demand for purchasing several tons of powder to cover the manufacture of large quantities of intramedullary nails (i.e., 10,000 or more).

Figure 9:
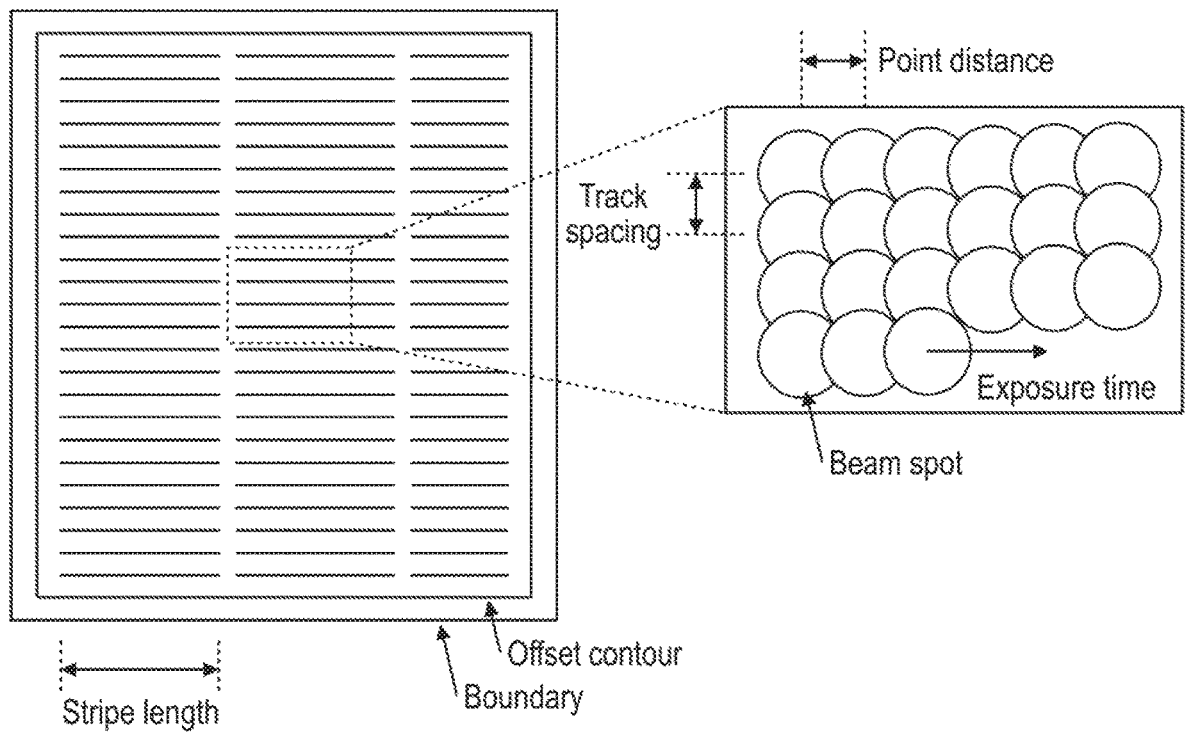
FIG. 9 illustrates a schematic representation of last sintering additive manufacturing process parameters, layer by layer, reproduced from a build carried out on a Renishaw SLM250.

(G) Selection of Build Parameters: Build parameters selected for additive manufacturing techniques, including selective layer melting (SLM), laser sintering, and e-beam processing, among other techniques, in the production of an intramedullary nail, may be unique to the brand or manufacturer of the equipment used to perform the additive manufacturing. For example, laser sintering or e-beam processing of Ti-64, may be unique to the machine suppliers. Moreover, FIG. 9 provides a schematic diagram of build parameters that may be used for a Renishaw SLM250 to produce intramedullary nails. Specifically, FIG. 9 is a schematic representation of laser sintering additive manufacturing process parameters, layer by layer, reproduced from a build carried out on a Renishaw SLM250, wherein the laser power is between 50 watts (W) and 280 watts (W), the point distance is between 30 and 90 microns (μm), the hatch distance is 65 microns (μm), the layer thickness if 50 microns (μm), and the exposure (Ex) is 50 to 500 microseconds (μs).

With regard to scanning strategy, although certain additive manufacturing techniques, such as selective layer melting (SLM), are capable of producing fully dense materials, it may be necessary or beneficial to use one or more of the following scanning strategies to reduce part porosity:

(1) Layer Re-melt: As illustrated in FIGS. 10A-10D, re-melting of the laser sintered layers may help reduce the porosity of the growing parts using a double scan strategy. Further, the variable focusing optic in some systems, such as, for example, in the 1 kilowatt (kW) SLM Renishaw SLM250 system, may enable the use of high laser powers at relatively slow speeds, with relatively large spot sizes at the center of the layer compensating for the high heat losses. Further, high laser powers at relatively high speeds can be utilized at the surface areas (i.e., boundaries of the layer) in order to achieve high surface quality. FIG. 10A illustrates a transverse section of an intramedullary nail highlighting the hatch area in the wall section of the intramedullary nail associated with a double scan strategy. FIG. 10B illustrates uni-directional X and Y scanning (i.e., directions are parallel with one another), and FIG. 10C illustrates multi-directional X and Y scanning (i.e., directions are arranged transverse to one another at, for example, 90 degrees). FIG. 10D illustrates parameters used in the re-melting of the layers utilizing a double scan strategy.

Figure 11A:
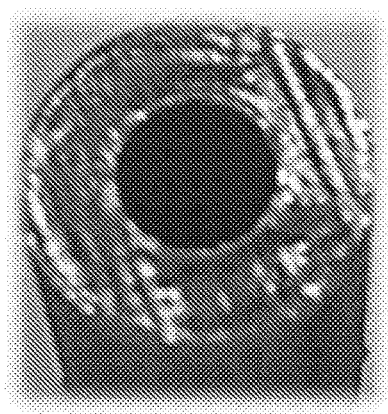
FIG. 11A illustrates a transverse section of an intramedullary nail highlighting a wall section of the intramedullary nail that is associated with an X and Y alternating hatch laser raster for a double scan strategy for re-melting of laser sintered layers of a build.
Figure 11B:
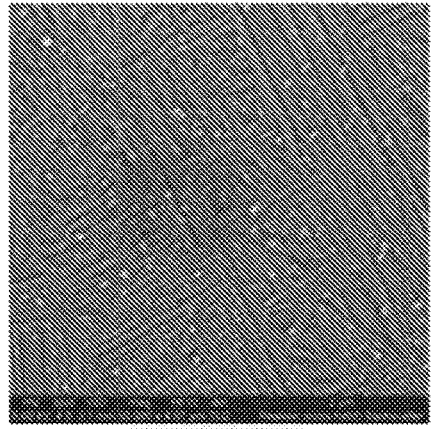
FIG. 11B illustrates X and Y alternating hatch laser raster associated with a double scan strategy for re-melting of laser sintered layers of a build.
Figure 11C:
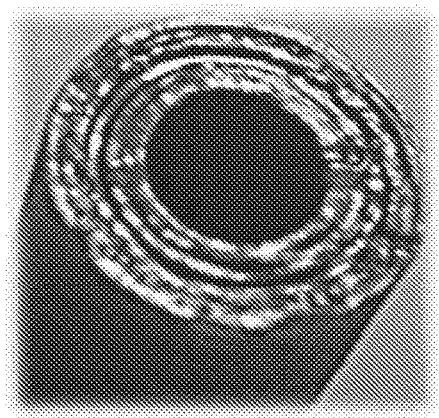
FIG. 11C illustrates a transverse section of an intramedullary nail highlighting a wall section of the intramedullary nail that is associated with a circumferential laser raster for a double scan strategy for re-melting of laser sintered layers of a build.
Figure 11D:
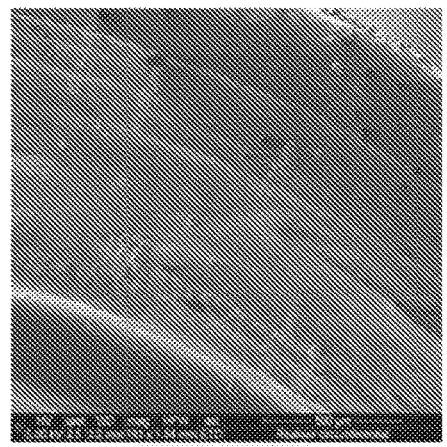
FIG. 11D illustrates circumferential laser raster associated with a double scan strategy for re-melting of laser sintered layers of a build.

(2) Alternative Scanning: As illustrated in FIGS. 11A-11D, alternative scanning strategies may be implemented, such as, for example, via use of a Realiser SLM100 system. Such alternative scanning strategies may include an X and Y alternating hatch laser raster, as illustrated in FIGS. 11A and 11B, and a circumferential laser raster, as shown in FIGS. 11C and 11D.

(3) In-Line Monitoring: Ultra-low oxygen content may be maintained in the build atmosphere. An oxygen concentration below 50 parts per million may be crucial when processing reactive materials, and may contribute relatively significantly to material integrity and mechanical performance. With regard to a real-time melt pool monitoring system, SLM and e-beam qualification through the creation of a database that may include a variety of information, such as, for example, laser power, scan strategy, match strategy, among other information that may describe the effect of process part parameters on resultant mechanical properties of the built part, such as the built intramedullary nail.

(H) Post-Processing of RMT Parts: Post-processing of RMT parts may include, but is not limited to the following steps or processes.

(I) Heat Treatment: Heat treating the parts that are built via an additive manufacturing process can involve any combination of the steps of HIPPING (Hot Isostatically Pressed System), stress relief, and annealing, among other steps.

(a) HIPPING: a hot isostatic pressing (HIP) may be employed to reduce the porosity of metals and improve the mechanical properties and workability of the material. HIPPING may include the following steps:

(1) Evacuation/Purge (e.g., 3 times to below 15 mb);

(2) Sustain Temperature: a typical HIP temperature may be, for example, between approximately 920° Celsius and approximately 1000° Celsius, and optimum temperature may be approximately 980° Celsius+/10° Celsius. If the HIP temperature is above 1000° Celsius, the additive manufactured parts may become contaminated with nickel given that HIPPING furniture is typically made from Nickel-based alloys. This may be more evident at HIP temperatures approaching 1050° Celsius. This could in turn be mitigated by either (a) wrapping the parts in titanium (Ti) foil, (b) standing the parts on either recrystallized alumina plates or boxes so that the titanium (Ti) cannot make contact with the nickel (Ni) based load plates, or (c) laying the wrapped parts on a saffil blanket;

(3) Sustain Pressure (MPa): such as, for example, a pressure during a least a portion of the HIP process of 103 MPa+/−5 MPa;

(4) Sustain Time (minutes): such as, for example, a sustain time of 120 minutes+15/−0 minutes for the HIP process;

(5) Cooling Rate (° Celsius/minute): for example, less than 10° Celsius/minute; and (6) Heating Rate (° Celsius/minute): for example, less than 10° Celsius/minute.

(b) Stress Relieving Procedure: Stress relieving may be done in a stress relieving furnace under argon atmosphere or in a vacuum furnace. A stress relieving process may involve one or more of the following steps, among other steps:

(1) Ramp up in 60 minutes the temperature of the additive manufactured built part to an elevated temperature, such as, for example, a temperature of about 800° Celsius, in a Centorr vacuum furnace;

(2) Hold the elevated temperature of the additive manufactured built part a predetermined time period, such as, for example, for around 2 hours; and (3) Power off the furnace heating power and open the furnace door when the temperature of the additive manufactured built part drops down to a set cooled temperature, such as, for example, a temperature of approximately 400° Celsius. The maximum cooling rate to reduce the temperature of the additive manufactured built part from the elevated temperature to the set cooled temperature may be, but is not limited to, 55° Celsius/minute, while the cooling rate from the set cooled temperature of about 100° Celsius, may be slower, such as, for example, about 35° Celsius/minute.

(c) Annealing: An annealing process may involve the following steps:

(1) Heat the additive manufactured built part at an annealing temperature, such as, for example, approximately 1000° Celsius for a dell time of 2 hours in an argon inert atmosphere. This temperature exceeds the β transus temperature of 995° C. for Ti-64 alloy; and (2) Nitrogen quench to room temperature. Note that the 1000° Celsius heat treatment may be for taking the alpha phase into solution and fully sintering adjacent powder that may have only been partially sintered to the component.

(2) Machining Operations: The surface improvement techniques outlined below for the external and internal geometries of the additive manufactured built part may provide a finished surface that improves mechanical performance, and reduces the risk of bacterial contamination by eliminating surface negatives commonly inherent on most machined surfaces. The removal of sharp edges from the additive manufactured built part also may help contribute to a much smoother, less destructive introduction into the human body were tissues could otherwise be damaged or traumatized by sharp edges and the like.

(a) Machining Operations—External Geometry: The following optional surface finishing steps can be used to remove the alpha case from the external surface of the additive manufactured built part, which is typical of three-dimensional (3D) printed Ti-64 parts. The surface finishing operations may also help flatten out the surface meeting, improve part accuracy, and introduce a compressive layer into the first 0.2 millimeters (mm) of the surface.

(1) Removal of Alpha Case Layer via Grit Blasting: The alpha case layer is removed, which may be approximately 30 microns deep although not necessarily uniform. The alpha case layer can be removed in a variety of different manners, including using mechanical abrasion methods in the form of aluminum oxide media. This step can be carried out manually based on experience to observe the sparks created by the alpha case to help determine when the substrate has been breached (i.e., the sparks will be extinguished when the alpha case has been removed). In a production environment, an automated set may be established, which could in turn give a more uniform metal removal. Mechanical removal has the advantage of helping to prepare the surface for subsequent operations, as well being a lower cost option over chemical milling. Maintaining the geometry of the additive manufactured built part may also provide some challenges as the material removal rate between the alpha case and the substrate will vary considerably. This approach can be used to attack both the outside and inside surfaces of the intramedullary nail. The loss of material from this step (typically 0.2 microns (μm)) would be factored into the outside diameter (OD) and inside diameter (ID) of the build the additive manufactured built part and/or the associated model of the CAD file.

(2) Vibratory Polishing: Depending on the surface condition post-blasting, the parts may need to be rough polished to remove or truncate peaks prior to peening. This step may ensure that the peening process compresses the entire surface without risk of folding over surface asperities which would otherwise create stress raisers.

Figure 12:
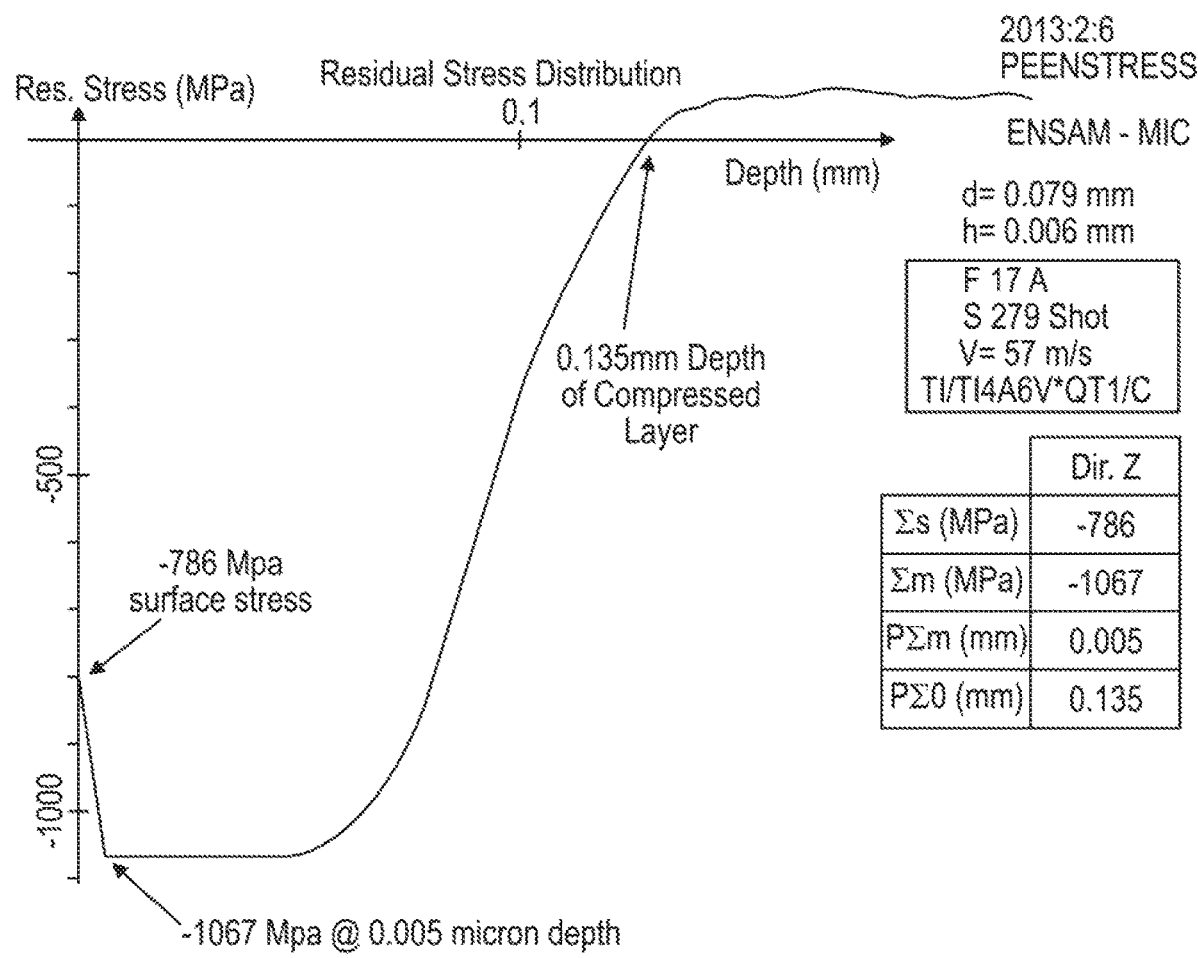
FIG. 12 illustrates peen stress distribution for a Ti-64 additive layer machined ("ALM") part.

(3) Creation of a Compressive Layer of Residual Stress: Following removal of the alpha case layer and preparation of the surface, shot peening parameters would be specified to induce an optimum layer of compressive residual stress with a maximum magnitude of between approximately 800-1000 mega Pascal (MPa), and a depth of around 0.2 millimeters (mm). FIG. 12 illustrates that the compressive layer will have a refined grain structure and will effectively delay the initiation and propagation of fatigue cracks. Specifically, FIG. 12 illustrates a typical peen stress distribution curve for a Ti-64 ALM part. Peening of the sample surface has the effect of increasing the surface hardness, as well as introducing the beneficial compressive residual stress that lowers the tensile stress felt at the surface.

(b) Machining Operations—Internal Geometry: The following optional surface finishing steps can be used to finish the internal surface of the part.

(1) Extrude Honing: Extrude Honing is an interior surface finishing process characterized by flowing an abrasive-laden fluid through a work piece, which effectively performs erosion. This fluid is typically very viscous, and has the consistency of putty or dough. It may specifically be used to remove burrs, polish surfaces, form radii, and even remove material. The nature of AFM makes it ideal for interior surfaces of an intramedullary nail, slots, holes, cavities, and other areas that may be difficult to reach with other polishing or grinding processes.

In another form of the present invention, manufacturing of an orthopedic implant may utilize optimal processing conditions during formation of the part. In one embodiment, manufacturing of an orthopedic implant includes optimized fatigue performance of three-dimensional (3D) printed Ti-64 parts.

(A) Laser Power: The mechanical properties of additive manufactured parts may be dependent upon how much power is used to build them, such as, for example, the energy density of the laser beam that was used to produce the parts. As a general rule, the greater the energy density used to manufacture the part, the rougher the part surface finish will be. This phenomenon may be caused by heat from the part "leaking" into the surrounding powder material and encouraging the powder to fuse to the surface of the part. Therefore, increasing the energy density of the laser beam may increase the surface roughness and the overall strength or the parts.

Figure 13:
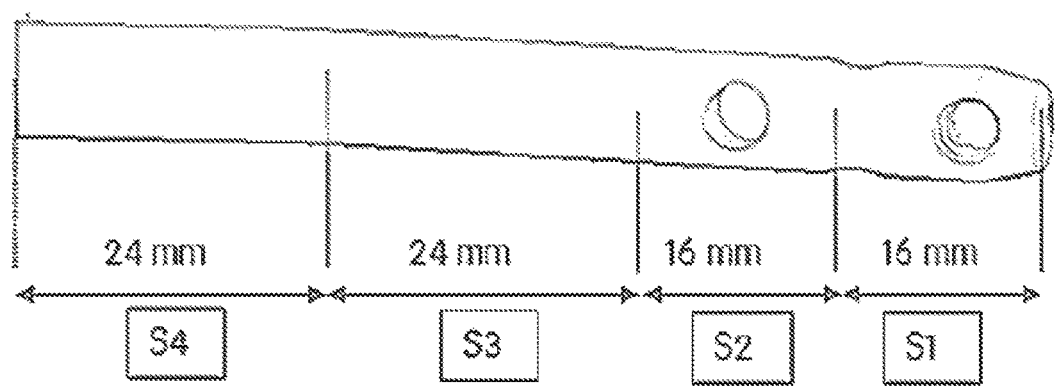
FIG. 13 illustrates a three-dimensional model of an ALM test part with attempts to clone a distal end of a standard intramedullary nail.

For example, a batch of twelve (12) additive manufactured Ti-64 samples resembling the distal section of a tibial nail was formed via laser sintering. The following processing conditions were implemented using a Renishaw 250 ALM: (a) scanning speed of 150 millimeters/second (mm/s); (b) focus offset of 0 millimeters (mm); (c) a point distance of 65 microns (μm); (d) an exposure time of 250 μs; and, (e) a laser power varied between 120 watts (W) and 400 watts (W). Such processing included, and provided related information regarding, the following:

(1) Metallography: The twelve ALM samples were exposed to varying laser powers of 120 W, 160 W, 200 W, 240 W, 280 W, and 350 W before being submitted for axial sectioning into four parts (S1-S4 (FIG. 13); distal to proximal), and subsequent metallurgical investigation was used according to the schematic representative illustrated in FIG. 13. Specifically, FIG. 13 illustrates a three-dimensional (3D) model of the LM test part which attempts to clone the distal end of a standard intramedullary nail.

Figure 14:
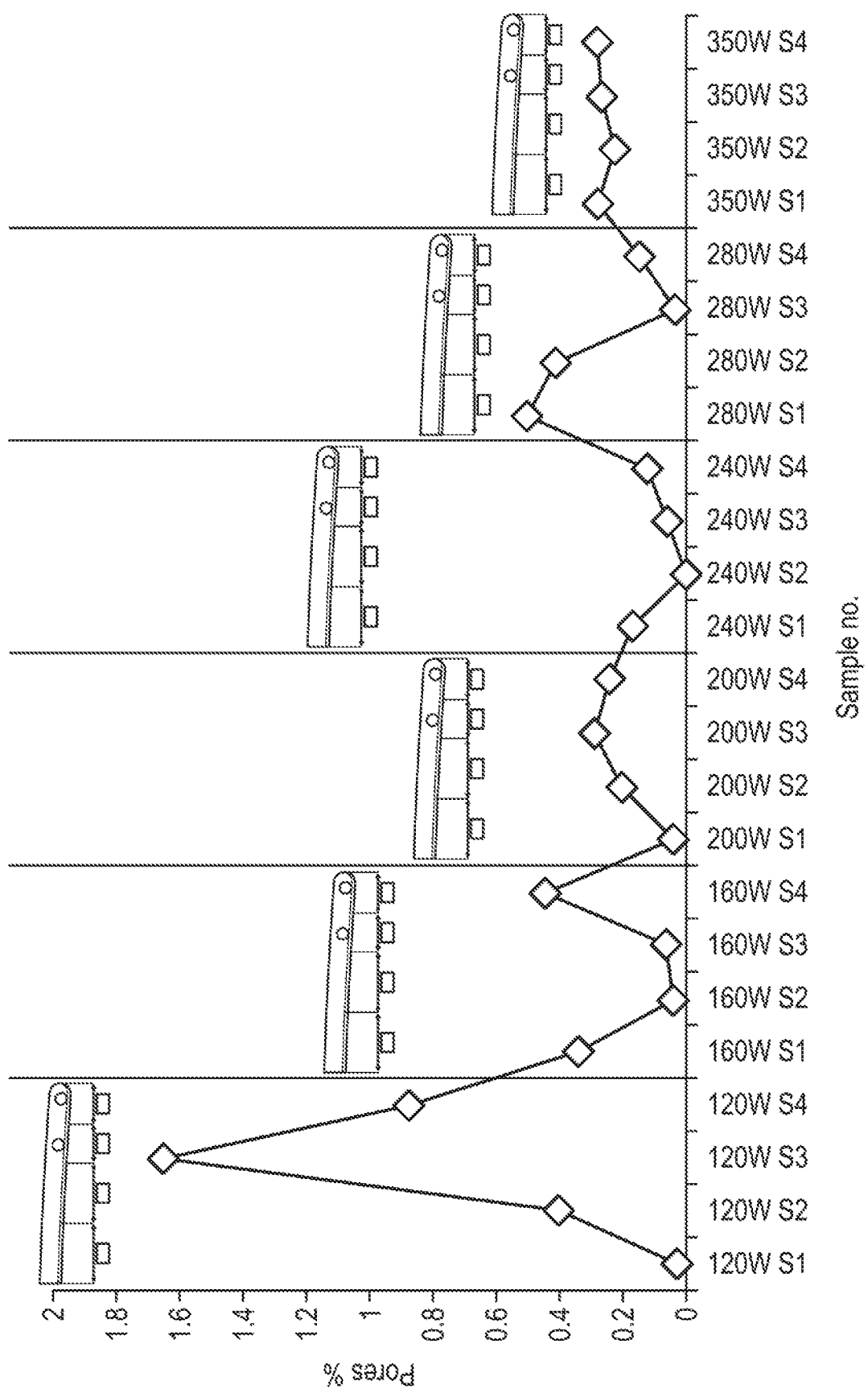
FIG. 14 illustrates an example of the effect of laser power on porosity as a function of position along an ALM sample.

After cutting, the sections Ti-6Al-4V ALM samples ere cold mounted in acrylic resin and polished with SiC paper (80, 220, 800, 1200, 2400 grit) to 1 micron. Porosity in the wall section of the samples was measured from scanning electron microscope (SEM) images using standard image analysis software. The degree of porosity for each sectioned sample was determined in the wall section from SEM images captured using image analysis software. The results of the study are summarized in FIG. 14, which illustrates an example of the effect of laser power on porosity as a function of positive along the ALM sample (S1 to S4 (FIG. 13)). Porosity ranged between 0.03% and 1.7% in the wall section, and tended to be highest towards the proximal end of the specimen (S4). In general, porosity decreased relative to increasing laser power, thereby implying improved consolidation of the powdered structure.

Figures 15, 16:
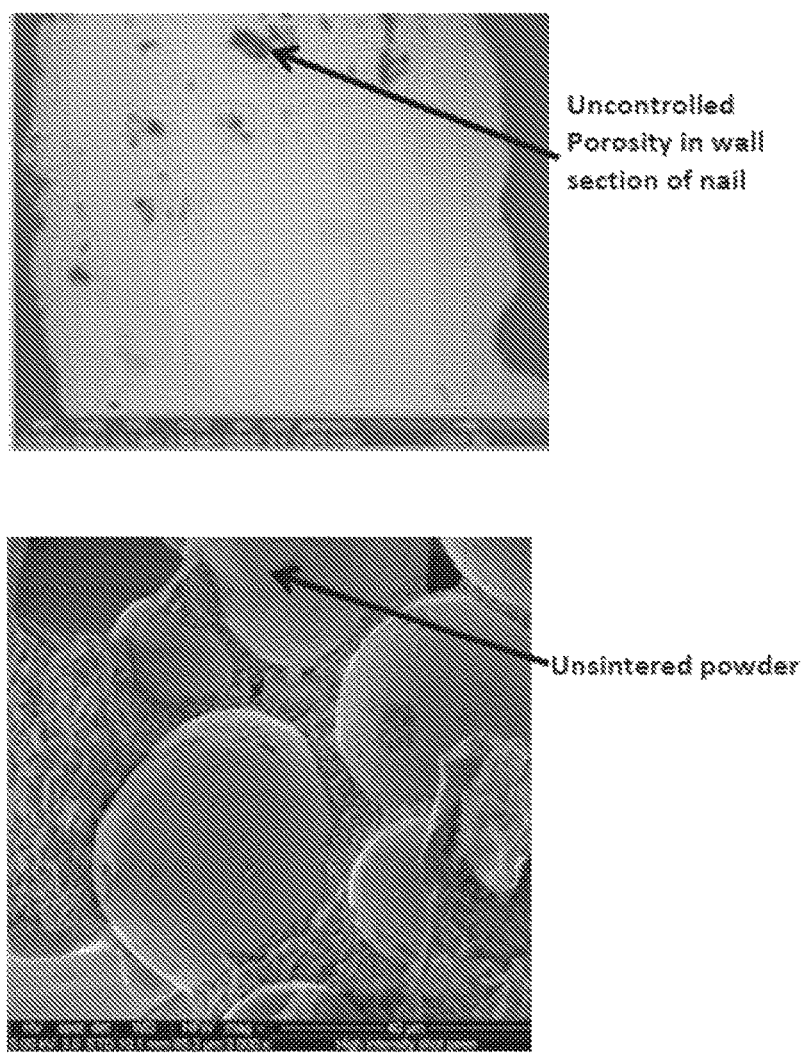
FIG. 15 illustrates an SEM image captured from a fracture surface of an ALM part laser sintered to 400 Watts (W).
FIG. 16 illustrates a table depicting results of four-point bend testing conducted at 5 hertz (Hz). A machine Ti 6-4 nail was cut to a similar length and tested using the 300 to 3000 Newton (N) method to validate the use of the test rig with short nails. The nail survived $10^6$ cycles with no sign of damage and did not move on the test rig. The ALM samples were tested using the same method but using 200 to 2000 Newton (N) loading conditions.

An SEM image captured from the fracture surface of an ALM part laser sintered to 400 watts (W) is illustrated in FIG. 15, which is characteristic of both ductile and brittle failure. This in turn indicates that there is some porosity in the core structure combined with some un-sintered powder. Specifically, FIG. 15 illustrates an SEM image captured from the fracture surface of an ALM part laser sintered to 400 watts (W). The morphology is mainly ductile, but deformation is quite poor around pre-existing cracks because of the relatively poor work hardenability of the alloy.

Figures 17, 18:
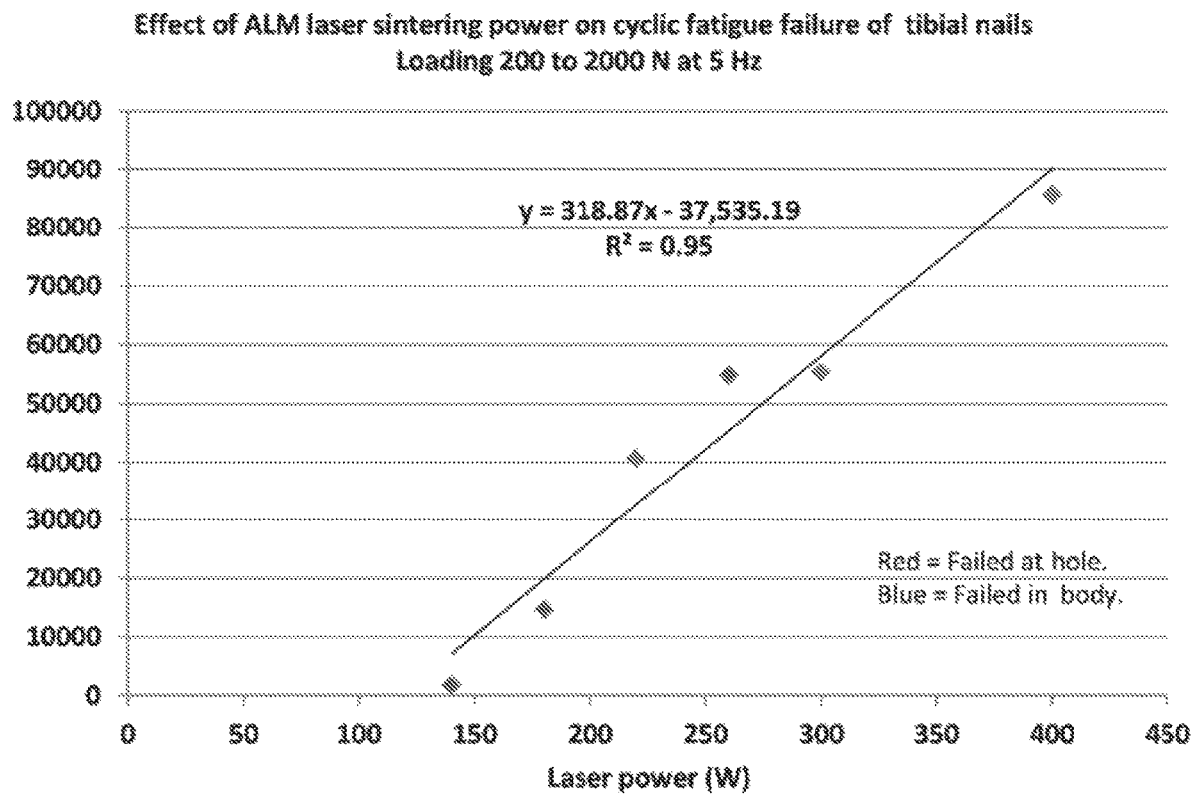
FIG. 17 illustrates the effect of laser power on four-point bend fatigue properties to Ti-64 ALM parts conducted at step load of 2000:200 Newton's (N) at 5 hertz (Hz).
FIG. 18 provides a table of a listing of example machine suppliers for laser sintering and electron beam melting of Ti-64 material.

(2) Four-Point Bending Test: ASTM test method (P1264-03) was consulted on the four-point bending fatigue testing method for intramedullary fixation devices. The samples that were exposed to varying laser powers of 140 W, 180 W, 220 W, 260 W, 300 W, and 400 W were submitted for four-point bend cyclic fatigue testing. Two loading conditions were used, namely, 200 newton (N) to 2000 newton (N), and 300 newton (N) to 3000 newton (N). Additionally, a machined Ti-64 nail was cut to a similar length (77.04 mm) to the shortest sample nail and tested using the 300 newton (N) to 3000 newton (N) method to validate the use of the test rig with relatively short nails. The machined Ti-64 nail survived $10^6$ cycles with no sign of damage and did not move on the test rig. The ALM samples were tested using the same method by using the 200 newton (N) to 2000 newton (N) loading conditions. The number of cycles to failure for each sample was recorded, and the samples were photographed to record the failure mode. In all cases, the length/diameter (L:D) ratio was fixed at 7:1, and all tests were conducted at 5 hertz (Hz). The test results are summarized in FIGS. 14 and 15, with FIG. 16 illustrating the summarized test results conducted at 5 Hz, and FIG. 17 illustrating the effect of laser power on four-point bend fatigue properties of Ti-64 ALM parts conducted at step load of 2000:200 newton (N) at 5 hertz (Hz).

Figure 19A:
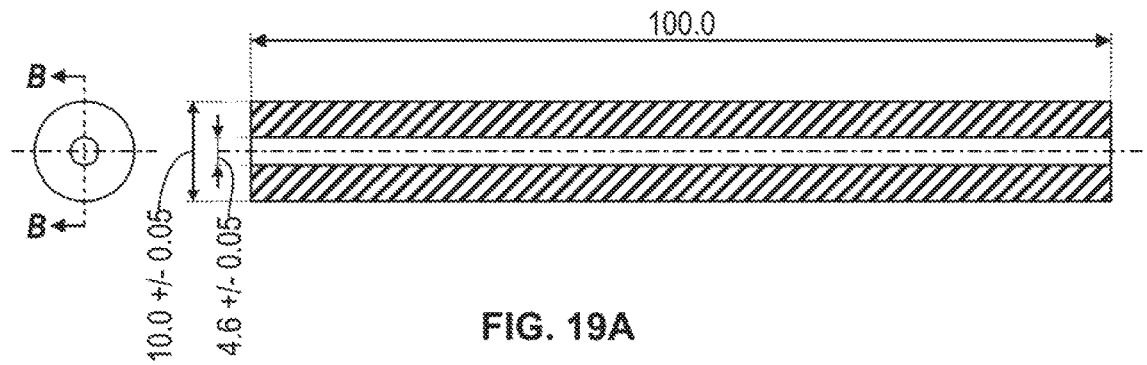
FIG. 19A illustrates a 2D drawing of a simplified test coupon geometry.
Figure 19B:
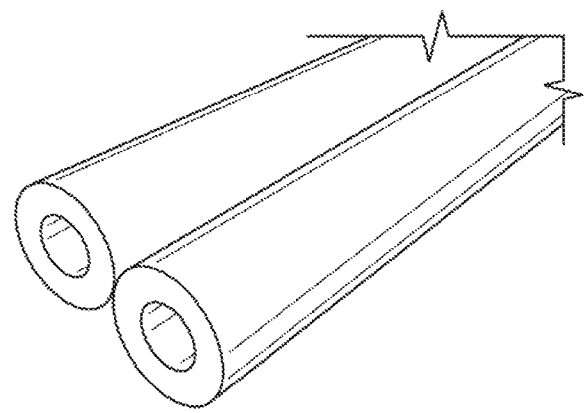
FIG. 19B Photograph of the cannulated Ti-64 coupons post-machining/heat treatment.
Figure 20:
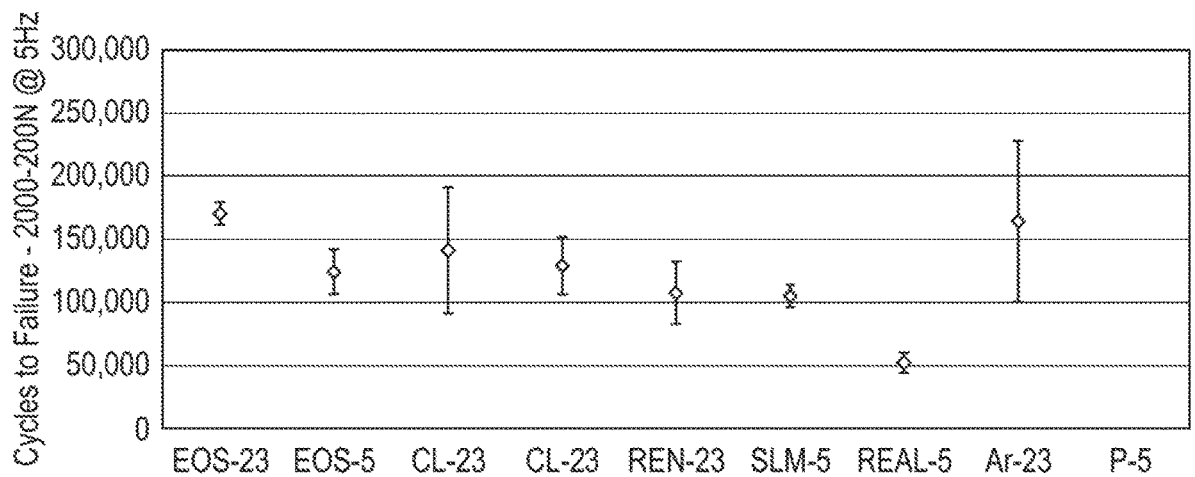
FIG. 20 illustrates four-point bend fatigue performance of laser sintered and e-beam melted coupons as a function of machine suppliers. Tests conducted at 200 to 2000 Newton's at 5 Hertz (Hz).

(B) Standard Fatigue Performance of Laser Sintered and E-beam Melted Coupons: In order to determine whether there is any accrued benefit in using a particular machine supplier to build Ti-64 nails, as listed in FIG. 18, a part geometry may be created that is related to the final device, which in turn allows direct comparisons to be made. Specifically, FIG. 18 lists machine suppliers identified for laser sintering and electron beam melting of Ti-64 material, and FIG. 19A illustrates a 2D drawing of simplified test coupon geometry. FIG. 19B illustrates a photohrao of a simplified test coupon geometry When the ALM Ti-64 coupons outlined in FIG. 19 made the different machine suppliers are tested in four-point bend fatigue in the "as-built condition," they tend to fail at around 125 k cycles, as illustrated in FIG. 20. In contrast, wrought metal of the same geometry can run out to 1M cycles when loaded at 4000 newton (N) to 400 Newton (N) at 5 hertz (Hz) When these ALM Ti-64 coupons are scrutinized under the microscope, they are found to be highly porous, exhibit a rough surface, and have a sub-optimal microstructure. More specifically, FIG. 20 illustrates four-point bend fatigue performance of laser sintered and e-beam melted Ti-64 coupons as a function of machine suppliers. Part geometry: –100 millimeter (mm) long by 10 millimeter (mm) outer diameter OD and 4.7 millimeter (mm) inner diameter); test conditions: –2000 newton (N) to 200 newton (N) at 5 hertz (Hz) according to ASTM 1264. Such testing indicates that the mean performance of the laser sintered and e-beam melted coupons is approximately 125 k cycles to failure.

Figure 21A:
FIGS. 21A and 21B illustrate micro sections of an EOS sample at different magnifications, and etched with Kroll's reagent to visualize the grain structure.
Figure 21B:

Referring to FIGS. 21A and 21B, illustrated therein is a typical crystal structure of a laser sintered Ti-64 part comprised of bands $\beta$ within a matrix $\alpha$, and being of a Widmanstatten type. Specifically, FIGS. 21A and 21B illustrate micro sections of an EOS sample at different magnifications, and etched with Kroll's reagent. This is very similar to wrought microstructures produced after heating to 1000° Celsius and forced air cooled. Grain size is in the region of 100 microns (μm). This type of structure may not yield good mechanical properties, and may require appropriate solution and ageing heat treatments to produce a material with acceptable mechanical properties. The EOS Ti-64 part etched with Kroll's reagent shows the crystal structure at low magnification (FIG. 21A) and a higher magnification (FIG. 21B), with showing the Widmanstatten type structure of individual grains.

Figure 22:
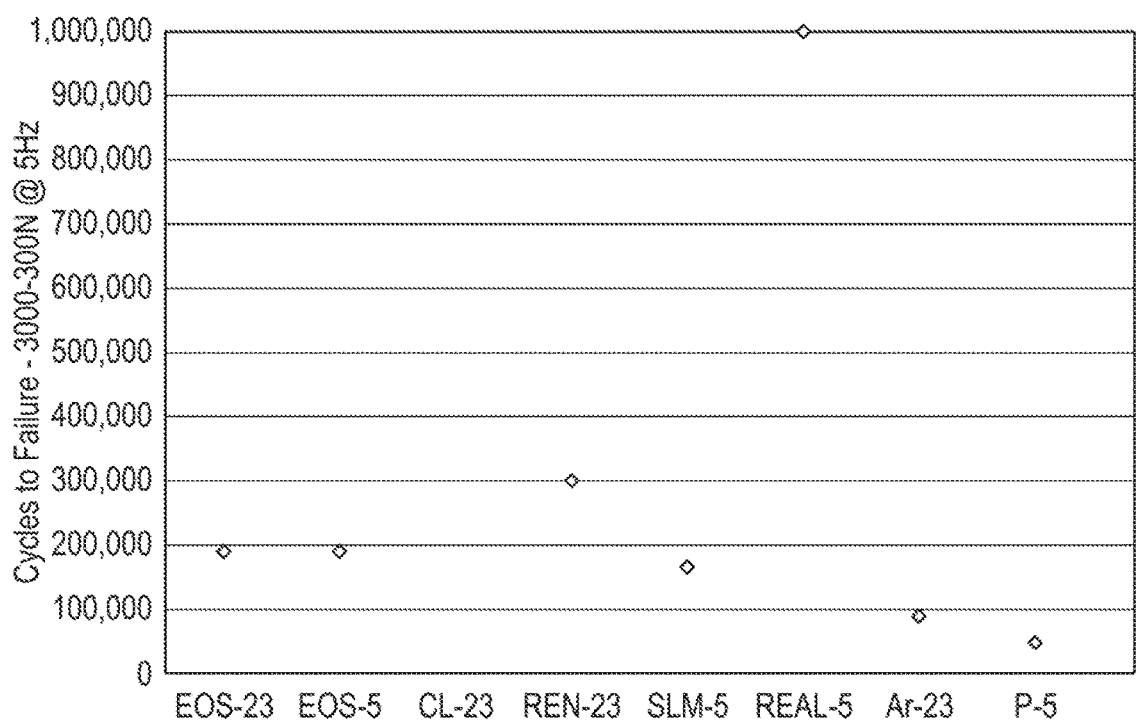
FIG. 22 illustrates four-point bend fatigue performance of HIPPED laser sintered and e-beam melted coupons as a function of machine suppliers. Tests conducted at 300 to 3000 Newton's at 5 Hertz (Hz).

(C) HIPPING: Hipping can be very effective at increasing the fatigue performance of ALM Ti-64 parts, as illustrated in FIG. 22. In general, fatigue performance may be improved 100% when the ALM Ti-64 parts are HIPPED at a temperature of 980° Celsius for 4 hours at a pressure of 200 MPa, and with an initial cooling rate of 10° Celsius/minute. For the samples produced by SLM solutions, ultimate failure occurred at 26,891 cycles when loaded between 4000 newton (N) and 400 newton (N) at 5 hertz (Hz) (not shown).

Specifically, FIG. 22 illustrates four-point bend fatigue performance of HIPPED laser sintered and e-beam melted coupons as a function of machine suppliers with the following parameters: part geometry of 100 millimeter (mm) long, an outer diameter of 10 millimeter (mm), and an inner diameter of 4.7 millimeter (mm); test conditions of 3000 newton (N) to 300 newton (N) at 5 hertz (Hz) according to ASTM 1264; HIPPED at a temperature of 980° Celsius for four (4) hours at a pressure of 200 MPa and with an initial cooling rate of 10° Celsius/minute. Failure typically occurred at around 200,000 cycles with the HIPPED part produced from the Realizer running out a 1M cycles, FIG. 22.

Figure 23A:
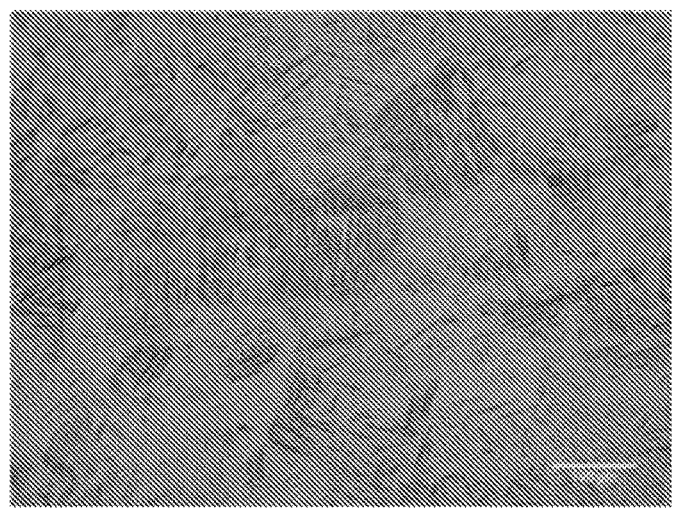
FIG. 23A illustrates the crystal structure of a Grade 23 titanium produced, as an as-built part, on an EOS M280 machine prior to a Hot Isostatically Pressing treatment.
Figure 23B:
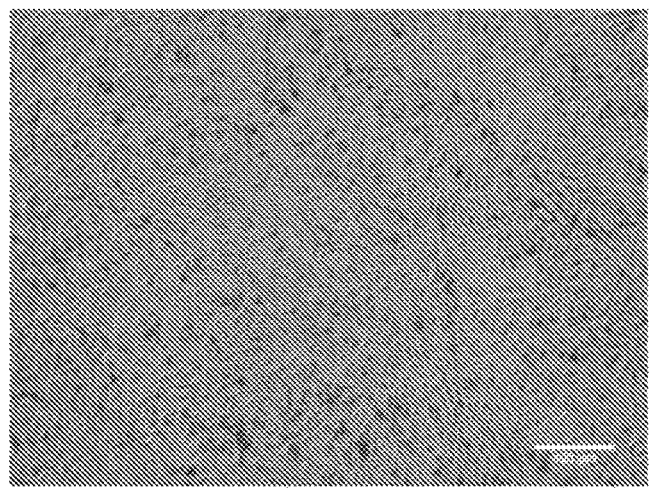
FIG. 23B illustrates the crystal structure of the Grade 23 titanium produced part of FIG. 21A after the part has been subjected to a Hot Isostatically Pressing treatment.

HIP treatment may refine the crystal structure to produce a lamella structure, with some similarity to conventionally manufactured titanium when heated above the $\beta$ transus temperature and cooled slowly. FIGS. 23A and 23B illustrated the effect of HIP treatment on Grade 23 titanium produced on an EOS machine, with FIG. 23A showing the as-built part and FIG. 23B illustrating the part after HIP treatment. The illustrations are typical of the type of modification observed with the samples from other machines, although the width of the lamella and the overall grain size varied with the other samples. The main difference from conventional Ti-6Al-4V titanium is the rather disordered nature of the lamella observed in all of these samples. The microstructures observed with the laser sintered parts comprises bands of $\alpha$ separated by very small regions of $\beta$.

Figure 24:
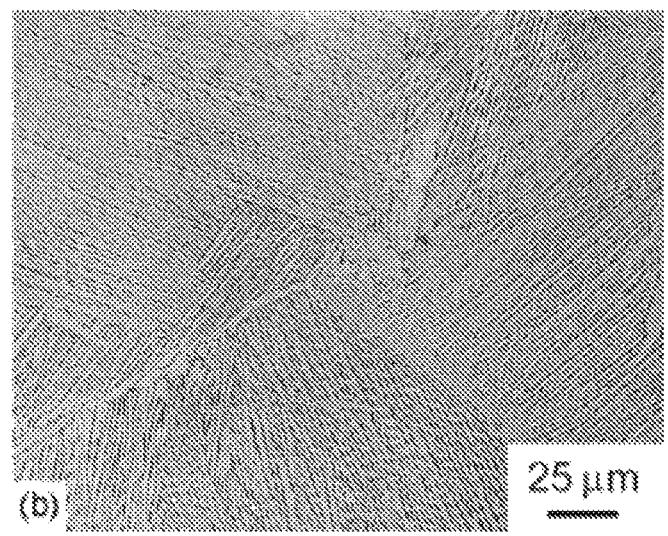
FIG. 24 illustrates a generally typical ordered structure of conventional lamella type Ti-6Al-4V titanium wrought alloy heated to the β transus temperature of 1005° C. and cooled at a rate of 100° C. min−1 to 700 C., stabilized for 2 hours then allowed to cool in the oven.

As illustrated in FIG. 24, conventional lamella type Ti-6Al-4V titanium forms larger zones of parallel lamella within the crystals. Specifically, FIG. 24 shows the typical ordered structure of conventional lamella type Ti-6Al-4V titanium alloy. The HIP treated samples (FIG. 23B) are far more disordered than the conventional lamella type Ti-6Al-4V titanium alloy shown in FIG. 24. This contributes to the lower fatigue performance of these samples during fatigue testing. It can also be seen that definite crystal boundaries are present in the conventional sample, but these are hard to define in the test samples examined, as there appeared to be no clear distinction between lamella colonies and grain boundaries. More specifically, FIG. 24 illustrates Ti-6Al-4V titanium alloy that is conventionally wrought and heated to the $\beta$ transus temperature of 1005° Celsius (C), cooled at a rate of 100° C. min-1 to 700° C., stabilized for 2 hours, and then allowed to cool in the oven.

The ALM samples were given an HIP treatment at 980° Celsius, so it is likely that the $\beta$ transus was not reached, and therefore the phase change to $\beta$ was not achieved. This incidence, combined with the slow rate of cooling of 10° C. min−1, explains the difference between the wrought microstructure and the studied ALM samples. In order to create a suitable structure by heat treatment, a $\beta$ transus temperature must be reached. This will then allow an ordered lamella structure to be produced on cooling. The width of the lamella is dictated by the cooling rate, with a finer structure being achieved at faster rates of cooling. It has been found that the width of the lamella (t) should be microns, and the size of the colonies of parallel lamella (d) should be 30 microns for maximum fatigue strength.

A more ordered, parallel structure should be achieved if the HIP temperature is increased to 1000° Celsius so that full $\beta$ transus is achieved. In order to achieve an ordered structure of $\alpha+\beta$ lamella-type alloys, cooling rates from the $\beta$ transus temperature should be between 0.24° C. min−1 and 72° C. min−1, with the faster cooling rate producing smaller lamella. The cooling rate in the HIP furnace used for the current batch of ALM parts is 10° C. min−1, and the lamella produced had widths of between 4.05 microns and 6.12 microns, FIG. 26. This is not far from the optimum size for maximum fatigue strength. Therefore, a more ordered, parallel structure should be achieved if the HIP temperature was increased to 1000° Celsius so that full β transus is achieved.

Figures 25, 26, 27:
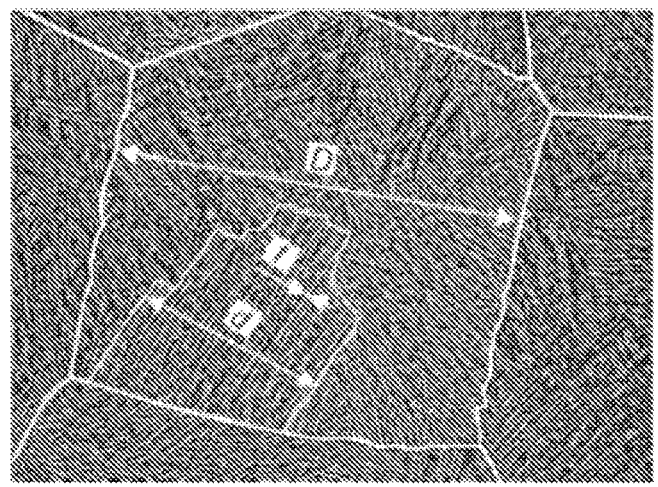
FIG. 25 provides a table of surface finish or roughness of as-built parts that were subjected to post-machining.
FIG. 26 provides average measured thickness of the α lamella in the ALM samples studied.
FIG. 27 provides critical parameters that dictate the fatigue properties of lamella type titanium alloys, (D)=size of grain, (t)=width of the lamella, (d)=size of the colony of parallel lamella.

(D) HIPPING & Machining/Polishing: Post-machining of the external surface of the part has a significant improvement in fatigue performance. For example, techniques such as abrasive fluid machining results in the flattening out of the surface and a reduction in the number of crack initiation sites in the test part. As illustrated in FIG. 25, the surface finish or roughness of the external geometry of the as-build parts that were subjected to such post-machining experienced increases from 5.43 μm (Realizer)-23.4 μm Ra (Arcam), to 0.4 μm Ra after abrasive fluid machining.

Figure 28:
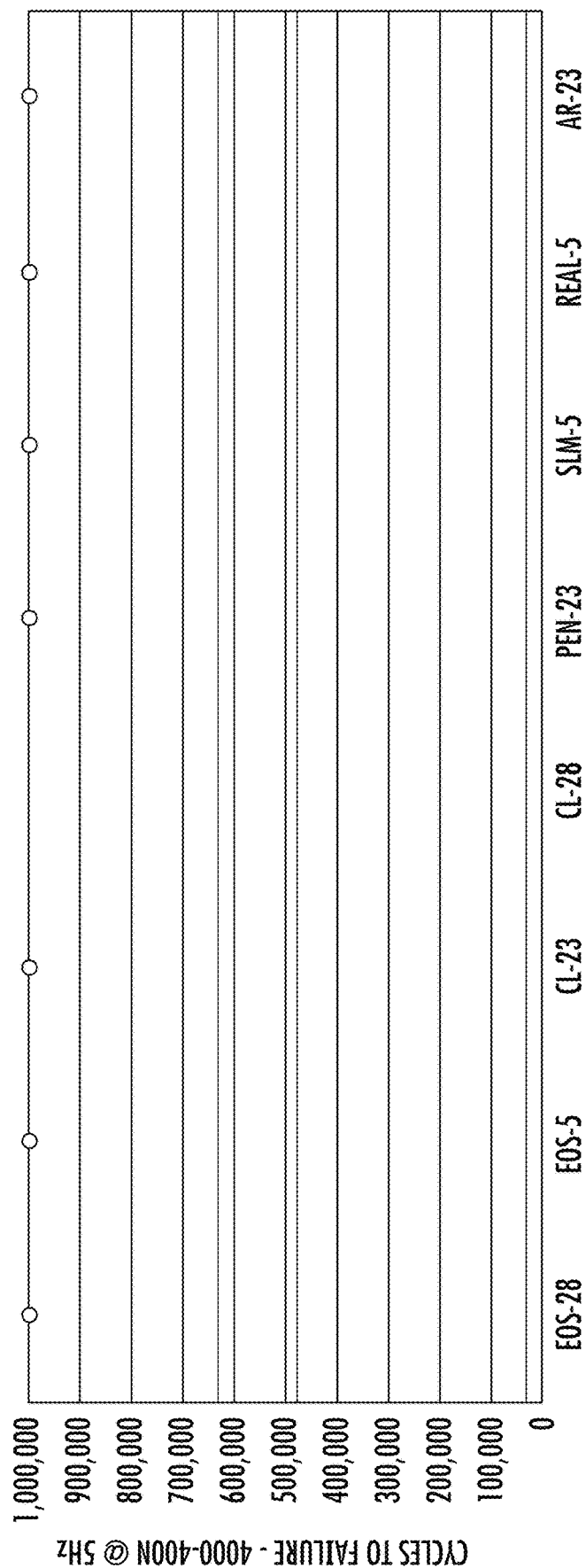
FIG. 28 illustrates four-point bend fatigue performance of surface polished and HIPPED laser sintered and e-beam melted coupons as a function of machine suppliers. Tests conducted at 400 to 4000 Newton's at 5 Hertz (Hz).
Figure 29:
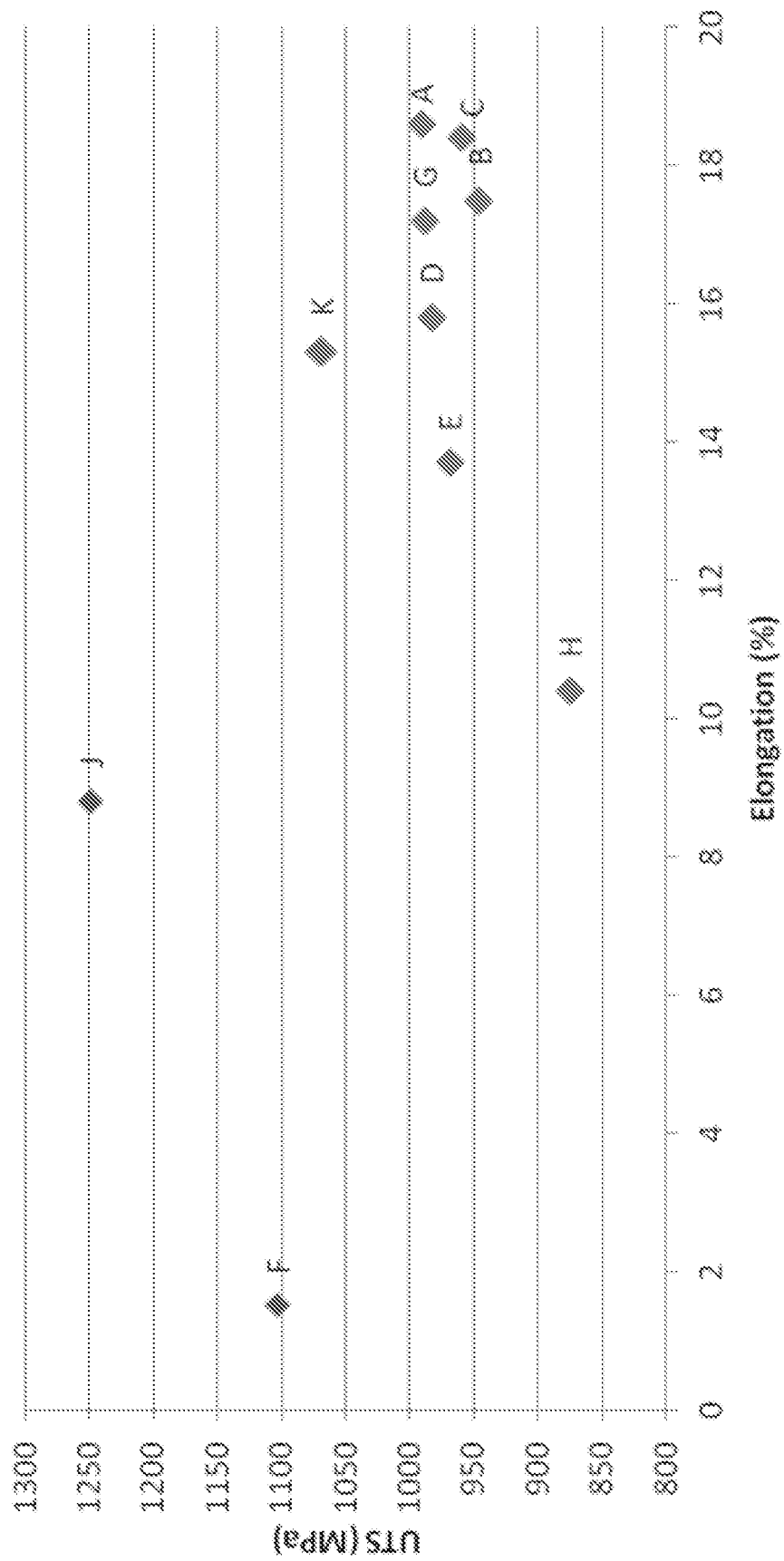
FIG. 29 illustrates Load Extension curves for heat-treated and non-heat treated ALM parts. Points F and J represent performance of non-heat treated parts. These parts are strong, but brittle.

The combined impact of HIPPING and external polishing produces parts which has fatigue properties that are comparable to the wrought parts (i.e., run out at 1M cycles when loaded between 4000 newton (N) and 400 newton (N) at 5 hertz (Hz)) as illustrated in FIG. 28. The results also indicate that an ALM part manufactured from TiAl6V4 Grade 5 material (higher oxygen content) performs adequately well. This result may offer a significant benefit, as Grade 5 powder material typically costs 35% less than the Grade 23 material, making the economic arguments for the process relatively significantly more attractive. Specifically, FIG. 28 illustrates four-point bend fatigue performance of surface polished and HIPPED laser sintered and e-beam melted coupons as a function of machine suppliers and having the following parameters: part geometry of 100 millimeter (mm) long, with an outer diameter of 10 millimeter and an inner diameter of 4.7 millimeter (mm); and, test conditions of 4000 newton (N) to 400 newton (N) at 5 hertz (Hz) according to ASTM 1264. FIGS. 29-30 illustrates the Load Extension curves for heat-treated and non-heat treated ALM parts. Points F and J represent performance of non-heat treated parts. These parts are strong, but brittle.

The present invention provides at least the following advantages over the prior art: (1) mechanical properties similar to wrought parts; (2) Grade 5 Ti powder can be used, which in turn may provide an economic advantage; and, (3) improved part tolerance. However, it should be understood that these advantages are exemplary and do not in any way limit the scope of the present invention.

Embodiments of the present invention further provide an optimal DMLS manufacturing route for orthopedic devices, with a potential six-fold reduction in manufacturing time. In another embodiment, a method of manufacturing an elongated orthopedic device via direct laser sintering is provided, including the following steps:

(1) Producing a virtual 3D dimensional external elongated device model;

(2) Manufacturing an elongated device in an appropriate build direction via direct metal sintering according to the 3D model utilizing a laser power of at least 300 watts (W) and TiAl6V4 powder of at least Grade 5 quality, and wherein the powder is only sintered around the outside and inside circumference of the model to a set diameter, leaving the central section between the inside and outside circumference consisting essentially of un-sintered powder;

(3) Scanning at greater than 4 times the normal speed for laser sintering (i.e., 3000 millimeters/second);

(4) Subjecting the elongated ALM device to Hot Isostatically Pressing (HIP) utilizing a temperature of at least 1000° Celsius with a cooling rate of between 0.24° C. min-1 and 72° C. min-1, thereby ensuring the central powder section is sintered; and (5) Machining and polishing the HIP processed elongated device to the required geometrical and surface tolerances (e.g., 32 Ra μm (Realizer)).

The following two scanning strategies ("Hyper" laser scan and "Boundary Scan—in situ shelling") assume that the bulk of the cost of goods of manufacturing an ALM nail is associated with the build time in the DMLS machine.

(A) "Hyper" Laser Scan: The economic advantages of operating a laser sintering machine at a "hyper-scanning speed" is apparent from the data outlined in FIGS. 31 and 32, which was generated from three DMLS machines equipped with single, twin, and quad scanner optic capabilities. For routine laser scanning programs on single laser systems, a batch of 100 nails would take approximately 4.5 days to complete, equating to 65 minutes per nail (FIG. 25). This does not compare favorably to the throughput obtained from standard machining operations, which comparatively equates to approximately 2.5 minutes per nail or 600 nails per day. If a DMLS machine equipped with four lasers was set to operate at a higher scan speed, each nail would take only 12 minutes to build (FIG. 32), thereby making the process significantly more attractive for high volume manufacture (i.e., 10,000 parts per annum). By operating at a higher scan speed (typically 3-4.times. normal speed for laser sintering; 1000 mm/s), the parts will only be partially sintered (typically 50% of the entire volume of the part). This accelerated scanning speed is still significantly lower than the scanning speed used in electron beam melting processes (1000-8000 meters/second). This scanning strategy assumes the following: (a) any residual porosity left in the part after building is removed after heat treatment; (b) a standard heat treatment cycle is used; (c) dimensional changes resulting from part shrinkage are factored into the original design of the CAD file or are controlled by the Magic® program; and, (d) the mechanical properties of the hyper-scanned speed parts are equivalent to a normal scan.

FIG. 31 illustrates calculations for the production of 100 pieces of fully dense intramedullary nails at normal scanning speed using single, twin, and quad lasers, and utilizing the following parameters: slice count=3911; recoating time=31, 288 seconds; and, scanning speed=600 mm/s. FIG. 32 illustrates calculations for the production of 100 pieces of fully dense intramedullary nails at "hyper-scanning speeds", and utilizing the following parameters: slice count=3911; recoating time=31,288 seconds; and, scanning speed=3000 mm/s.

FIGS. 33A-34B illustrate a breakdown of costs for making an additive-manufactured Ti-64 nail. The fixed costs include the cost of powder (assuming current supply chain options for qualified powder without access to lower cost metal spray equipment), post machining, and packaging/ sterilization. The total cost of making an ALM nail using this manufacturing route is $149.50. The cost for operating at a hyper-scan speed has a significant impact on build time costs, reducing it from 62% to 25.6% of the overall manufacturing cost, as illustrated FIGS. 33B and 34B. Further, the cost of producing a "hyper scanned" part is reduced from $149.50 to $75.90, which is aligned with the cost of manufacturing a machined part of equivalent geometry.

Figure 33A:
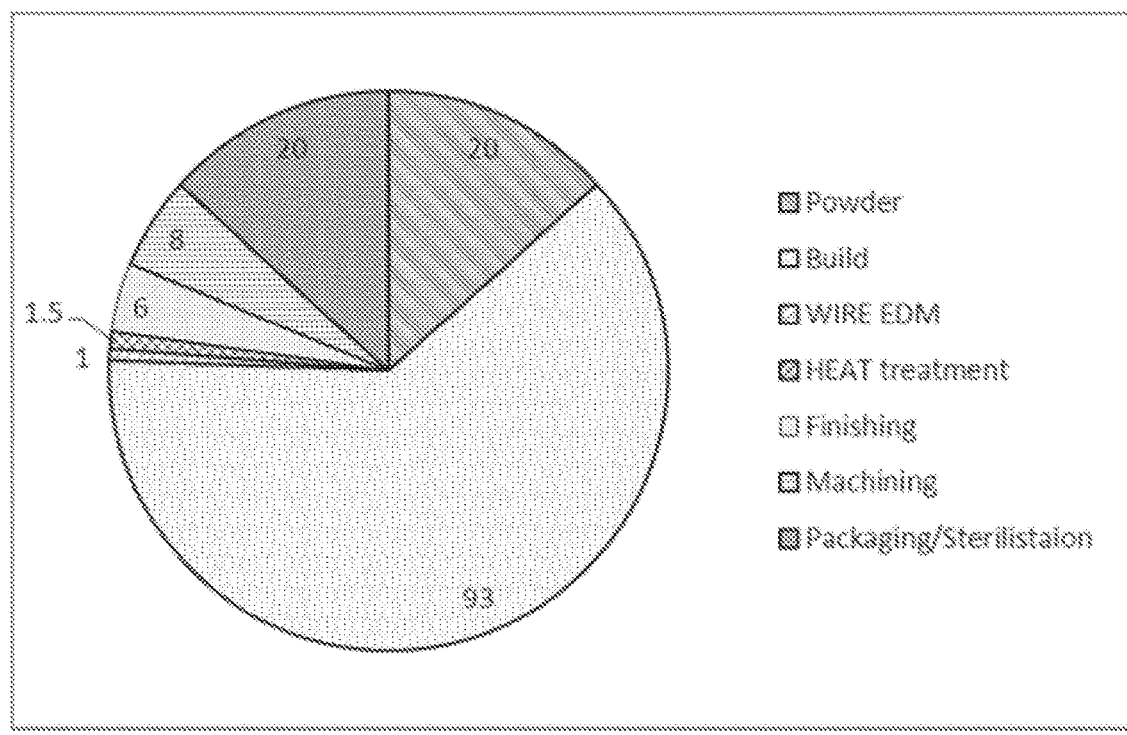
FIG. 33A illustrates an exemplary breakdown of production costs ($) per step for making 100 intramedullary nails using standard scanning conditions. Assumptions:—Cost of running the ALM machine=$97 per hour. Cost of implant grade powder=$255 per Kg. 96 hour build time to manufacture 100 nails.
Figure 33B:
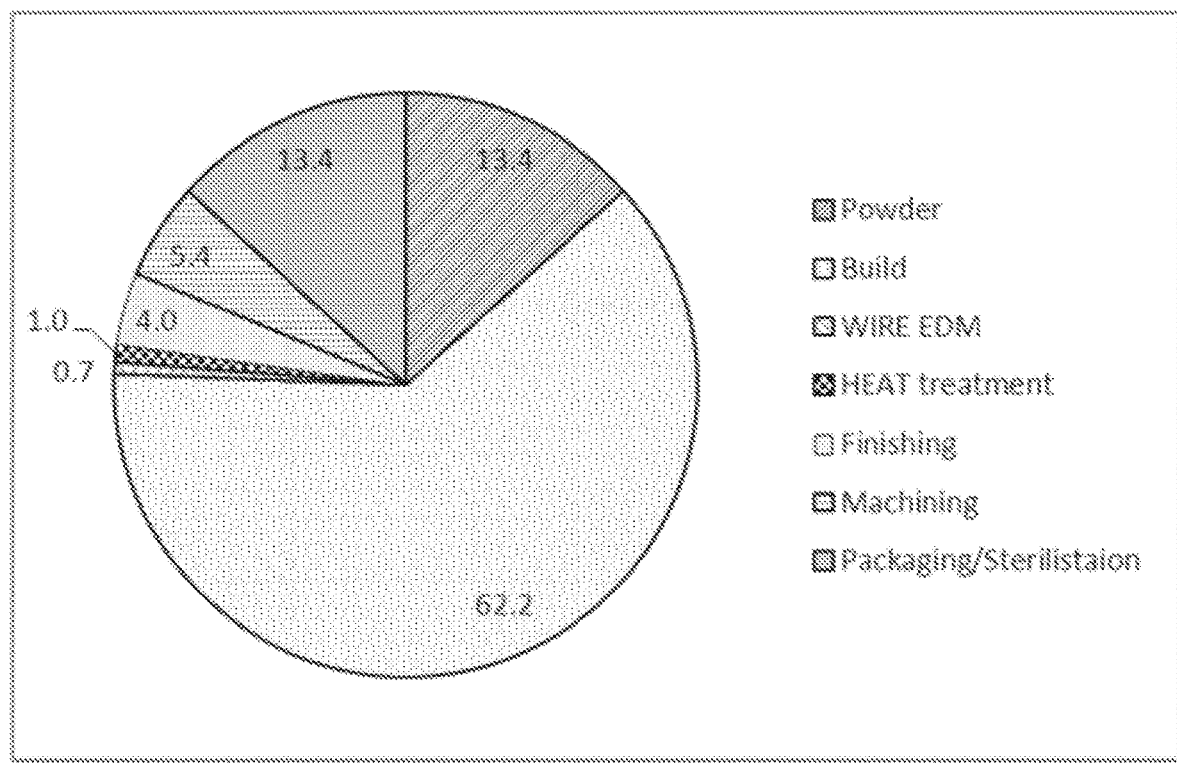
FIG. 33B illustrates the production costs shown in FIG. 27A as a percentage cost per manufacturing step.

The production costs for making 100 nails using standard scanning conditions (scanning speed <1000 mm/s) for an SLM DMLS machine is shown in FIG. 33A as cost breakdown (dollars/manufacturing step), and FIG. 33B as a percentage cost per manufacturing step, and with the following assumptions: cost of running the ALM is $97/hour; cost of implant grade powder is $255/kg; and, build time is 96 hours to manufacture 100 nails.

Figure 34A:
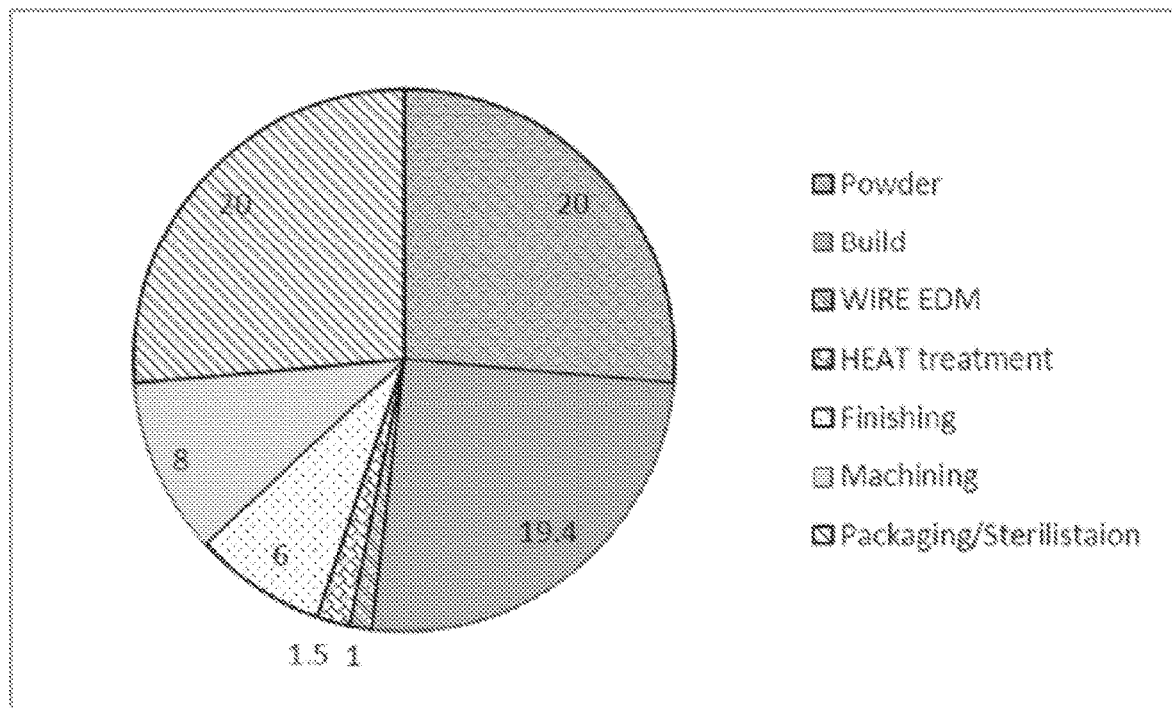
FIG. 34A illustrates an exemplary breakdown of production costs for making 100 intramedullary nails using scanning conditions higher than those associated with the example depicted in FIGS. 31A-32A.
Figure 34B:
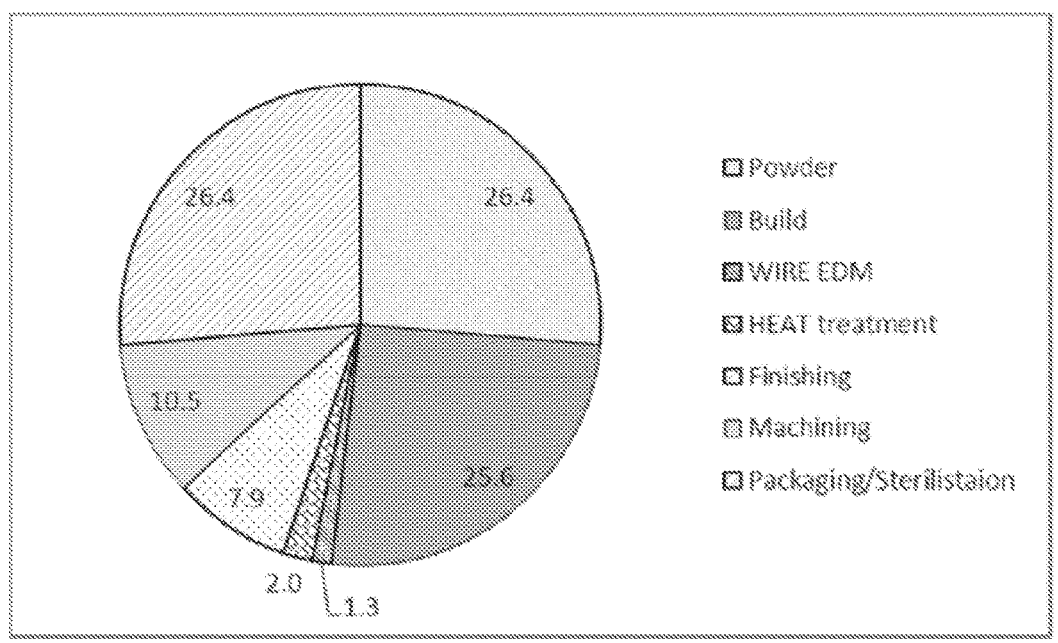
FIG. 34B illustrates the production costs shown in FIG. 34A as a percentage cost per manufacturing step.

FIGS. 34A and 34B illustrate production costs for making 100 nails using "higher speed" scanning conditions (scanning speed <1000 mm/s) for an SLM DMLS machine showing cost breakdown in dollars per manufacturing step (FIG. 34A), and percentage cost per manufacturing step (FIG. 34B), and using the following assumptions: cost of running the ALM is $97/hour; cost of implant grade powder is $255/kg; build time is 96 hours to manufacture 100 nails; and, heat treatment cycle is HIPPED at 1050° Celsius for 6 hours, with all heat treatments carried out in an inert argon atmosphere.

(B) Boundary Scan: A second approach for reducing the cost of building the parts in the DMLS chamber is to use a scanning strategy which restricts the sintering to the boundary layers (i.e., the outside and inside surface of a cannulated part), aptly termed the "Baked Bean Can or in situ shelling" model. This scanning strategy omits the hatch or core scan of the part. A three dimensional model of the proximal end of a Trigen Meta tibial nail highlighting the concept of boundary layer scanning is illustrated in FIG. 359. With this scanning approach, only 5% of the total volume of the part is sintered on the build platform. Specifically, FIG. 35 illustrates the concept of a boundary or "Baked Bean Can" scanning strategy for densifying the outer and inner layers of a Trigen Meta tibial nail (proximal tapered region) to reduce build time in the DMLS chamber. The core of the part contains free-flowing powder which is densified after heat treatment. In this example, certain part design features, such as, for example, keyway and slot screw holes, have been turned off.

Additionally, in certain embodiments of the present invention, an intramedullary nail or other types of implants are manufactured via the following steps and processes.

Figure 38:
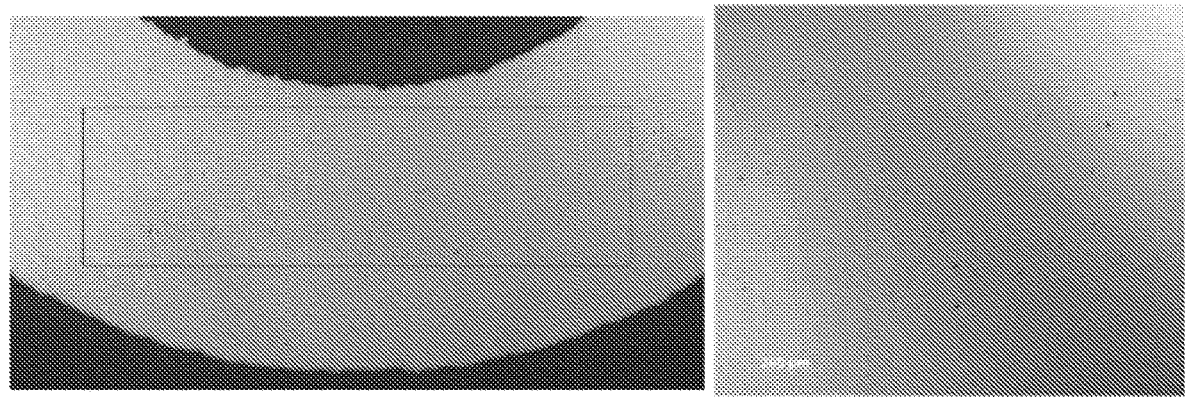
FIG. 38 illustrates optical images acquired from the polished face of the wall section at the distal tip after heat treatment. The measured porosity and average pore size was approximately 0.25%, and 3.4 microns respectively.

(I) Boundary Scan: FIGS. 36A and 36B illustrate a cross section of an intramedullary nail 110 including an additive manufactured component 100 subsequent to a boundary scan highlighting the dimensionally adjusted part to account for shrinkage effects (FIG. 36A), and HIP processed additive manufactured component indicating the final "stabilized" nail 110 dimensions after heat treatment (FIG. 36B). Specifically, FIG. 36A illustrates an additive manufactured component 100 that will provide the orthopedic intramedullary nail 1100 before a boundary scan indicating a dimensionally adjusted CAD file to account for dimensional shrinkages (typically <5%), and FIG. 36B illustrates an orthopedic intramedullary nail 110 after HIPPING and which indicates a fully densified part with the specified geometry. Referring to FIG. 36A, the additive manufactured component 100 is manufactured using DMLS technology with a boundary scan only approach. In traditional practices, various scan strategies are used to produce a sintered model representing the complete intramedullary nail device 110. In the proposed method, a "Baked Bean Can" of the additive manufactured component 100 is produced by laser sintering the three dimensional model, and more specifically the external surface 102 and the internal surface 104 to a desired thickness, which could be, for example, in the range of about 100 microns (μm). The internal cannulation 106 would be maintained with this scanning approach in addition to an un-sintered powder core 108. Referring to FIG. 36B, after HIPPING, the nail 110 becomes densified by the heat treatment with some accompanying dimensional changes, which reflect the amount of shrinkage experienced by the additive manufactured component 100 during the heat treatment step. Typically, nails are supplied with a powder core using a boundary scanning strategy as indicated in FIG. 37a. The parts are densified at either 5% in the build chamber. The bottom surface of the nail is extruded in the Magics software to 3 mm to prevent the powder from escaping from the distal end of the part after removal from the platform, FIG. 37b. FIG. 38 illustrates the degree of porosity remaining in the cross-section of the part. Typically, the measured porosity is 0.3%, FIG. 38. Moreover, the average pore size is approximately 3.4 microns, FIG. 38.

Figures 39A, 39B:
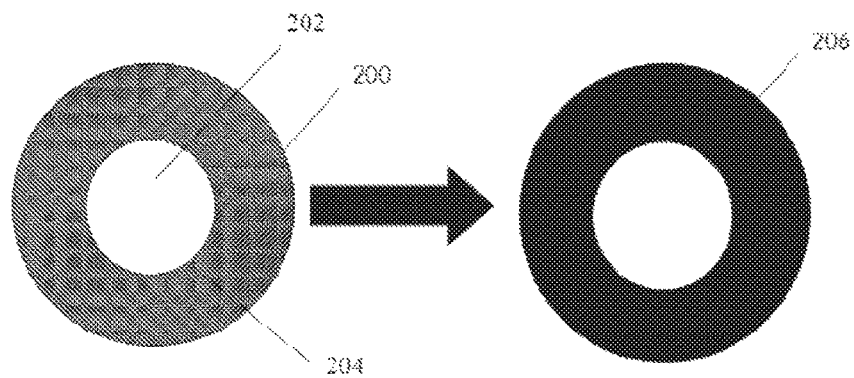
FIG. 39A illustrates a model of an orthopedic intramedullary nail after a hyper-laser scan, and which is dimensionally adjusted to account for dimensional shrinkages.
FIG. 39B illustrates a model of an orthopedic intramedullary nail after HIPPING, and which indicates a fully densified part that meets the required CAD file part specification.

(II) Hyper-Laser Scan: FIGS. 39A and 39B illustrate a cross section of an intramedullary nail 206 including an additive manufactured component 200 after a hyper-laser scan producing 50% densification in the part. The figure highlights the dimensionally adjusted nail 206 that accounts for shrinkage effects to the additive manufactured component 200, which may occur after heat treatment (FIG. 39A), and a HIP processed nail 210 indicating the final "stabilized" part dimensions after heat treatment (FIG. 39B). Specifically, FIG. 339A illustrates an additive manufactured component 200 that will be used to form the orthopedic intramedullary nail 210 after a hyper-scan which indicates a dimensionally adjusted CAD file to account for dimensional shrinkages, and FIG. 39B illustrates an orthopedic intramedullary nail 210 after HIPPING which indicates a fully densified part with the required geometry.

Referring to FIG. 39A, the additive manufactured component 200 is manufactured using DMLS technology with a hyper laser scan. In traditional practices, various scan strategies are used to produce a sintered model representing the complete intramedullary nail device 210. In the proposed method, a cannulation 202 is surrounded by a semi-sintered core 204. Referring to FIG. 39B, after HIPPING, the nail 206 becomes densified by heat treatment with some accompanying dimensions changes which reflect the amount of shrinkage experienced by the part during the heat treatment step.

Figure 40:
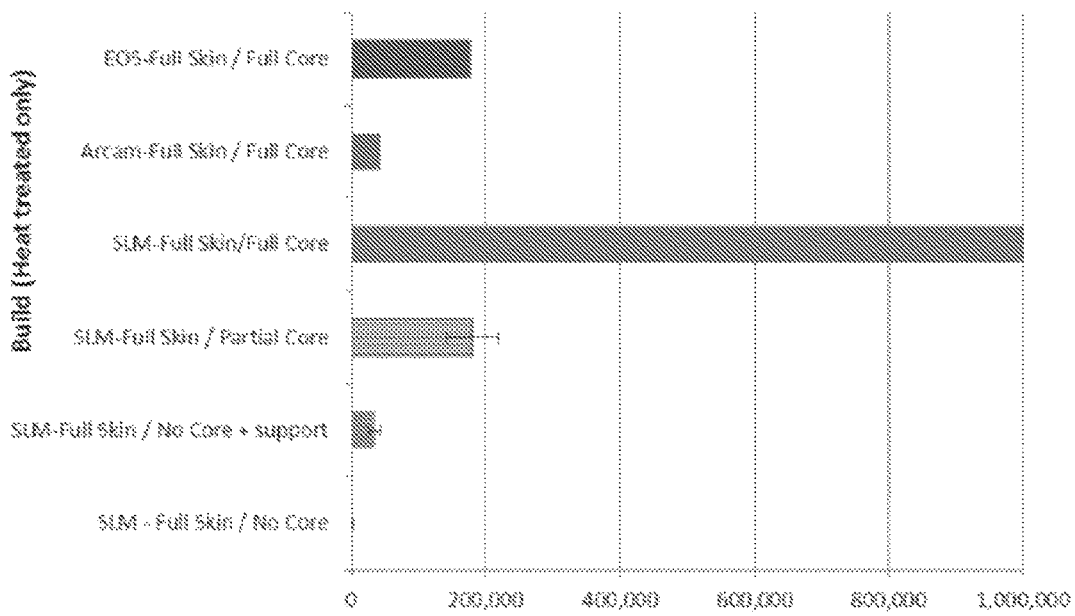
FIG. 40 illustrates the four point bend fatigue performance of ALM parts produced by SLM solutions subjected to variable scanning strategies (full skin, no core, full skin, partial core).

Hyper-scanned parts supplied by SLM solutions were subjected to heat treatment only, and the number of cycles to failure compared to standard scanned parts produced after the same step in the process, FIG. 40. The hyper-scanned parts consisted of three groups of parts: full skin with powder core, full skin with powder core, with extruded distal end to allow parts to be heat treated off the build platform, and parts with a full skin and partially powder core. The mean cycles to failure after the heat treatment step when loaded between 3000 & 300 N were 1,161+/−288 for the parts with the full skin and powder core. The corresponding mean cycles to failure after the heat treatment step were 34.7+/−9.6 k for the parts with the full skin and powder core, which had the extruded distal end. The corresponding mean cycles to failure after the heat treatment step were 180,068+/−38.7 k for the parts with the full skin and partially scanned core, which had the extruded distal end. The improvement observed in the fatigue performance from the powder core samples after inclusion of the extruded distal end was believed to be due to the benefits accrued from heat treating the part away from the build plate. The extruded 'floor' prevented the powder from coming out. The nails were positioned over the platform and then dropped by 2 mm, (in CAD space). It is assumed that the HIPing would not have worked well with the nails without the extruded floor, as there would have been stress and micro-cracks around the bottom, which would have made them quite 'leaky.' For comparative purposes, parts subjected to a standard scanning strategy (EOS, Arcam and SLM solutions) are also included in the same figure. The data suggests that the fatigue performance of the partially sintered cores was comparable with the parts supplied by EOS subjected to a standard scanning strategy, FIG. 40.

In another embodiment of the present invention, an anti-microbial nail may be provided. The cost saving realized from the scanning strategies discussed above may enable other cost effective processes to be included within the process map.

Figure 41:
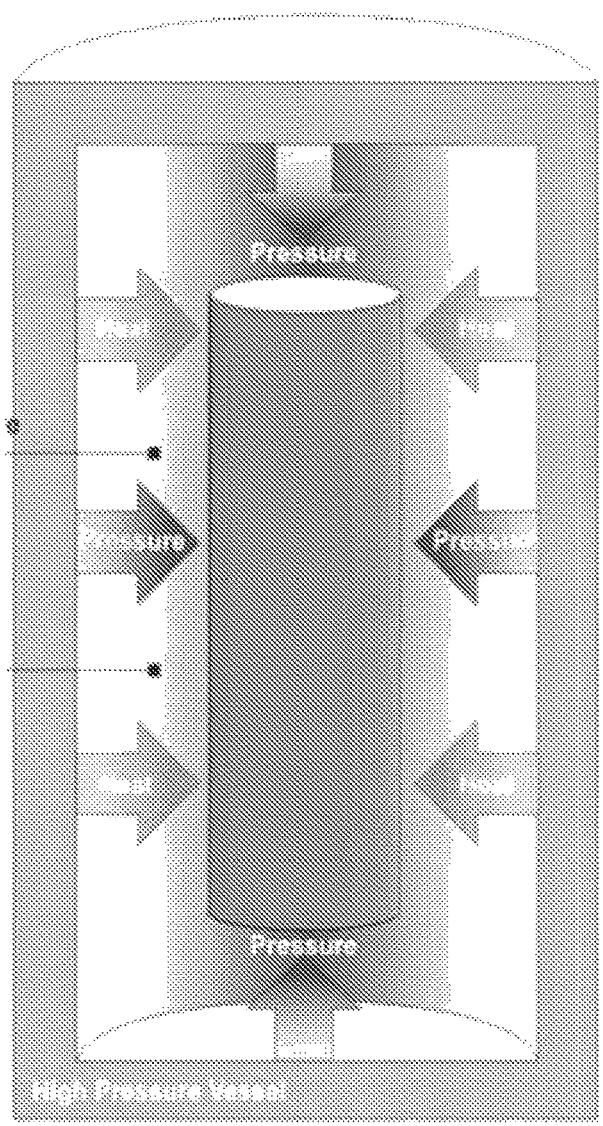
FIG. 41 illustrates a sagittal section through the HIPPING oven highlighting the exposure of an ALM part to silver vapor.

In a further embodiment of the present invention, a silver hip implant may be provided. Specifically, as illustrated in FIG. 41, silver is deposited onto a hip implant during the HIPPING step, and may use the following approaches: (a) a silver plated/coated work-piece, and (b) a modified compression media (argon gas-silver vapor). Both approaches produce a silver coated product using a non-line-of-sight process, which is known to have anti-microbial properties. Specifically, FIG. 41 illustrates a sagittal section through the HIPPING oven highlighting the exposure of the ALM part to silver vapor. This coating technology assumes that the deposited silver lay is thicker than 0.1 millimeters (mm) to accommodate any post machining operations.

Figure 42:
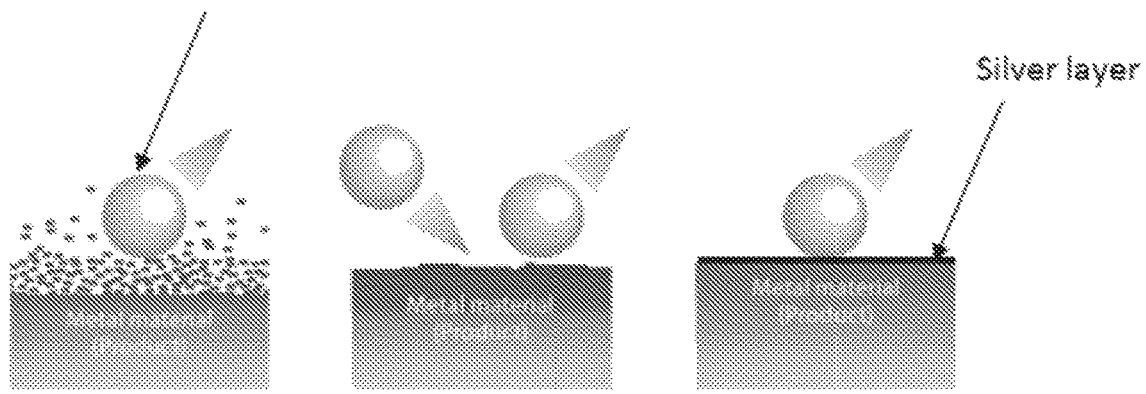
FIG. 42 illustrates a schematic illustration of a bead blast procedure highlighting the deposition of silver onto a working part during a finishing operation.

In still another embodiment of the present invention, a silver-coated bead blast treatment may be provided. As illustrated in FIG. 42, such an embodiment may constitute a one step process that involves the use of silver-coated ceramic particles produced from either silver plating or silver nitrate coating that is fired at the surface. In addition to producing a desirable surface finish, the particles produce a hardened layer of silver-titania that has anti-microbial properties. Specifically, FIG. 42 is a schematic illustration of a bed blast procedure highlighting the deposition of silver onto a working part during a finishing operation sing silver coated grid or bead blast.

The present invention provides significant savings in terms of cost of goods over prior implants and methods of manufacture. However, it should be understood that these advantages are exemplary and do not in any way limit the scope of the present invention.

Another embodiment of the present invention provides an orthopedic implant device, such as, for example, an intramedullary nail that has the design freedom of additive manufacturing, and which includes a longitudinal internal channel that is capable of housing a removable sensor probe that is configured to register distal and proximal locking holes. The orthopedic implant device may also have an internal geometry that facilitates variable stiffness in the anterior-posterior (A/P) plane and medial lateral (M/L) plane and/or an internal geometry that offers a lower stiffness implant for larger patients. A further embodiment of the present invention provides a minimally invasive method for auto-dynamization so as to provide biomechanical loading to the healing fracture.

Figure 43A:
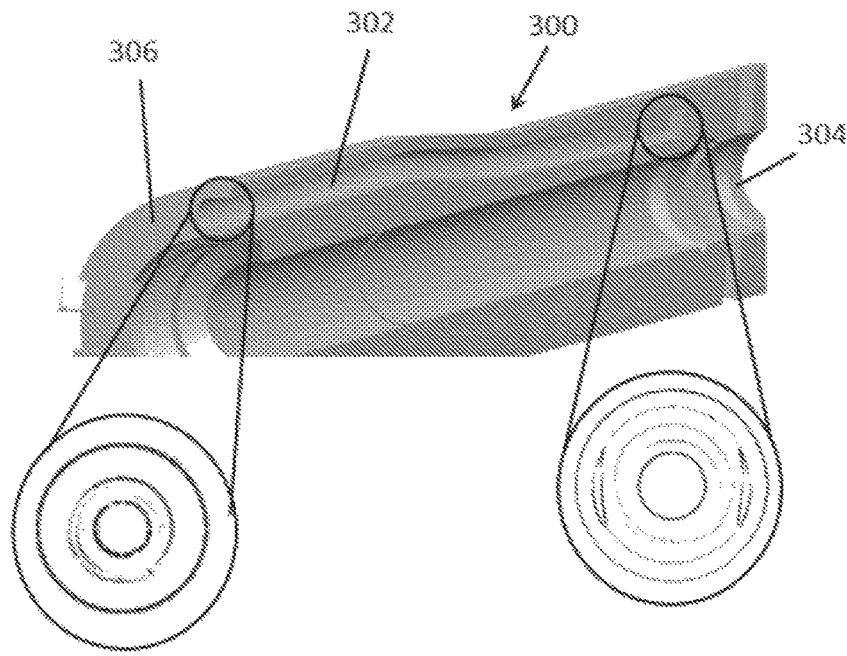
FIG. 43A illustrates a three-dimensional (3D) model of an intramedullary nail with an internalized channel that extends generally parallel to the cannulation for temporarily housing a sensor probe.
Figure 43B:
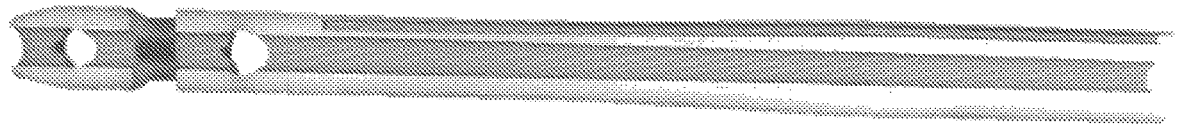
FIG. 43B illustrates a microCT image of a nail with an internalized channel (1.5 mm diameter) highlighting no residual powder residing in the channel after the build.
Figures 47, 48:
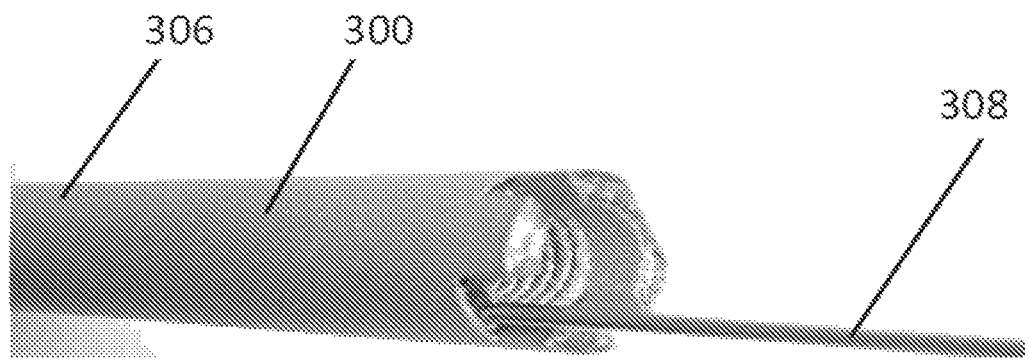
FIG. 47 additive manufactured nail that includes an internal sensor probe channel.
FIG. 48 illustrates a perspective view of a proximal end of an intramedullary nail that was constructed via additive manufacturing, and which includes an internalized probe channel that is adapted to receive the insertion of a removable sensor probe.

(A) In Situ Distal and Proximal Sensor Probe for Intra-Operative Screw Hole Targeting: embodiments of the present invention include a longitudinal internal channel created in the wall section of an orthopedic device, such as an intramedullary nail, using additive manufacturing for housing a removable sensor probe for registration of the distal and proximal screw holes. For example, FIG. 43a illustrates an intramedullary nail 300 with an internal sensor probe channel 302 running parallel to the cannulation 304. Further, FIG. 43b illustrates a microCT image captured from an ALM part with an internalized channel in the wall section. The longitudinal cross-section through the part shows that there is no residual powder residing in the channel after the build phase. FIG. 48 illustrates a proximal end of an intramedullary nail 300 that was constructed via additive manufacturing, and which includes an internal sensor probe channel 302 (FIG. 43a) in a wall section 306 that is adapted to receive the insertion of a sensor probe 308. The inclusion of a removable sensor probe in the channel 302 may facilitate proximal locking, as the sensor probe is not located in the cannulation of the nail, thereby allowing surgeons to drill for, and insert screws into, the nail 300.

The shape of the internal sensor probe channel 302 may be created using additive manufacturing based upon the constraints imposed by the geometry of the intramedullary nail 300. In the illustrated embodiment, the internal sensor probe channel 302 is located within the wall section 306 of the intramedullary nail 300 to ensure that the probe that may be received in the channel 302 does not become incarcerated in the intramedullary canal during removal. The longitudinal channel is approximately 1.5 mm in diameter extending the length of the nail and terminating just above superior distal screw hole. Locating the internal sensor probe channel 302 within the wall section 306 will avoid the need for a welded lid, which otherwise can add complexity and cost to the manufacturing process.

Figure 44:
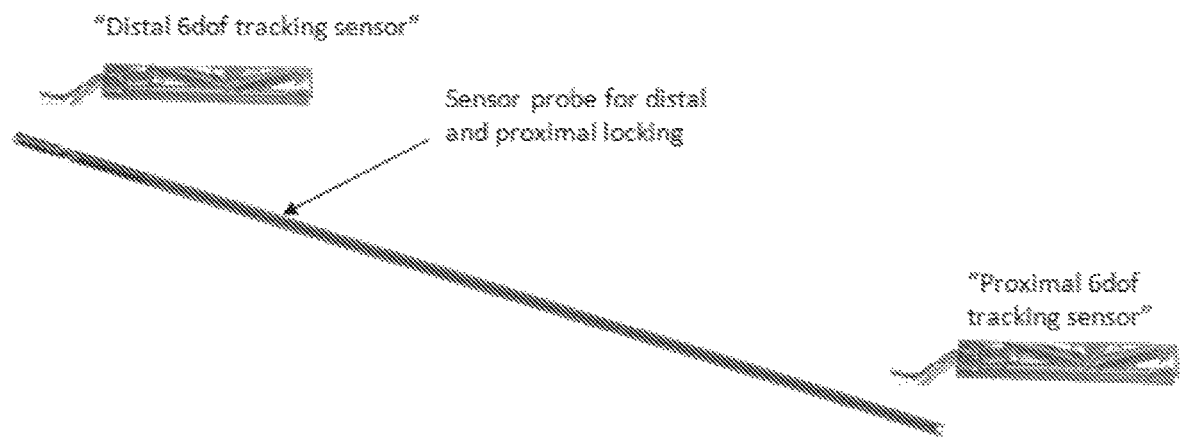
FIG. 44 illustrates a three-dimensional (3D) model of a removable sensor probe that may be designed to operate in the internalized sensor probe channel of the intramedullary nail depicted in FIG. 43.
Figure 45A:
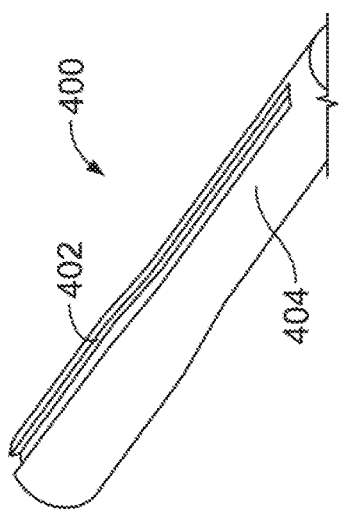
FIGS. 45A and 45B illustrate a model of an intramedullary nail having an open channel created at a proximal end, and in an outside surface, of an intramedullary nail, which is amenable to traditional manufacturing techniques.
Figure 45B:
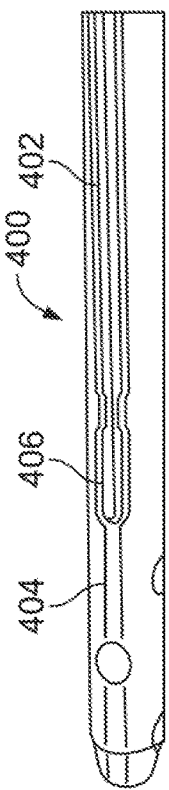

FIG. 44 illustrates an embodiment of a removable sensor probe designed to operate in this channel 302. Typical probe and sensor dimensions may include, but are not limited to, a 1.422 millimeter (mm) outer diameter, a 1.22 millimeter (mm) inner diameter, a 1.12 millimeter (mm) height, a 0.61 millimeter (mm) width, and a 30 millimeter (mm) length. Additionally, the sensor probe may be constructed from a variety of different materials, including, for example, stainless steel, or another rigid or semi-rigid metallic material. It can also include a potting compound such as a medical grade silicone rubber or epoxy resin to protect the electronic components from moisture and vibrational forces. Further, the configuration of the sensor components on the printed circuit board (PCB), i.e. the two coiled ferrites, also referred to as the six degree of freedom tracking sensors, are preferentially arranged at 180 degrees to each other. Such a configuration may minimize the overall diameter of the sensor unit, such as, for example to 1 millimeter (mm), and which may be positioned in an internal sensor probe channel 302 having a diameter in the wall of the nail that is less than 1.5 mm. The location of the channel also allows the nail to be locked at either the distal or proximal end first providing more options for the Surgeon. The probe is also designed to be removed after the nail has been locked within the bone channel 302. FIGS. 45A and 45B illustrate a model of an intramedullary nail 400 having a channel 402 created in the outside surface 404 of the nail 400 at the proximal end that is amenable to traditional manufacturing techniques. As depicted, the channel in FIG. 45B includes a removable sensor probe 406. This design requires a welded plate to prevent the probe from becoming incarcerated during extraction from the bone canal.

Figure 46A:
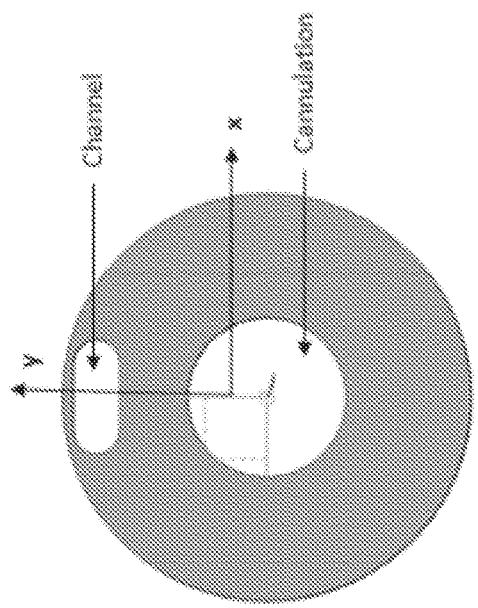
FIG. 46A illustrates an end view of exemplary geometry for an internal sensor probe channel that may be created using additive manufacturing.
Figure 46B:
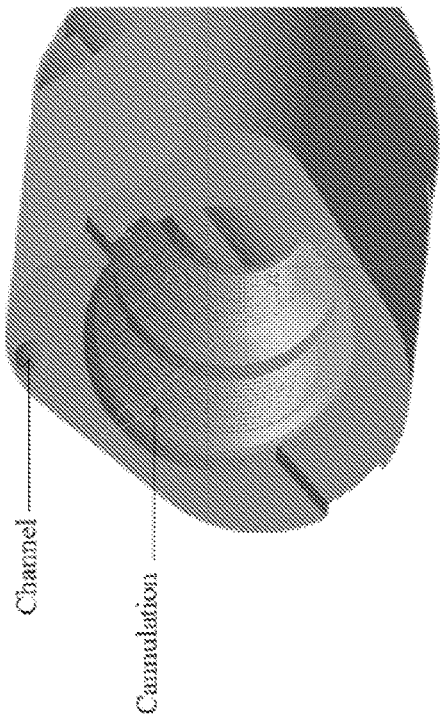
FIG. 46B illustrates an isometric view of an exemplary geometry for an internal sensor probe channel that may be created using additive manufacturing.

FIGS. 46A and 46B illustrates an exemplary geometry for an internal sensor probe channel 302 that may be created using additive manufacturing, and highlights the position of the channel 302 relative to the neutral axis. According to certain embodiments, the size dimensions of the internal sensor probe channel 302 may be minimized to mitigate the risk of adverse fatigue failure. The inclusion of a channel 302 may constitute around an 11% reduction in bending stiffness in the plane of the channel 302, which is unlikely to cause any problems clinically. Further, in the illustrated model, as depicted in FIG. 46A, the "x" axis, which is in the plane of the channel 302, experienced about an 11% reduction in moment of inertia. Additionally, the "y" axis, which is perpendicular to the channel 302, may experience an approximately a 1% reduction in moment of inertia. Moreover, modelling a proximal end of the internal sensor probe channel 302, the moment of inertia with and without the channel 302 is calculated to be X: 878.8 mm$^4$; Y: 990.5 mm$^4$ and X: 993.9 mm$^4$; Y: 993.9 mm$^4$ respectively.

The intramedullary nail 300 depicted in FIG. 43a can be manufactured in a variety of different manners, including, for example, by use of a laser or electron beam three-dimensional (3D) printing. Examples of the laser scanning conditions for a Realiser SLM100 system are outlined in the table shown in FIG. 47. Additionally, the thickness of the wall 306 of the intramedullary nail 300 may be increased, such as, for example, increasing the outer diameter of the wall 306 of the intramedullary nail 300 so as to at least attempt to prevent the internal sensor probe channel 302 from being distorted during heat treatment (HIPPING). For example, the wall 306 of the intramedullary nail may be increased such that the outer diameter of the intramedullary nail is increased by 0.5 millimeters (mm). According to such an embodiment, the additional thickness of the wall 306 may be sacrificed during the post-machining operations.

Additionally, the use of additive manufacturing may permit the intramedullary nail 300 to be manufactured without the use of an exit point or opening that may be associated with the removal of non-sintered powder from the internal sensor probe channel 302. More specifically, micro CT images acquired from testing intramedullary nails 300 after three-dimensional (3D) printing indicated that the internal sensor probe channel 302 did not become contaminated with residual, non-sintered powder, FIG. 43b. Thus, according to certain designs, the intramedullary nail 300 may not include such a removal point or exit that is in fluid communication with the internal sensor probe channel 302. The absence of a removal point or exit that may otherwise be adapted at least for the removal of residual, non-sintered powder may assist in simplifying the design of the internal sensor probe channel 302, as well as the manufacturing of the intramedullary nail 300.

(B) Self-Dynamizing Nail: One of the fundamental concepts in orthopedics is the understanding that appropriate mechanical loading accelerates fracture healing. This is based upon the process of adaptation, according to which bone architecture is constantly optimized in response to the mechanical environment, and which occurs in response to dynamic rather than static loading. More specifically, it is related to the peak strain magnitude and the loading frequency. Although conventional intramedullary nails permit weight bearing forces to be exerted thereon, they often isolate the fracture from compression forces due to the presence of locking screws, whose primary purpose is to prevent rotation. Moreover, intramedullary nails can actually cause cases of fracture of non-union as a result of the fixed distance between the fractured ends and constant load share throughout the healing period imposed on the fracture by virtue of the rigid structure of the intramedullary nails.

Conventional axial dynamization of statically locked intramedullary nails involves the removal of one or more interlocking screws two to three months after initial surgery in an outpatient setting. This approach requires an invasive procedure, and typically has a resolution of around 1 to 5 millimeters (mm), which is often dictated by the width of the slot in the intramedullary nail, and may only be available in one section of the intramedullary nail. A self-dynamizing intramedullary nail would overcome some of these shortfalls, and provide a step-wise improvement in accelerating bone healing through continuous adjustment of the loading share applied to the fracture site. Further, a self-dynamizing intramedullary nail may help prevent the occurrence of delayed healing or non-union of the fracture by permitting appropriate axial movement of the fractured ends of the bone towards each other.

According to certain embodiments, developing a self-dynamizing intramedullary nail may include the following:

(1) Telescopic Intramedullary Nail Components: FIG. 49 illustrates a perspective view of a distal end of a dynamizing intramedullary nail 500 according to an illustrated embodiment of the present invention. As shown, the dynamizing intramedullary nail 500 includes a first section 502a and a second section 502b. Further, the dynamizing intramedullary nail 500 is structured so that the axial position of at least one of the first section 502a and the second section 502b may be adjusted relative to at least the other of the first section 502a and the second section 502b. Such relative changes in the axial positions of the first section 502a and/or the second section 502b may be adapted to at least adjust an overall length of the dynamizing intramedullary nail 500.

Figure 53A:
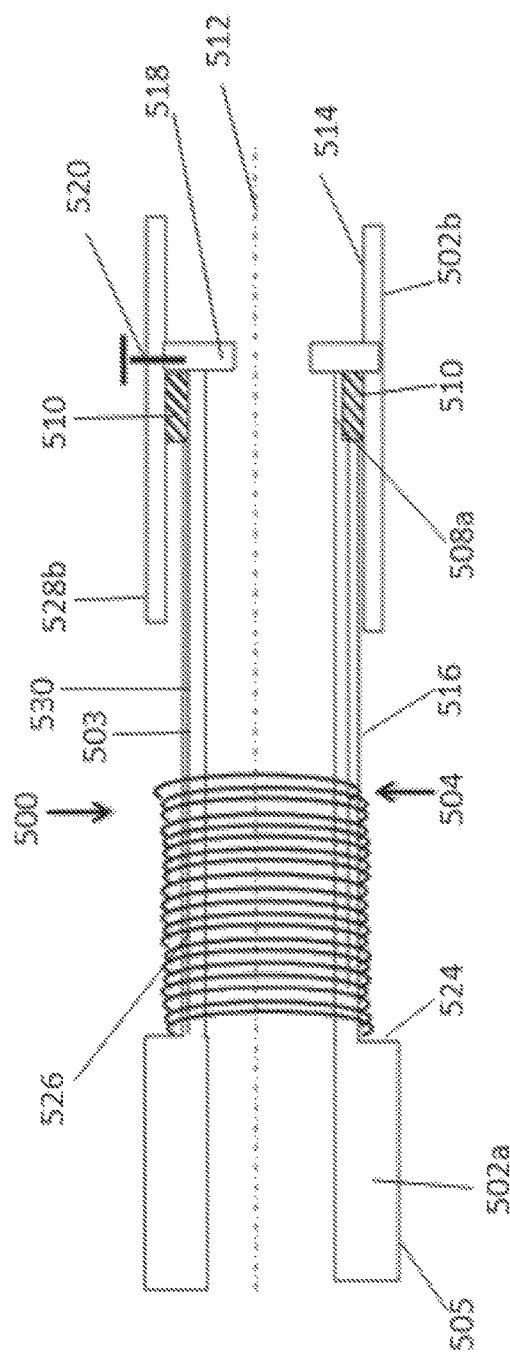
FIGS. 53A and 53B illustrate dynamizing intramedullary nails having telescopic sections that are structured to provide the intramedullary nails with unidirectional and bi-directional translation, respectively.
Figure 53B:
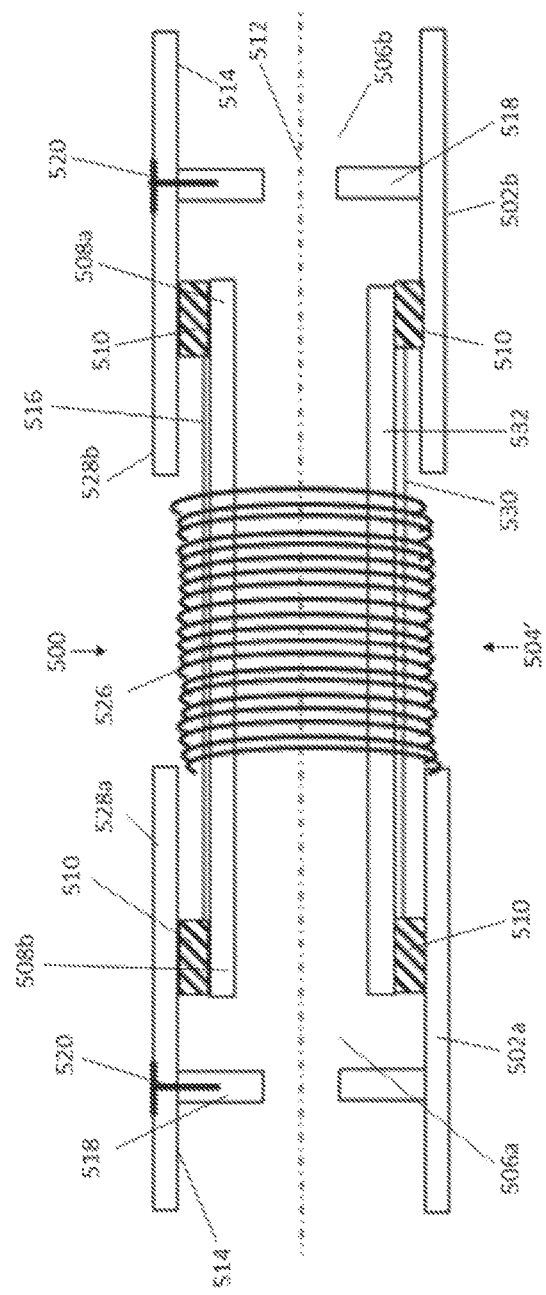
Figure 54:
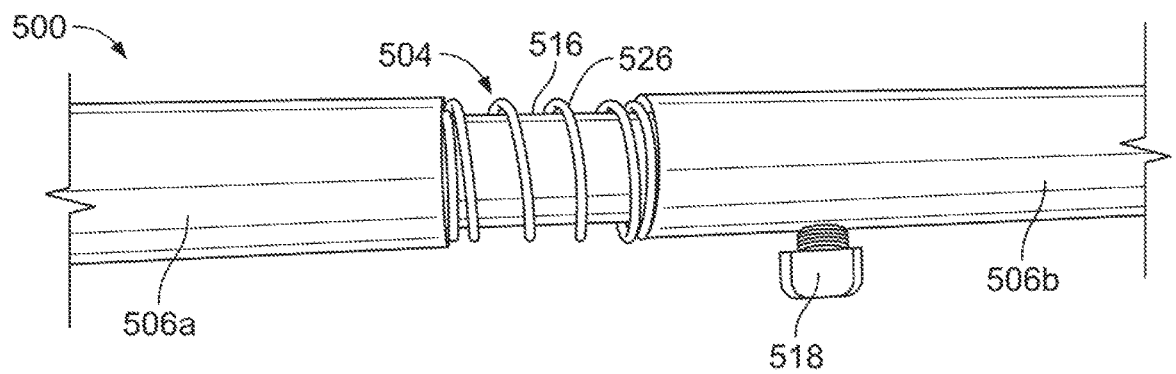
FIGS. 54 and 55 illustrate a dynamizing intramedullary nail having a telescopic section that includes a protrusion in the form of a pin.
Figure 55:
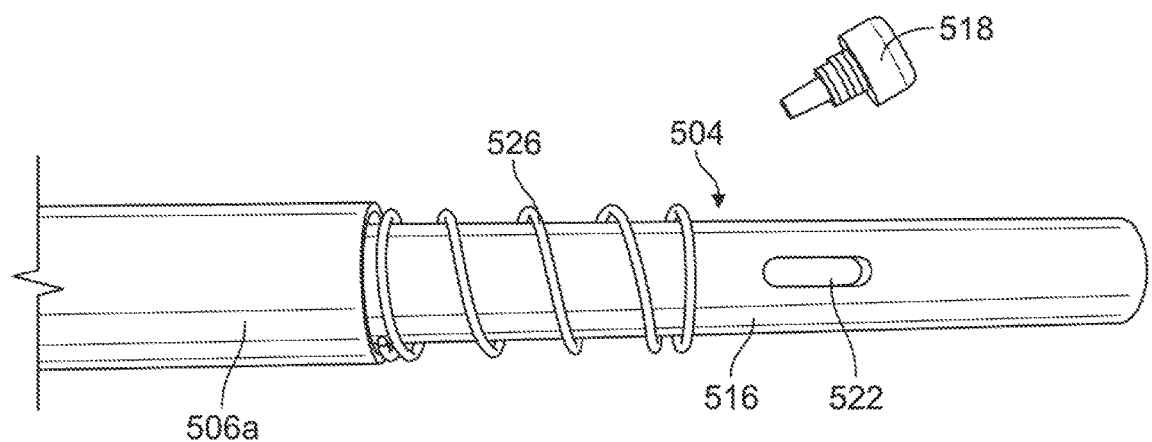

In the embodiment shown in FIG. 49, the dynamizing intramedullary nail 500 includes a telescopic section 504 that is adapted to both facilitate relative axial displacement of the first section 502a and/or the second section 502b of the dynamizing intramedullary nail 500 and retain a connection between the first and second sections 502a, 502b. For example, as illustrated in FIG. 53A, according to certain embodiments, the telescopic section 504 may be a sleeve that extends from an end of the first section 502a or the second section 502b, and which is received in an inner region 506a, 506b of the other of the first and second sections 502a, 502b. In the embodiment illustrated in FIG. 53A, an end portion 503 of the outer wall 505 of the first section 502a may be reduced in size so that a portion of the outer wall 505 is sized to be received in the inner region 506b of the second section 502b. Further, according to certain embodiments, a diameter of the outer wall 505 at the end portion 503 of the first section 502a may be reduced by 1.5 millimeter (mm) diameter so that the outer wall 505 at the end portion 503 has a diameter no greater than 15 millimeters (mm), which may be less than the diameter of at least the portion of the inner region 506b in which the end portion 503 is to be received. Alternatively, as illustrated in FIG. 53B, the telescopic section 504' may be a separate component that is slidingly received in the inner regions 506a, 506b of both the first and second sections 502a, 502b.

Additionally, as indicated by FIGS. 50A-50C, the telescopic section 504 may be located at a variety of different positions along the dynamizing intramedullary nail 500. For example, as depicted, the telescopic section 504 may be in the distal region (FIG. 50A), the midsection (FIG. 50B), or the proximal region (FIG. 50C). Such various positioning may facilitate continuous dynamic loading for different types of fractures.

According to certain embodiments, a distal end 508a and/or proximal end 508b of the telescopic section 504, 504' may include one or more guides or feet 510 that may assist in retaining the first section 502a or the second section 502b in alignment along a central longitudinal axis 512 of the dynamizing nail 500. Alternatively, according to other embodiments, the guides or feet 510 extend from an inner wall 514 of the first or second section 502a, 502b in which the telescopic section 504 is slidingly received. According to other embodiments, an outer wall 516 of the telescopic section 504, 504' may be sized relative to the mating inner region 506a, 506b into which the telescopic section 504 is slidingly received so as to prevent misalignment of the first and second sections 502a, 502b along the central longitudinal axis 512.

Referencing FIGS. 53A-55, the inner region 506a, 506b in which the telescopic section 504 is slidingly received may include one or more protrusions 518 that are configured to limit axial displacement of the telescopic section 504. For example, according to certain embodiments, the protrusions 518 may be positioned to at least limit the degree to which the first and/or second sections 502a, 502b may be axially displaced in a manner that decreases the length of the dynamizing nail 500. Further, according to certain embodiments, one more protrusions 518 may be positioned within the inner region 506a, 506b in a manner that limits the degree to which one or both of the first and second sections 502a, 502b may increase the length of the dynamizing nail 500. The protrusions 518 may take a variety of different forms, including, for example, being a washer that is retained in position by a mechanical fastener 520, such as, for example, a screw or pin, among other protrusions 518 and fasteners 520. According to the embodiment illustrated in FIGS. 54 and 55, the protrusion 518 may be a pin that extends through one of the first and second sections 502a, 502b, and which is received in a slot 522 of the outer wall 516 of the telescopic section 504, 504'. According to such an embodiment a size of the slot 522, such as a length, may limit the distance that one or both of the first and second sections 502a, 502b may be displaced relative to each other. Further, as indicated by FIG. 53A, according to certain embodiments, axial displacement may be limited by a shoulder 524 of the first or second section 502a, 502b that is larger than the size of the adjacent inner region 506a, 506b of the other section 502a, 502b.

(2) Actuator-Controlled Dynamization: The dynamizing nail 500 can be equipped with at least one mechanical actuator 526 that may bias and/or influence the orientation of the dynamizing nail 500. For example, according to certain embodiments, the actuator 526 may be a spring that exerts a force against opposing regions of the first and second sections 506a, 506b to extend or compress the length of the dynamizing nail 500. Referencing FIG. 53A, according to certain embodiments, the actuator 526 may be a spring that is configured to extend a force against the shoulder 524 of the first section 502a, and against an end wall 528 of the second section 502b. Further, referencing FIGS. 53B and 45, according to other embodiments, the actuator 526 may exert a force against end walls 528a, 528b of the first and second sections 502a, 502b, respectively.

Figure 51:
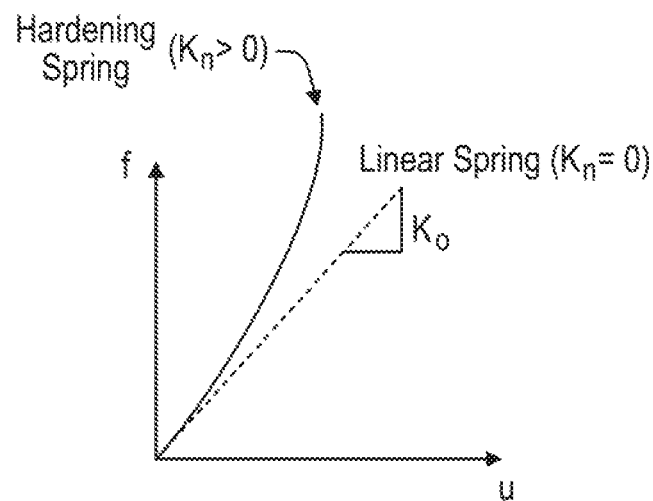
FIG. 51 illustrates an example of linear and non-linear spring force-displacement relationships.

Additionally, the actuator 526 may be a spring that can be linear or non-linear in nature, as indicated in FIG. 51. Compared to linear springs, non-linear or variable rate springs may offer enhanced control and support to shield against excessive impact forces that apply to the bone ends. Examples of non-linear springs include, but are not limited to, conical springs, as well as variable pitch or variable diameter wire springs. Equation 1 represents the general non-linear spring force displacement relationship:

$$K = Ko + Kn \quad \text{(Eq. 1)}$$

where K is the spring rate, Ko is the constant rate (linear part), and Kn is the function of displacement (non-linear part). Additionally, according to certain embodiments, the actuator 526 may further include a dash pot, which, for example, may be used along with the spring to provide more uniform and steady displacement to stabilize the bone ends displacement during weight bearing.

The actuator 526, or a combination of actuators 526, including a spring in combination with other types of actuators, may facilitate or otherwise allow axial movement that is comparable to displacement that may be cause by conventional dynamization of the distal screw. For example, according to certain embodiments, the actuator(s) 526 may facilitate axial displacement of around 1 to 5 millimeters (mm). Additionally, such on-board actuator(s) 526 may also provide controlled, cyclic compression forces, control the size of a gap between the ends of the fractured bone, and provide adjustable intramedullary nail stiffness, thereby at least assisting in making the nail 500 more compliant with the surrounding bone as healing progresses.

Figure 52A:
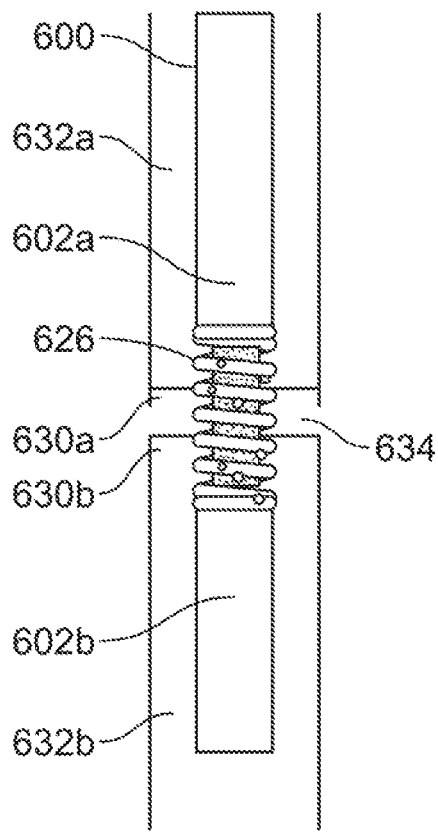
FIGS. 52A and 52B provide schematic illustrations of the degradation of a resorbable polymer of a dynamizing, actuated-loaded intramedullary nail that is positioned in a long bone fracture.
Figure 52B:
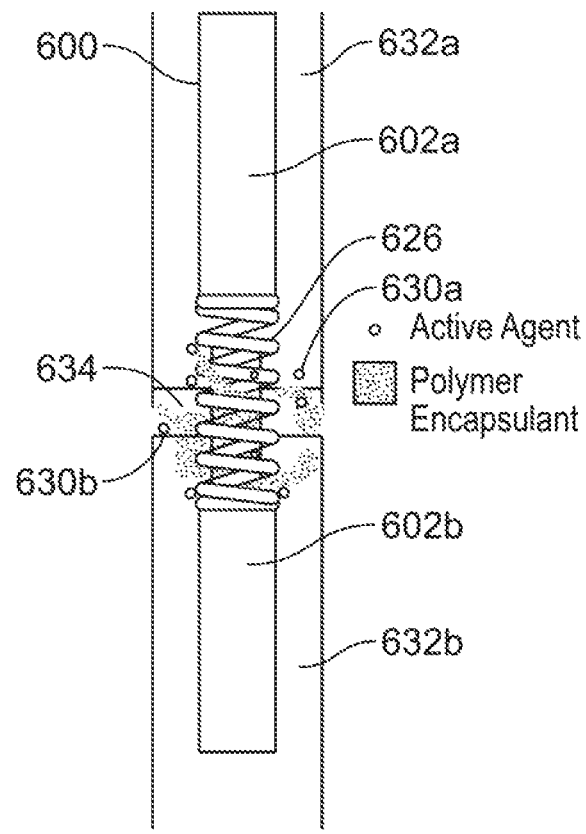

FIGS. 52A and 52B provide schematic illustrations of an actuated-loaded dynamizing nail 600 in a long bone fracture highlighting the degradation of a resorbable polymer. The degradation of the resorbable polymer may also, simultaneously, allow an embedded actuator 626 to engage over time and release one or more bioactive agents capable of stimulating fracture healing and/or reducing infection. According to certain embodiments, the actuator 626 may be a spring (constant or variable rate) that is housed in a resorbably biocompatible polymer encapsulate that simultaneously controls spring compression or a glassy non-resorbably polymer such as polyethylene that relaxes on exposure to an externally applied inductive heater. Examples of suitable resorbably biocompatible polymers may include, but are not limited to, poly(caprolactone), poly(lactic acid), and poly (glycolic acid), among other resorbably biocompatible polymers. Degradation of the polymer may place the actuator 626 in the actuator's 626 relaxed state, thereby providing a continuous cyclic loading to the fractured bone 632a, 632b. Alternatively relaxation of a glassy polymer through inductive heating will also allow the spring to respond under cyclical forces. According to such situations, the ends 630a, 630b of the fractured bone 632a, 632b may be supported when forces are applied to the construct. The bone segments 632a, 632b may then move relative to each other when the polymer encapsulate is no longer capable of carrying a load as a consequence of either inductive heating or degradation. The glassy non-resorbable polymer can prevent the movement of the spring if the inductive heater is removed from the limb allowing the polymer to crystallize and stiffen. The mechanism may be optimized to facilitate just compression of the fracture gap 634 so as to not impede bone healing, which could be delayed if the fracture gap 634 were to be stretched and the bone ends 630a, 630b were pulled apart.

Alternatively, the actuator 626 could be encapsulated in its extended state, allowing the two bone fragments 632a, 632b to be pulled together as the polymer encapsulate degrades away. The actuator 626 and/or the polymer encapsulate can also be filled with active agents or molecules to help facilitate fracture healing and/or reduce bacterial colonization of the implant 600 using growth factors. Such active agents may include, but are not limited to, heavy metal ions, such as, for example, gold and silver.

According to another embodiment, the polymer encapsulated actuator 626 is activated periodically by an external application of physical energy, such as, for example, heat, ultrasound, or electricity. Such activation may facilitate an altering of physical properties of the polymer encapsulate, such as, for example, like Young's Modulus of flexural modulus, among other properties. Such alteration of physical properties of the polymer encapsulate may change the polymer encapsulate from being in a condition in which the polymer encapsulate at least assists in impeding or otherwise resisting relative axial displacement of first and/or second portions 602a, 602b of the nail 600 that may otherwise result in compression or expansion of the length of the dynamizing nail 600. Thus, movement of the actuator 626 can be provided on-demand.

Figure 58A:
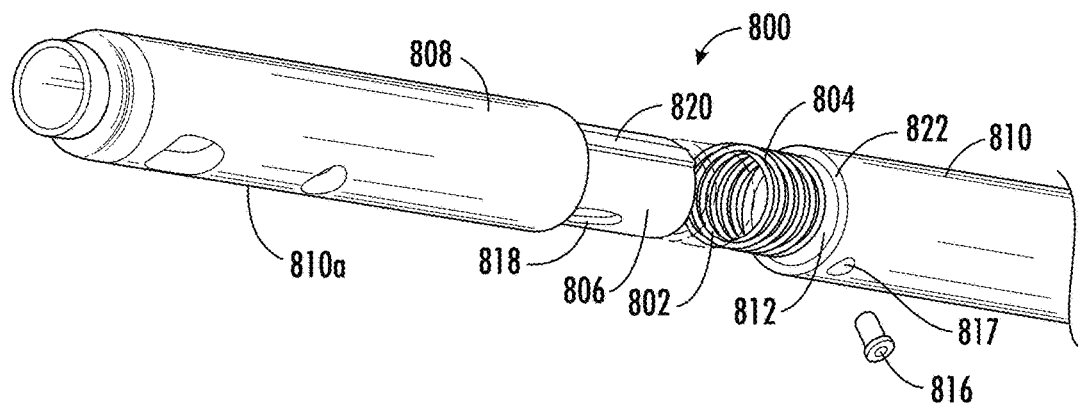
FIG. 58A illustrates an exterior longitudinal view of an end of an intramedullary nail having an activatable shape memory sleeve or collar.

The telescopic section 504, 604 of the dynamizing intramedullary nail 500, 600 can be developed so that it offers either unidirectional or bi-directional translation, as illustrated, for example, in FIGS. 53A and 53B, respectively. Further, rotation of the telescopic section 504, 604, as well as other components of the nail 500 that are coupled to the telescopic section 504, 604, may be presented by flutes 530 on medial and lateral aspects of the inner portion or sleeve 532 of the telescopic section 504, 604. An example of a similar flute 820 and the mating recess 822 is also shown in FIG. 58A. Alternatively, the insertion of the previously discussed protrusion 518, such as, for example, screw or pin, that extends through a machined slot 522 in an inner section of the intramedullary nail 500, 600 can be used to prevent rotation of the first and second sections 502a, 502b while keeping the mechanical actuator 526 located within the recessed region of the nail 500. In this situation, the protrusion 518 could also be mechanically adjusted by a surgeon to control the displacement of the mechanical actuator 526. Additionally, the protrusion 518 may be located in the nail 500 to prevent the fracture gap from increasing.

Figure 56:
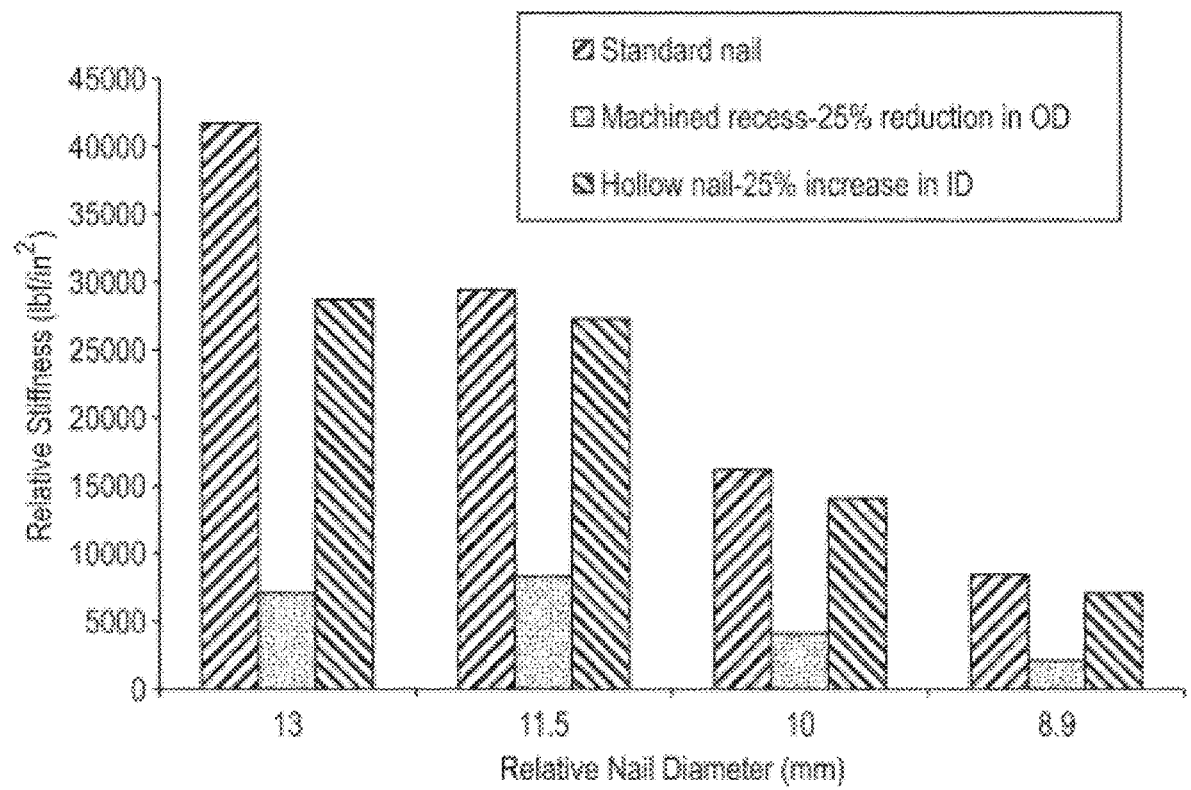
FIG. 56 illustrates the effect of wall thickness on the mechanical stiffness measurements of an intramedullary nail.

FIG. 56 illustrates the effect of wall thickness on the mechanical stiffness measurements of three intramedullary nails, namely (1) a standard nail, (2) a nail having a machined recess in a section of the outside diameter of the nail that provides a 25% reduction in the recessed section of the nail, and (3) a nail having a machined section in a portion of the inner diameter of the nail that provides a 25% increase in the size of the inner diameter of the nail at that machined section the nail. More specifically, FIG. 56 illustrates measured stiffness for each of the three above-identified nails for four external diameters, namely, diameters of 13, 11.5, 10, and 8.9 millimeters (mm). The results suggest that, compared to increasing a section of the internal diameter of the intramedullary nail, machining the external recessed section in the outer surface of the intramedullary nail to create a telescopic section has a more pronounced effect on reducing mechanical bending stiffness of the nail. For example, with the 13 millimeter (mm) diameter nail, increasing the size of the inner diameter for a portion of the nail reduced the nail stiffness from 42,000 pounds-per-square inch (PSI), as experienced by the standard nail, to a stiffness of 29,000 PSI, as experienced by the nail that included the machined inner region that had a larger inner diameter, which was further reduced to a stiffness of 7,000 PSI for the nail that included the recessed section in the outer diameter. Consequently, housing an actuator, such as, for example, the actuator 526, 626, shown in FIGS. 52A-53B, in an inner portion of the intramedullary nail 500, 600 may, compared to actuators that are positioned on the external surface of the nail 500, 600, have a smaller impact on fatigue performance, and may be constructed via use of additive manufacturing.

Figure 57:
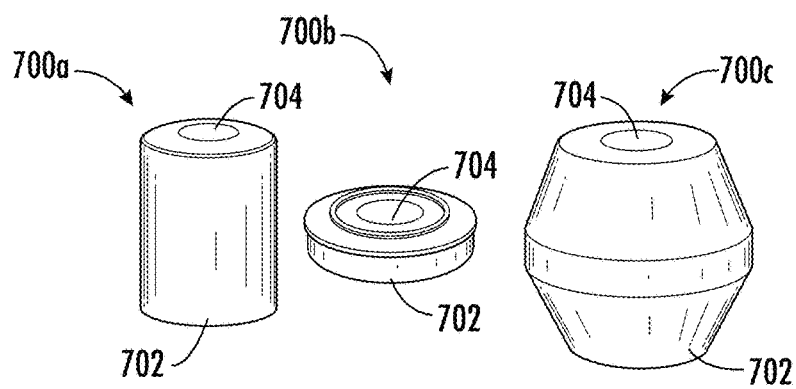
FIG. 57 illustrates perspective views of examples of three bushings that are structured for use with an intramedullary nail to create cyclic loading locally at a fracture site.

(3) Actuation-Controlled Dynamization: According to certain embodiments, the actuator 526, 626, as discussed above with respect to at least FIGS. 52A-53B, may be a bushing that is structured to create cyclic loading locally at the fracture site. The bushing may be constructed from a variety of materials, including, for example, an elastomeric material, such as, for example rubber, among other materials. Moreover, according to certain embodiments, the bushing may be a substitute for at least certain types of actuator 526, 626, such as variable rate springs. Further, as demonstrated by FIG. 57, the bushing 700a-c may have a wall 702 that generally defines an inner region 704 of the bushing 700, and which is size to receive at least a portion of the first and/or second sections 502a, 502b, 602a, 602b of the nail 500, 600. As also indicated by FIG. 57, an outer portion of the wall 702 may have a variety of shapes and sizes.

Figure 58B:
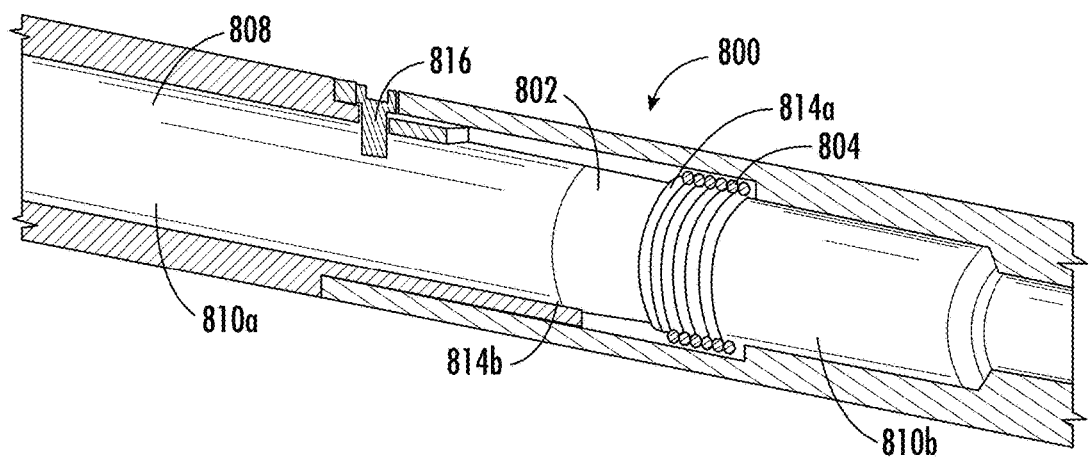
FIGS. 58B and 58C illustrate perspective views of an inner portion of the intramedullary nail shown in FIG. 58A that includes an activatable shape memory sleeve or collar in active and inactive states respectively.
Figure 58C:
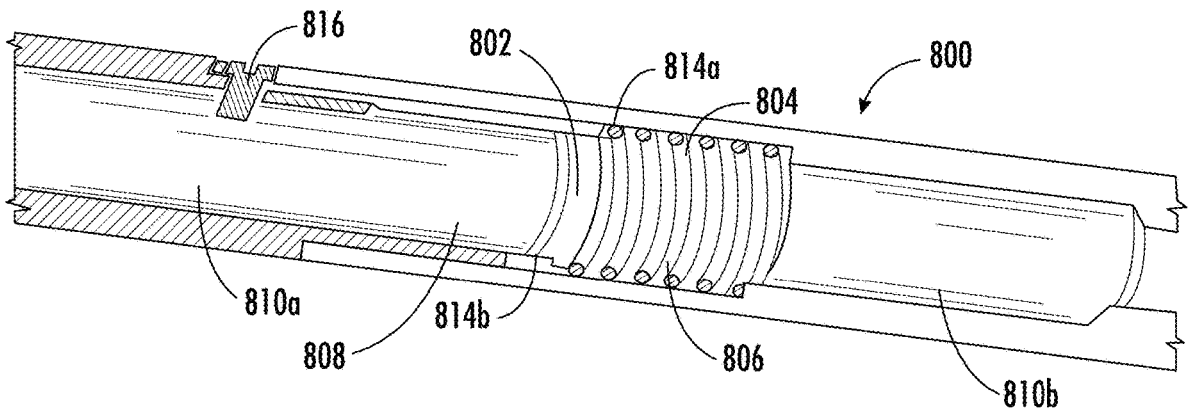

(4) Actuation—Spring and Shape Memory Collar Assembly: According to certain embodiments, a dynamizing intramedullary nail 800 may further include a activatable shape memory sleeve or collar 802, as shown in FIG. 58A-58C, that is structured to control displacement of an actuator 804, such as, for example, control the displacement experienced by spring actuator and the resultant forces exerted on the bone. As shown in FIGS. 58A-58C, according to certain embodiments, the sleeve or collar 802 may be positioned about a telescopic section 806 of the nail 800 that is sized to be received in the inner region 812 of the first section 810a and/or second section 810b of the nail 800. According to the illustrated embodiment, a first end 814a of the sleeve or collar 802 may be positioned to abut against an adjacent end of the actuator 804, while a second end 814b of the sleeve or collar 802 may be positioned to abut against an adjacent portion of the second section 810b. Further, in the embodiment illustrated in FIGS. 58A-58C, the sleeve or collar 802 and actuator 804 are located in the distal region of the nail 800. However, the sleeve or collar 802, along with the actuator 804, may be positioned at a variety of other locations along the nail 800.

The sleeve or collar 802 may be a shape memory collar, such as, for example, a shape memory polymer or metal allow that is trained to contract when activated, such as, for example, upon being heated above body temperature, to accommodate fixed translation of the actuator 804. Alternatively, the sleeve or collar 802 may be constructed from a piezoelectric material that, upon being activated from an inactive state to an active state, deforms in response to an externally applied voltage in a manner that increases or decreases a size of the sleeve or collar 802. Thus, the sleeve or collar 802 may provide a locking mechanism for the self-dynamizing nail 800 as the sleeve or collar 802 is adjusted from being in an active or inactive state. Therefore, the sleeve or collar 802 may have a first size, such as a length (as indicated by "L" in FIG. 58A) when in one of the active or inactive state that is larger than a second size of the collar or sleeve 802 when the collar or sleeve 802 is in the other of the active or inactive state. Further, the overall length of the sleeve or collar 802 and the actuator 804 assembly or combination may be generally constant in regardless of whether the sleeve or collar 802 is in the inactive state and or active state. Such differences in the size of the sleeve or collar 802 when the sleeve or collar 802 is in the active or inactive state may alter whether the actuator 804 is in a compressed or at least partially uncompressed state.

For example, according to certain embodiments, as shown in FIG. 58B, the actuator 804 may be in its compressed state when the shape memory sleeve or collar 802 has a first size or length that at least assists in compressing the actuator 804 to a compressed state. Conversely, as shown in FIG. 58C, when the sleeve or collar 802 is actuated such that the shape memory of the sleeve or collar adjusts the sleeve or collar 802 from the first size to a second, smaller size, the spring actuator 804 may expand from the compressed state to an extended, or partially extended state, and thereby at least assist in accommodating an adjustment, even if temporary, in a corresponding length of the dynamizing nail 800.

Additionally, displacement of the actuator 804, and thus adjustments in the relative positions of the first and second sections 810a, 810b, may be controlled by the use of an adjustable controller 816, such as, for example, a pin or screw. As shown in the embodiment illustrated in FIG. 58A, the adjustable controller 816 may be received in an aperture 817 in the second section 810b, as well as in a slot 818 in the outer wall 808 of the first section 810a that is sized to be received in the inner region 812 of the second section 810b. According to such an embodiment, the controller 816 may be mechanically adjustable by a surgeon, and may be configured to prevent fractured bone segments from becoming pulled apart during motion of the actuator 804. Additionally, according to certain embodiments, the controller 816 may be tightened so as to prevent the relative displacement of the first and second sections 810a, 810b.

(5) Activation of Counterbalancing Springs Using a Resorbable Encapsulate.

Figure 59:
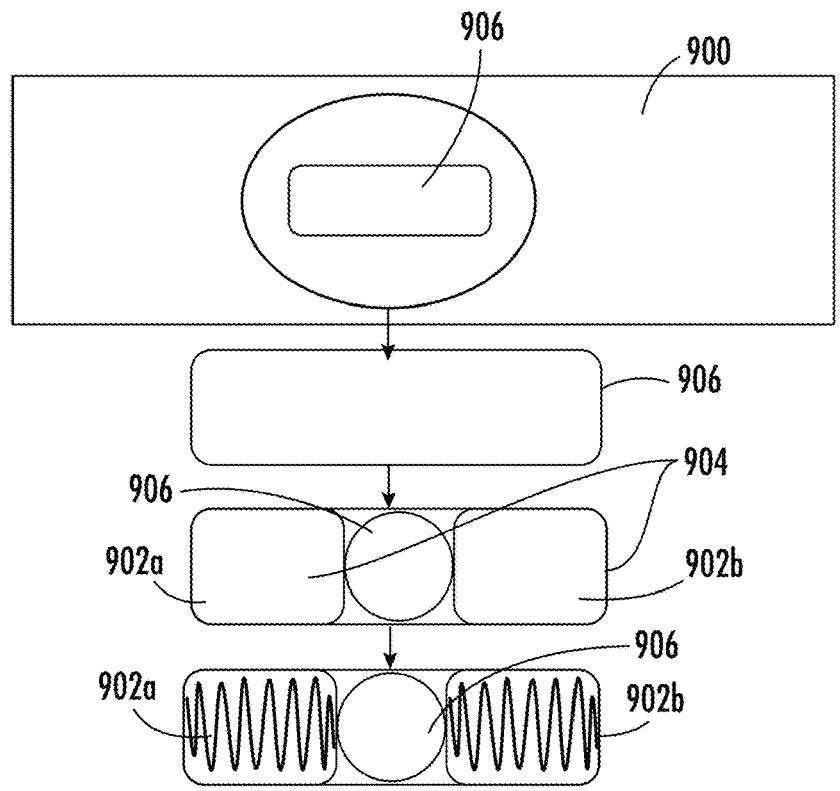
FIG. 59 illustrates a schematic of views of various portions of a dynamizing intramedullary nail that includes a pair of opposing, encapsulated biasing elements.

Referencing FIG. 59, according to certain embodiments, the dynamizing intramedullary nail 900 may include one or more biasing elements 902a, 902b, such as, for example, springs, which are each encapsulated in resorbably housings 904. The purpose of the counterbalancing springs is to shield the fractured bone from excessive and impact forces that may disturb the healing process. Further, the encapsulated biasing elements 902a, 92b and intermediary element 906 may be sized to be positioned within a slot 906 in the nail 900. This slot can be located at either the proximal, mid shaft or distal region of the nail. The resorbable housing 904 may prevent activation of the biasing elements 902a, 902b. In such a situation, the biasing elements 902a, 902b may exert, via the resorbably housings 904, a force against an intermediary element 906, such as for example, a portion of a screw, which is positioned between the resorbable housings 904. As the resorbably housings 904 degrade, the associated biasing element 902a, 902b of the degraded resorbably housing(s) 904 may be able to be in an active state in which the biasing element(s) 902a, 902b extend toward, and/or to, partial or full expanded or relaxed states, and wherein the biasing elements 902a, 902b may provide support only for compression of the fracture gap. The use of such biasing elements 902a, 902b is advantageous in making the nail 900 self-adjusting and controlled, and shielding the fracture from excessive and impact forces that may disturb the healing process.

Figure 60:
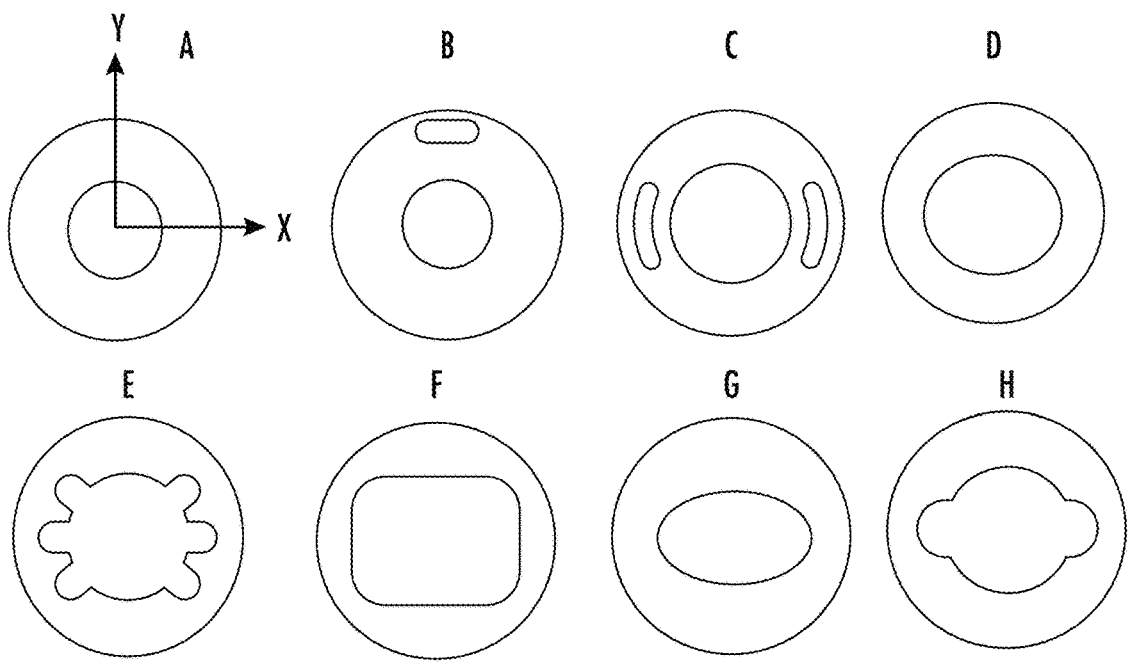
FIG. 60 illustrates a standard circular cross section intramedullary nail and examples of cross sectional geometries of intramedullary nails that may reduce bending stiffness in the anterior-posterior plane while relatively preserving the stiffness in the orthogonal medial-lateral plane.

(C) Variable Stiffness Nail in the Anterior-Posterior (A/P) and Medial-Lateral (M/L) Planes: the ability to independently control bending or torsional stiffness in either the A/P or M/L plane may permit an intramedullary nail to be structured to attain optimal fracture healing or reduced the incidence of periprosthetic fracture. A localized reduction in bending stiffness at the distal end of the nail could prevent the risk of per-prosthetic fracture if the patient received a joint replacement. The cross-sections depicted by items B-H in FIG. 60 provide examples of cross sectional geometries of intramedullary nails that may reduce bending stiffness by about 20% in the A/P plane while relatively preserving the stiffness in the orthogonal M/L plane. Again, this cross-sectional geometry may only be amendable to additive manufacturing Moreover, compared the circular cross section shown in item A in FIG. 60, the various cross sections shown in items B-H in FIG. 60 may provide the following reductions in moment of inertia in the A/P plane: 11% for item B; 17-28% for item C; 7% for item D; 8% for item E; 14% for item P; 7% for item G; and, 10% for item H.

Figure 61A:
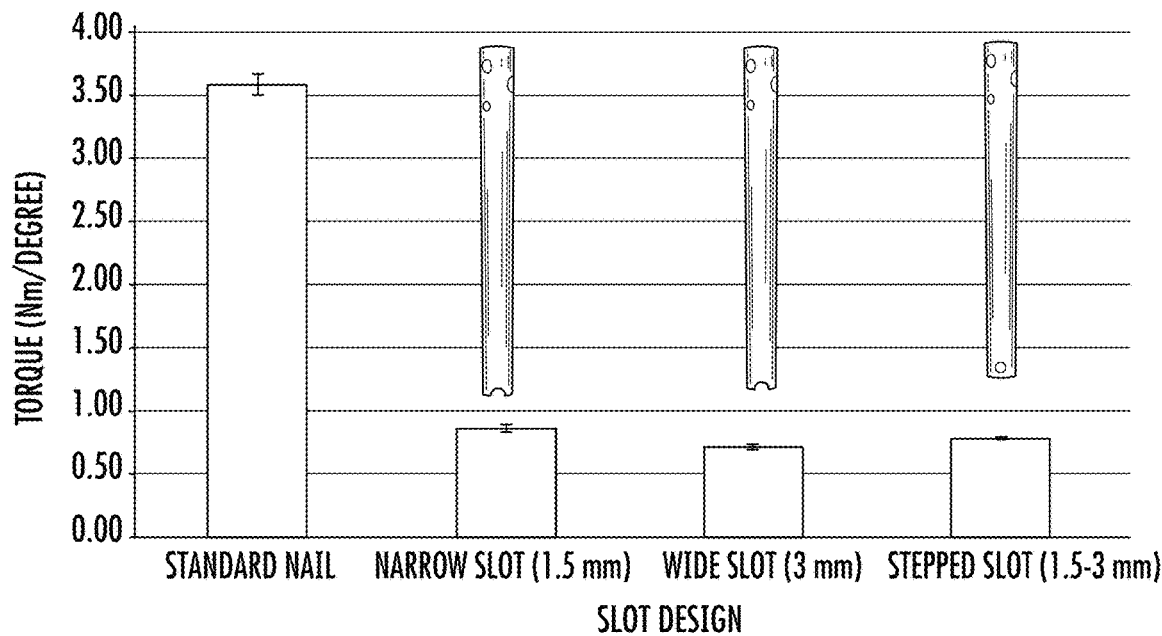
FIGS. 61A and 61B illustrate torsional and bending stiffness data based on a standard 10 millimeter outside diameter Trigen Meta tibial nail and 10 millimeter outside diameter Trigen Meta tibial nails that have different sized slots on an outer surface of the nails.
Figure 61B:
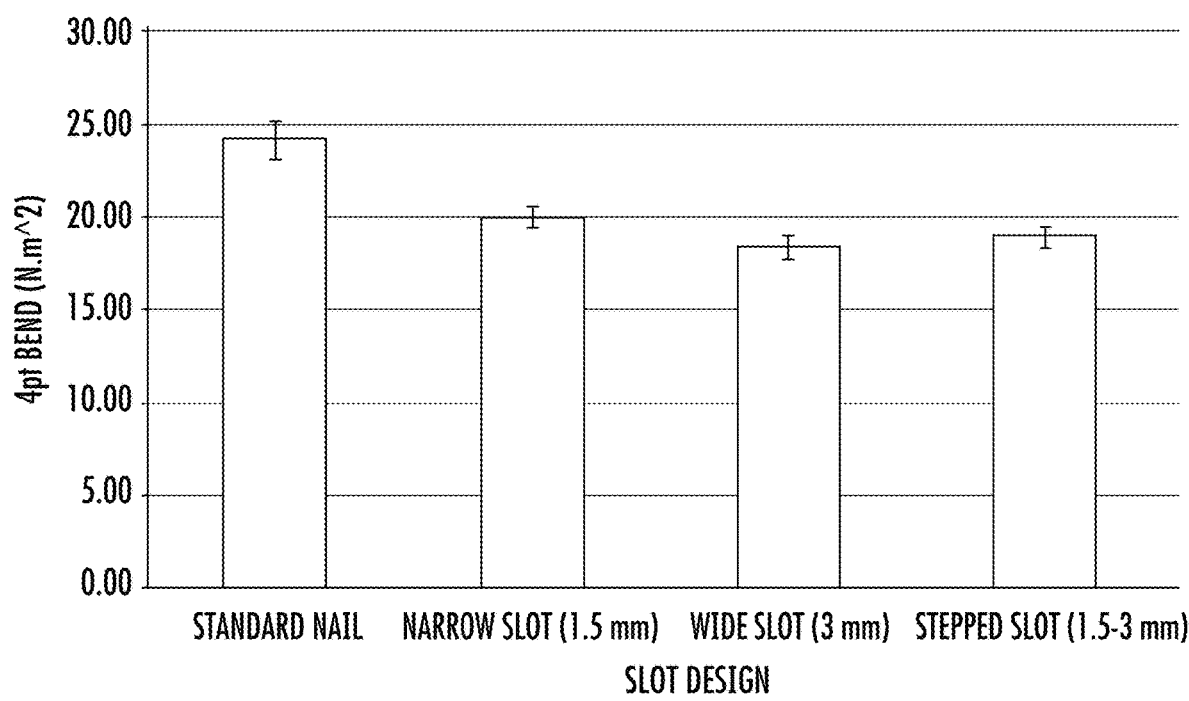

FIGS. 61A and 61B provide torsional and bending stiffness data based on a standard 10 millimeter Trigen Meta tibial nail and 10 millimeter Trigen Meta tibial nails that have different sized slots on an outer surface of the nails. Moreover, FIGS. 61A and 61B illustrate the sensitivity of cross-sectional geometry on mechanical performance. As depicted, compared to a standard nail, the inclusion of a narrow (1.5 millimeter), a wide (3 millimeter), or stepped slot (1.5-3 millimeter) on the outside of the nails in the A/P plane reduced torsional stiffness from 3.5 Nm/Degree to less than 1 Nm/Degree. Similarly, bending stiffness was also reduced from 23 Nm$^2$ to less than 20 Nm$^2$. Although the data depicted by FIGS. 61A and 61B related to the inclusion of slots that located on the outside of the nail, the data generally highlights the principle of adjusting the stiffness of the nail in a particular anatomical plane.

(D) Internal Geometry Offering Lower Stiffness Implant for Larger Patients: The ability to fill the intramedullary canal for the larger sized patient with a lower stiffness implant may help accelerate healing of the fracture, especially if the bone is pathological. To avoid any complications associated with externally-designed geometrical features such as bony ingrowth, a number of designs that exploit the design freedom of additive manufacturing are outlined below.

Figures 62, 63:
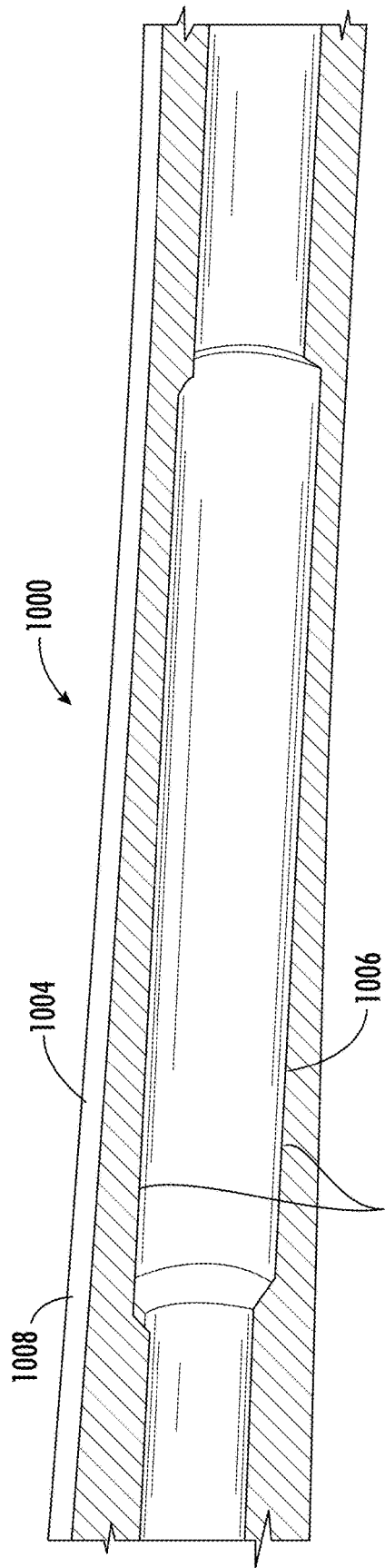
FIG. 62 illustrates a three-dimensional (3D) CAD intramedullary nail model in a cross sectional view that includes a tapered inner wall at a mid-section of the nail.
FIG. 63 illustrates a table identifying theoretical bending and torsional stiffness in the mid-section of an intramedullary nail that has a tapered inner wall.

FIG. 62 illustrates a cross section view of an intramedullary nail 1000 having a tapered inner wall 1002 at a mid-section 1004 of the nail 1000 that is located between the distal and proximal screw holes of the nail 1000. According to certain embodiments, the tapered mid-section 1002 may be dovetail shaped. Such a tapered configuration on the inside surface 1006 of the cannulation of the nail 1000 may have a pronounced effect on torsional stiffness, which could have a beneficial impact if this design feature intersects the fracture site. Further, such a nail 1000 could allow rapid uptake of load during the early stage of fracture healing without comprising the fatigue properties of the nail 1000.

FIG. 63 provides a table identifying theoretical bending and torsional stiffness in the mid-section 1004 of the intramedullary nail 1000 ("Custom wall thickness") with a tapered inner wall 1002 and an outer diameter 1008. For comparative purposes, the theoretical values for the Trigen Meta tibial nail ("Standard") is also included in the table in FIG. 63. The reduction in theoretical bending and torsional stiffness for the intramedullary nails 1000 having a tapered inner wall 1002 for the three identified outer diameter 1008 sizes, namely an outer diameter of 10 millimeter (mm), 11.5 millimeter, and 13 millimeter, assuming a constant wall thickness of 1.5 millimeter, is 17%, 27% and 21.3% respectively. The theoretical bending stiffness for a 10 millimeter (mm) outer diameter nail 1000 equipped with a customized, tapered inner wall 1002 in the mid-section 1004 is calculated to be 42.5 N·m$^2$. This customized section of the nail 1000 has a bending stiffness comparative to: a solid profile AO Universal Tibial Nail (Synthes) having a 9 millimeter outer diameter, which was determined to be 40 N·m$^2$; an un-slotted profile nail, e.g. a B&K nail, which is determined to be 34 N·m$^2$; and, a slotted profile nail having a wall thickness 1.2 millimeter, e.g. a K&S nail, which is determined to be 40 N·m$^2$. As also shown in FIG. 63, in torsion, the theoretical torsional stiffness of a customized nail 1000 having a tapered inner wall 1002 in the mid-section 1004, a 1.5 millimeter (mm) wall thickness, and 10 millimeter outer diameter is 29.8 N·m$^2$. This stiffness is comparable to a 9.0 millimeter (mm) outer diameter Russell Taylor Delta Nail (22.5 N·m$^2$) and an 8.5 millimeter (mm) outer diameter Trigen Meta tibial nail (18.4 N·m$^2$).

Figure 64A:
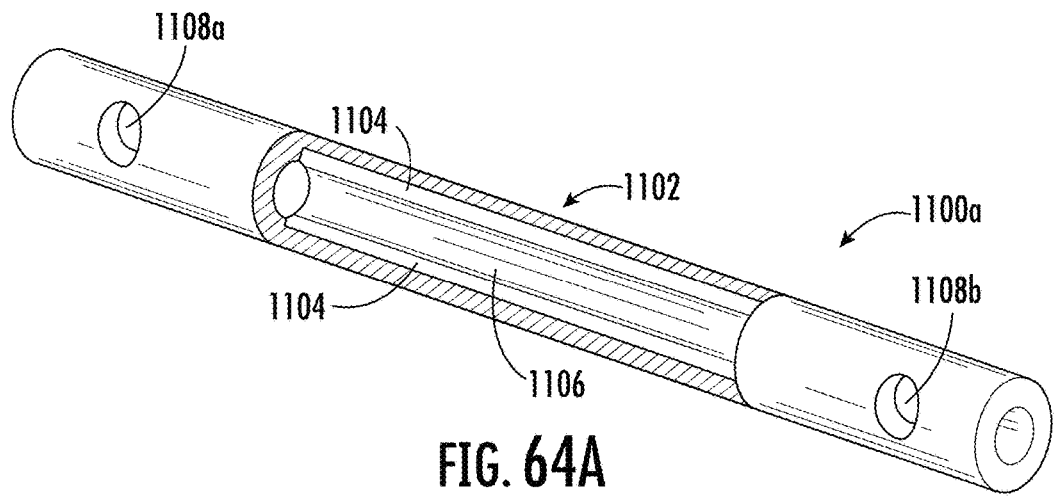
FIG. 64A illustrates a three-dimensional (3D) CAD model of an intramedullary nail in partial perspective and cut away view, the intramedullary nail being equipped with circumferentially arranged internal flutes in an inner wall section of the nail.
Figure 64B:
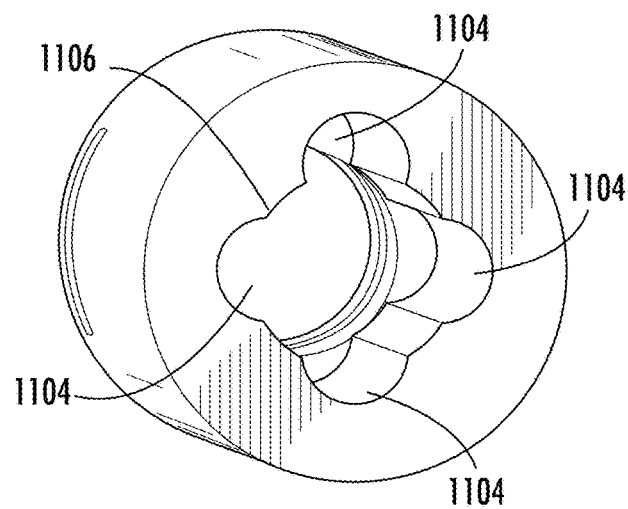
FIG. 64B illustrates a cross sectional view of a portion of the mid-section of the intramedullary nail shown in FIG. 65A.

FIGS. 7A-7D, 64A-66 and 69 provide additional implant designs that offer reduced stiffness for larger patients. Such designs may include recesses into or though the wall of the nail. For example, FIG. 64A illustrates a cutaway view, and FIG. 64B illustrates a cross sectional view of a portion, of a mid-section 1102 of an intramedullary nail 1000 that is equipped with circumferentially arranged internal flutes 1104 in an inner wall section 1106 of the nail 1100. The flutes 1104 may be positioned in the mid-section 1102 of the nail 1100 between the distal and proximal screw holes 1108a, 1108b. The inclusion of flutes 1104 may reduce the theoretical bending stiffness of the nail 1100. For example, a standard 10 millimeter outer diameter, 4.8 millimeter internal diameter nail having a circular cross sectional shape may have a bending stiffness of 51.2 N·m². However, the inclusion of flutes 1104 to such a nail may reduce the bending stiffness to 48.5 N·m².

Figure 7A:
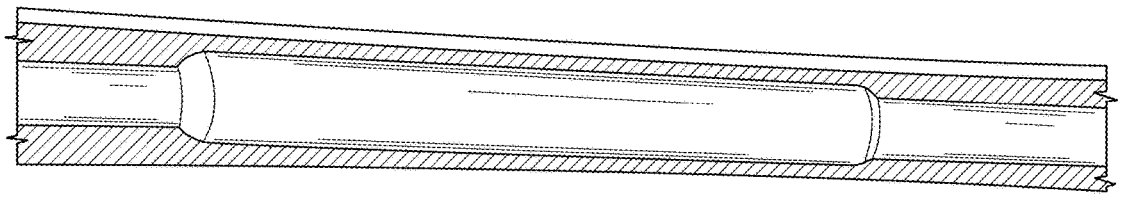
FIG. 7A illustrates a three-dimensional (3D) CAD intramedullary nail model that includes a tapered inner wall section in cross-section view.
Figure 7B:
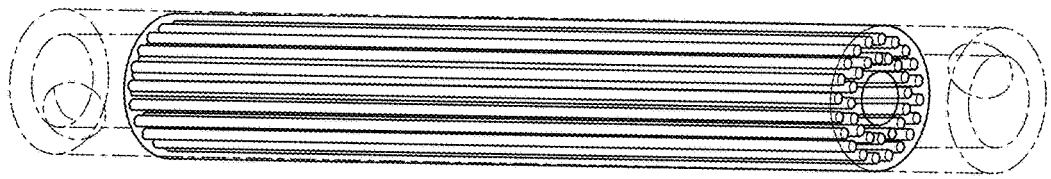
FIG. 7B illustrates a three-dimensional (3D) CAD intramedullary nail model in partial phantom view and which includes a porous or channel inner structure in the wall of the intramedullary nail.
Figure 7C:
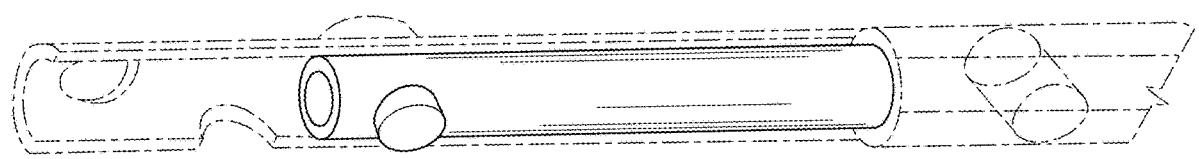
FIG. 7C illustrates a three-dimensional (3D) CAD intramedullary nail model in a perspective, partial cut away view that includes a detachable inner section.
Figure 7D:
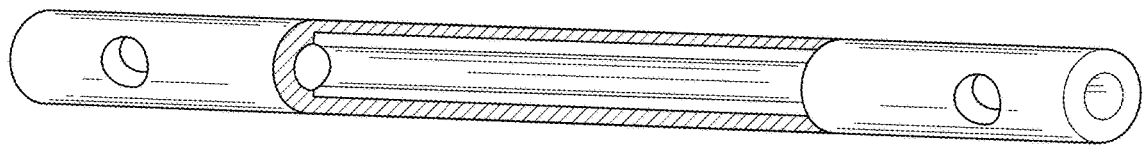
FIG. 7D illustrates a three-dimensional (3D) CAD intramedullary nail model in a partial cutaway view that includes an internal fluted section.
Figure 8:
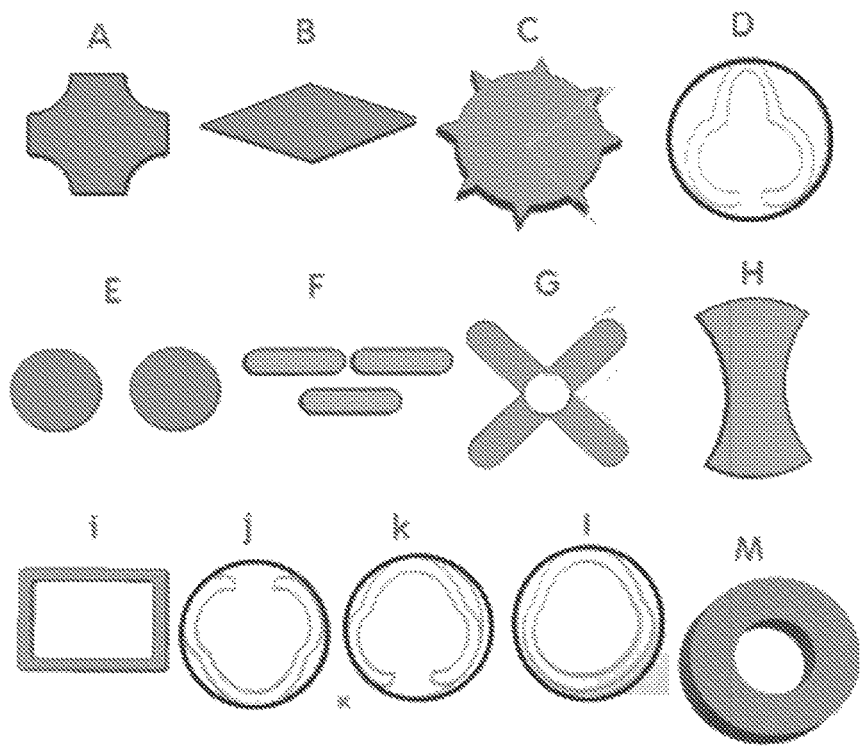
FIG. 8 illustrates examples of optimal cross-sectional geometries for an intramedullary nail.
Figure 65:
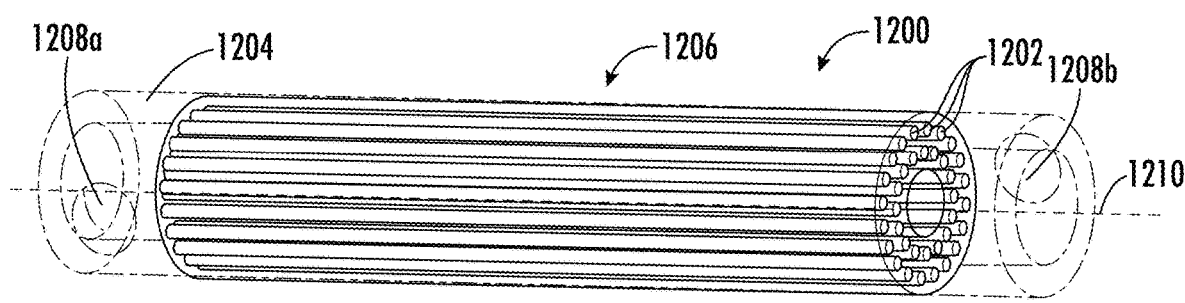
FIG. 65 illustrates three-dimensional (3D) CAD model of an intramedullary nail in a partial phantom view, the intramedullary nail including an ordered porous or channel inner structure in the wall of the intramedullary nail.
Figures 66, 67:
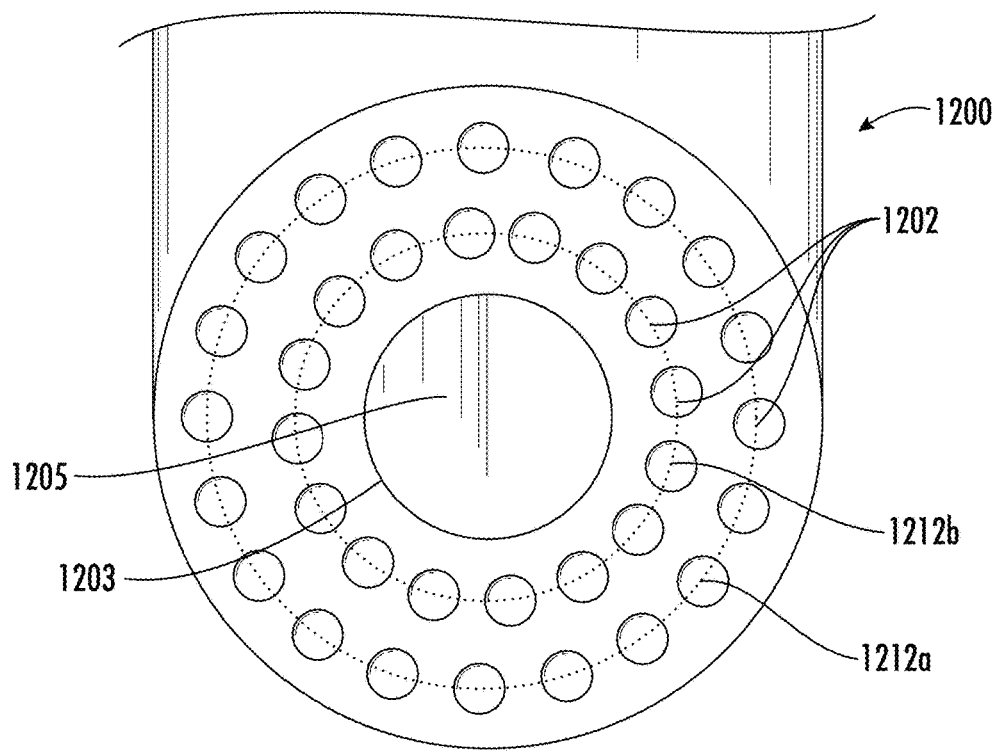
FIG. 66 illustrates an end view of a portion of the intramedullary nail shown in FIG. 65 taken from a mid-section of the intramedullary nail.
FIG. 67 illustrates a comparison of the theoretical bending and torsional stiffness of a standard intramedullary nail and an intramedullary nail having a porous or channel inner structure, as shown in FIGS. 66 and 65.

Referencing FIGS. 7B, 65 and 66, according to other embodiments, an intramedullary nail 1200 may include a series of circumferentially arranged open channels 1202 that extend within, and through, the wall 1204 of the nail 1200. The wall 1204 may include an inner wall section 1203 that generally defines a hollow inner region 1205 of the nail 1200. The channels 1202 may extend along a mid-section 1206 of the intramedullary nail 1200, such as, for example, in a region between distal and proximal screw holes 1208a, 1208b in the nail 1200. Further, the channels 1202 may be generally parallel to a central longitudinal axis 1210 of the nail 1200. The channels 1202 may also be arranged along one or more diameters. For example, as shown in FIG. 66, according to certain embodiments, at least a portion of the channels 1202 may be arranged about a first, outer diameter 1212a while other channels are arranged about a second, smaller inner diameter 1212b. The channels 1202 may also have a variety of different shapes and sizes, such as, for example, being cylindrical in shape. While the above example, has been discussed in terms of the mid-section 1206 of the nail, the discussed channel 1202 structure may also be used with other portions of the implant so as to ensure that the fracture site can intersect with a low modulus portion of the nail 1200.

According to an exemplary embodiment, the nail 1200 shown in FIGS. 65 and 66 may include 35 circumferentially arranged channels 1202 that have approximately a 1 millimeter diameter circular cross-sectional shape. The inclusion of such channels 1202 in the wall 1204 of a nail 1200 that has a 13 millimeter outside diameter and a 4.8 millimeter diameter inner wall section 1200 may reduce the volume fraction of material, such as, for example, titanium, in the wall 1204 of the implant from 100% to 76%, with the volume fraction of the voids in the wall 1204 provided by the channels 1202 being 24%, thereby creating a lower porosity structure. As illustrated in the table shown in FIG. 67, in this situation, the theoretical bending and torsional stiffness of the nail 1200 may be reduced from 155.9 N·m²/119.2 N·m² to 110.1/83.4 N·m² respectively.

Figure 68:
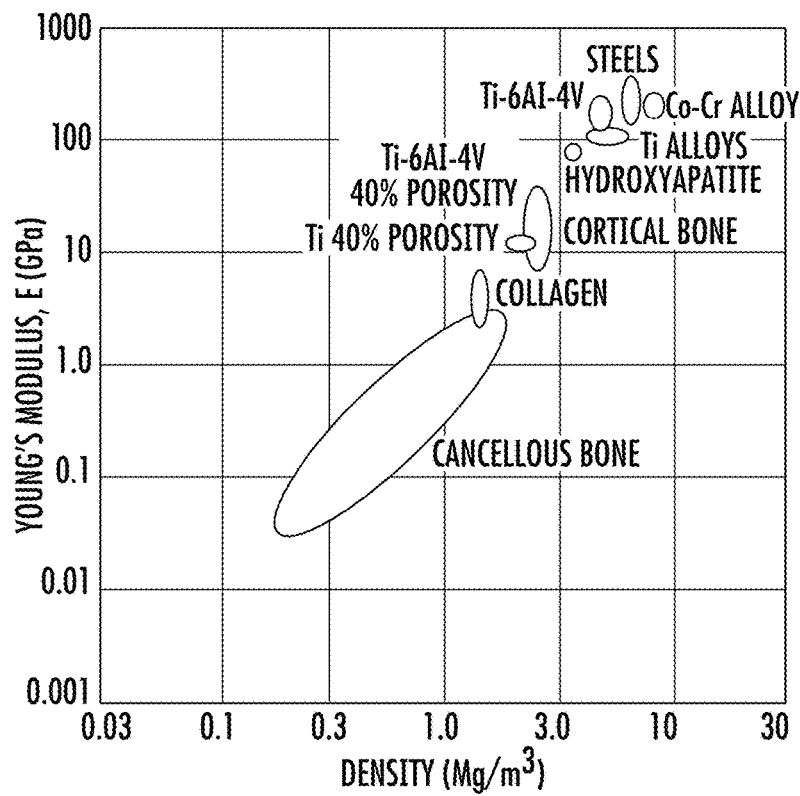
FIG. 68 illustrates an elastic modulus versus density diagram that provides data for cancellous bone, collagen, Ti 40% porosity, cortical bone, TI-6Al-4V 40% porosity, Ti alloys, CO—Cr alloy, steels, and Ti-6A-4V.

FIG. 68 provides an elastic modulus versus density diagram that may be used to estimate the degree of porosity required to match the elastic modulus of cortical bone. As indicated, the Elastic Moduli for nonporous Titanium-64, 316 stainless steel, and cobalt chromium are 114 gigapascal (GPa), 193 GPa and 235 GPa, respectively. Further the density of bone, Ti-64 and 316 stainless steel may be 2.4 g/cm³, 4.7 g/cm³ and 8.8 g/cm³, respectively. Using the rule of mixtures for composite materials, increasing the porosity of titanium-64 alloy from 0 to 40% reduces the elastic modulus from 114 GPa to 68.4 GPa, which is closer to the upper limit of cortical bone (40 GPa). Consequently, a porous titanium implant may help reduce the stiffness mismatch between the implant, such as an intramedullary nail, and bone tissue, and thereby reduce stress shielding. However, increasing porosity and pore size may result in a reduction of the implant mechanical properties. Thus, the balance between mechanical properties and biological performance may vary for different implant applications.

Figure 69:
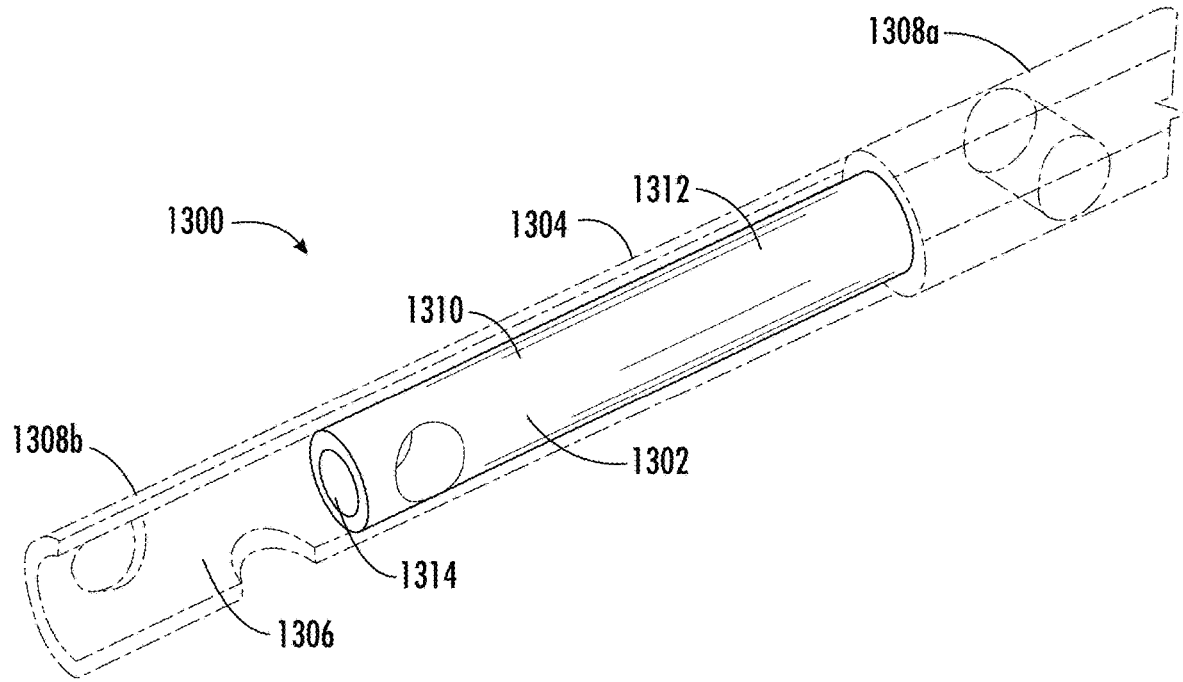
FIG. 69 illustrates a perspective, partial cut away view of a portion of three-dimensional (3D) model of an intramedullary nail that includes a detachable inner section.

Referencing FIG. 69, according to another embodiment, the elastic modulus of an intramedullary nail 1300 can also be modulated by housing a detachable inner section 1302 in at least a portion of an outer section 1304 of the nail 1300. The inner section 1302 may be fixed to the inside surface 1306 of the intramedullary nail 1300 at one of the proximal end 1308a and distal end 1308b of the nail, but is detachable via a locking screw (not shown) at the other of the proximal end 1308a or distal end 1308b of the nail 1300. As shown, the inner section 1302 includes a wall 1310 having an outer portion 1312 and an inner portion 1314, the inner portion 1314 of the wall 1310 generally defining a hollow inner region of the inner section 1302. The outer portion 1312 of the wall 1310 is sized to accommodate lateral displacement of the inner section 1302 about the outer section 1304 of the nail 1300, as well as displacement of at least connected portions of the proximal end 1308a and the nail 1300 relative to distal end 1308b of the nail 1300, or vice versa.

Such a variable modulus nail 1300 may enable the implant to present a higher stiffness during fracture healing, which may be useful for at least severely comminuted fractures where greater nail stiffness and stabilization are required during initial healing. However, the configuration of intramedullary nail 1300 may enable, once the fractured bone has healed, a reduction in the elastic modulus of the nail 1300 in a minimally invasive fashion and without the need for removing the nail 1300. For example, if another, stiff intramedullary nail were to be removed after bone healing, loading on the bone could increase significantly, which could lead to re-fracture in situations where there was significant patient activity. Such situations may include osteoporotic fractures where high-rigidity nails, such as, for example, nails having approximately 300% of the bending rigidity of an osteoporotic femur, can reduce bone strength. However, after fracture healing, a low-rigidity nail, such as, for example, the intramedullary nail 1300 of FIG. 69 with the detachable inner section 1302, may reduce the effects of stress shielding, and may result in less bone resorption than relatively stiffer nails. For example, FIG. 70 illustrates a table that provides a comparison between the bending and torsional stiffness of standard Trigen Meta tibial nails having 8.5 millimeter (mm) and 10 mm outer diameters, and a "custom" nail similar to the nail 1300 illustrated in FIG. 69 that has a 10 millimeter outer section. Further, the "custom" nail referenced in FIG. 70 has an inner section 1302 having wall 1310 that includes an outer portion 1312 having a 7.6 millimeter diameter and an inner portion 1314 having a 4.8 mm diameter. As shown in FIG. 70, the torsional and bending stiffness of such a nail may be 8.5/26.2 N·m² and 12.1/37.3 N·m² respectively.

While the implants and methods set forth above have been described in association with an orthopedic intramedullary nail, it should be understood that the implants and methods may also be used in other technological areas and/or in association with other types of orthopedic implants. Various changes and modifications to the described embodiments described herein will be apparent to those skilled in the art, and such changes and modifications can be made without departing from the spirit and scope of the invention and without diminishing its intended advantages. Additionally, while the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

The invention claimed is:

1. A method for manufacturing an orthopedic device comprising:
   forming an orthopedic component via an additive manufacturing process by:
      laser sintering a titanium powder to form a first plurality of laser sintered layers that define a predetermined shape for the orthopedic component; and
      selectively re-melting the first plurality of laser sintered layers, wherein the re-melting comprises a laser raster wherein a portion of a layer of the first plurality of laser sintered layers is double scanned;
   heat treating the orthopedic component; and
   after the heat treating, machining the orthopedic component to form the orthopedic device, wherein a wall of the orthopedic device has a variable thickness to alter a stiffness of the orthopedic device.

2. The method of claim 1, wherein heat treating the orthopedic component comprises:
   subjecting the orthopedic component to hot isostatically pressing utilizing a temperature of at least 1000° Celsius; and
   cooling the orthopedic component at a cooling rate between 0.24° and 72° Celsius/minute.

3. The method of claim 1, wherein forming the orthopedic component comprises forming the orthopedic component with a non-circular cross-sectional shape.

4. The method of claim 1, wherein the orthopedic device comprises an intramedullary nail.

5. The method of claim 1, wherein re-melting the first plurality of laser sintered layers comprises an alternating hatch laser raster that includes a scanning process along two perpendicular directions and a circumferential laser raster.

6. The method of claim 1, wherein:
   forming the orthopedic component comprises laser sintering an external surface and an internal surface of the orthopedic component, such that the external surface is separated from the internal surface by un-sintered titanium powder; and
   heat treating the orthopedic component comprises melting the un-sintered titanium powder that is between the external and internal surfaces.

7. The method of claim 1, wherein heat treating the orthopedic component comprises:
   purging an environment in which the orthopedic component is positioned to a pressure of 15 millibars or less;
   elevating a temperature of the orthopedic component to between 920° Celsius and 1000° Celsius;
   sustaining a pressure of the environment in which the orthopedic component is positioned at 98 megapascal (MPa) to 108 MPa; and
   cooling the temperature of the orthopedic component at a rate of, or less than, 10° Celsius/minute.

8. The method of claim 1, wherein machining the orthopedic component comprises removing, using grit blasting, an alpha case layer of the orthopedic component.

9. The method of claim 1, wherein machining the orthopedic component comprises forming a compressive layer of residual stresses on the orthopedic device.

10. The method of claim 1, wherein machining the orthopedic component comprises extrude honing an inner surface of the orthopedic device.

11. The method of claim 1, further comprising depositing an ion of gold and/or silver onto the orthopedic device to form an anti-microbial orthopedic device.

12. The method of claim 1, wherein the titanium powder is TiAl6V4 powder.

13. The method of claim 1, wherein the portion of a layer of the plurality of laser sintered layers is double scanned with uni-directional X and Y scanning.

14. The method of claim 1, wherein the portion of a layer of the first plurality of laser sintered layers is double scanned with multi-directional X and Y scanning.

15. The method of claim 1, wherein the portion of a layer of the first plurality of laser sintered layers is double scanned with an X and Y alternating hatch laser raster.

16. The method of claim 1, wherein the portion of a layer of the first plurality of laser sintered layers is double scanned with a circumferential laser raster.

17. The method of claim 2, wherein the titanium powder is TiAl6V4 powder.

* * * * *